US011207400B2

(12) United States Patent
Barouch et al.

(10) Patent No.: US 11,207,400 B2
(45) Date of Patent: Dec. 28, 2021

(54) COMPOSITIONS AND METHODS FOR INDUCING PROTECTIVE IMMUNITY AGAINST HUMAN IMMUNODEFICIENCY VIRUS INFECTION

(71) Applicants: Janssen Vaccines & Prevention B.V., Leiden (NL); Beth Israel Deaconess Medical Center, Inc., Boston, MA (US)

(72) Inventors: Dan Barouch, Newton, MA (US); Johanna Schuitemaker, Amstelveen (NL); Maria Grazia Pau, Leiden (NL); Danielle Van Manen, Leiden (NL); Frank Tomaka, Titusville, NJ (US); Jennifer Anne Hendriks, Poeldijk (NL)

(73) Assignees: Janssen Vaccines & Prevention B.V., Leiden (NL); Beth Israel Deaconess Medical Center, Inc., Boston, MA (US)

( * ) Notice: Subject to any disclaimer, the term of this patent is extended or adjusted under 35 U.S.C. 154(b) by 111 days.

(21) Appl. No.: 16/593,658

(22) Filed: Oct. 4, 2019

(65) Prior Publication Data

US 2020/0030437 A1    Jan. 30, 2020

Related U.S. Application Data

(60) Continuation of application No. 15/968,834, filed on May 2, 2018, now Pat. No. 10,471,137, which is a division of application No. 14/863,808, filed on Sep. 24, 2015, now Pat. No. 10,137,191.

(60) Provisional application No. 62/056,059, filed on Sep. 26, 2014.

(51) Int. Cl.

| | |
|---|---|
| *C12N 15/861* | (2006.01) |
| *C12N 15/863* | (2006.01) |
| *A61K 39/21* | (2006.01) |
| *C07K 14/005* | (2006.01) |
| *C12N 15/86* | (2006.01) |
| *A61K 39/12* | (2006.01) |
| *C12N 7/00* | (2006.01) |
| *A61K 39/00* | (2006.01) |

(52) U.S. Cl.
CPC ............. *A61K 39/21* (2013.01); *A61K 39/12* (2013.01); *C07K 14/005* (2013.01); *C12N 7/00* (2013.01); *C12N 15/86* (2013.01); *A61K 2039/55505* (2013.01); *A61K 2039/575* (2013.01); *C12N 2710/10043* (2013.01); *C12N 2710/24143* (2013.01); *C12N 2740/16034* (2013.01)

(58) Field of Classification Search
CPC .... A61K 39/12; A61K 2039/70; A61K 39/21; A61K 2039/585; A61K 39/235; C12N 15/861; C12N 15/863; C12N 15/86; C12N 15/81; C12N 15/83; C07K 14/16
See application file for complete search history.

(56) References Cited

U.S. PATENT DOCUMENTS

| | | | |
|---|---|---|---|
| 4,603,112 A | 7/1986 | Paoletti et al. | |
| 5,185,146 A | 2/1993 | Altenburger | |
| 5,639,649 A | 6/1997 | Almond et al. | |
| 5,643,576 A | 7/1997 | Johnston et al. | |
| 6,761,893 B2 | 7/2004 | Chaplin | |
| 6,911,205 B2 | 6/2005 | Sodroski et al. | |
| 7,429,653 B2 | 9/2008 | Sodroski | |
| 7,592,014 B2 | 9/2009 | Binley et al. | |
| 7,901,690 B2 | 3/2011 | Lu et al. | |
| 7,939,083 B2 | 5/2011 | Dey et al. | |
| 8,197,825 B2 | 6/2012 | Sutter | |
| 9,017,691 B2 | 4/2015 | Barouch | |
| 10,307,477 B2* | 6/2019 | Tomaka ................. | A61K 39/12 |
| 10,525,123 B2* | 1/2020 | Tomaka ................. | A61K 39/21 |
| 2003/0206926 A1 | 11/2003 | Chaplin et al. | |
| 2003/0207287 A1 | 11/2003 | Short | |
| 2006/0159699 A1 | 7/2006 | Howley et al. | |
| 2007/0166784 A1 | 7/2007 | Barnett et al. | |
| 2007/0298051 A1 | 12/2007 | Barouch et al. | |
| 2008/0199939 A1 | 8/2008 | Havenga et al. | |
| 2008/0279879 A1 | 11/2008 | Zolla-Pazner | |
| 2011/0159036 A1 | 6/2011 | Moss et al. | |
| 2011/0250220 A1 | 10/2011 | Dey et al. | |
| 2012/0045472 A1 | 2/2012 | Harrison et al. | |
| 2012/0076812 A1 | 3/2012 | Barouch et al. | |
| 2013/0189754 A1 | 7/2013 | Parks et al. | |
| 2014/0302080 A1 | 10/2014 | Barouch et al. | |
| 2014/0348791 A1 | 11/2014 | Barouch et al. | |
| 2015/0291935 A1 | 10/2015 | Barouch et al. | |
| 2016/0024156 A1 | 1/2016 | Barouch et al. | |
| 2016/0122392 A1 | 5/2016 | Baker et al. | |
| 2017/0165355 A1 | 6/2017 | Langedijk | |

FOREIGN PATENT DOCUMENTS

| | | |
|---|---|---|
| CN | 102282175 A | 12/2011 |
| EP | 2292772 A1 | 3/2011 |

(Continued)

OTHER PUBLICATIONS

Borducchi, E. N., Dec. 2016, Ad26/MVA therapeutic vaccination with TLR7 stimulation in SIV-infected rhesus monkeys, Nature 540:284-299.

(Continued)

*Primary Examiner* — Bao Q Li
(74) *Attorney, Agent, or Firm* — Ice Miller LLP

(57) ABSTRACT

Compositions, vaccines and methods for inducing an immunity, including a protective immunity, against Human Immunodeficiency Virus (HIV) infection are described. Heterologous vaccine combinations of one or more adenovirus 26 vectors using for priming immunization and an isolated HIV antigenic polypeptide in combination with one or more MVA vectors for boosting immunization induced strong protective immunity against infections by one or multiple clades of HIV.

20 Claims, 4 Drawing Sheets

Specification includes a Sequence Listing.

(56) References Cited

FOREIGN PATENT DOCUMENTS

| EP | 2319860 | A2 | 5/2011 |
|---|---|---|---|
| WO | 200070071 | A1 | 11/2000 |
| WO | 0119958 | | 3/2001 |
| WO | 200242480 | A2 | 5/2002 |
| WO | 2003048184 | A2 | 6/2003 |
| WO | 2003/104467 | A1 | 12/2003 |
| WO | 2004001032 | A2 | 12/2003 |
| WO | 2004/0044155 | | 5/2004 |
| WO | 2006002079 | | 1/2006 |
| WO | 2006020071 | | 2/2006 |
| WO | 2006/040330 | | 4/2006 |
| WO | 2007005934 | | 1/2007 |
| WO | 2007/024941 | A2 | 3/2007 |
| WO | 2007/104792 | A2 | 9/2007 |
| WO | 2007/149491 | | 12/2007 |
| WO | 2008063331 | | 5/2008 |
| WO | 2008/107370 | A1 | 9/2008 |
| WO | 2010/042942 | A2 | 4/2010 |
| WO | 2010/059732 | A1 | 5/2010 |
| WO | 2010096561 | A1 | 8/2010 |
| WO | 2011/082087 | A2 | 7/2011 |
| WO | 2011/092029 | A1 | 8/2011 |
| WO | 2012/030904 | | 3/2012 |
| WO | 2012048817 | A2 | 4/2012 |
| WO | 2012082918 | A1 | 6/2012 |
| WO | 2013055908 | | 4/2013 |
| WO | 2014/047261 | | 3/2014 |
| WO | 2014/107744 | A1 | 7/2014 |
| WO | 2014/124301 | A1 | 8/2014 |
| WO | 2015/048770 | | 4/2015 |
| WO | 2016/049287 | A1 | 3/2016 |
| WO | 2016037154 | A1 | 3/2016 |
| WO | 2017102929 | A1 | 6/2017 |

OTHER PUBLICATIONS

Franchini, G., and M. L. Bosch, 1989, Genetic relatedness of the human immunodeficiency viruses type 1 and 2 (HIV-1, HIV-2) and the simian immunodeficiency virus (SIV), Annal New York Acad. Sci. 554(1):81-87.
Guyader, M., et al., 1987, Genome organization and transactivation of the human immunodeficiency virus type 2, Nature 326:662-669.
Int'l Preliminary Report on Patentability and Written Opinion dated May 24, 2011 in Int'l Application No. PCT/US2009/064999. (9 pages).
Int'l Preliminary Report on Patentability dated Jan. 26, 2017 in Int'l Application No. PCT/US2015/51891. (7 pages).
Int'l Preliminary Report on Patentability dated Apr. 5, 2016 in Int'l Application No. PCT/US2014/059093 (7 pages).
Int'l Preliminary Report on Patentability dated Jul. 7, 2015 in Int'l Application No. PCT/US2014/010543 (7 pages).
Int'l Preliminary Search Report on Patentability dated Apr. 12, 2011 in Int'l Application No. PCT/US2009/060494 (5 pages).
Int'l Search Report and Written Opinion dated Jan. 22, 2015 in Int'l Patent Application No. PCT/US2014/059093 (10 pages).
Int'l Search Report and Written Opinion dated Feb. 5, 2016 in Int'l Application No. PCT/US2015/051891 (14 pages).
Int'l Search Report and Written Opinion dated Apr. 23, 2010 in Int'l Application No. PCT/US2009/060494 (8 pages).
Int'l Search Report dated Mar. 5, 2010 in Int'l Application No. PCT/US2009/064999. 4 pages. (4 pages).
Int'l Search Report dated Mar. 21, 2014 in Int'l Application No. PCT/US2014/010543 (5 pages).
International Search Report and Written Opinion dated Sep. 13, 2017 in Int'l Application No. PCT/EP2017/064665 (12 pages).
Li, Q. et al. Visualizing antigen-specific and infected cells in situ predicts outcomes in early viral infection. Science, 2009. 323(5922): p. 1726-9.
Liu, J, et al. Magnitude and phenotype of cellular immune responses elicited by recombinant adenovirus vectors and heterologous prime-boost regimens in rhesus monkeys. J Virol, 2008. 82(10): p. 4844-52.

Lore, K et al. Myeloid and plasmacytoid dendritic cells are susceptible to recombinant adenovirus vectors and stimulate polyfunctional memory T cell responses. J. Immunol, 2007. 179(3): p. 1721-9.
Written Opinion dated Mar. 21, 2014 in Int'l Application No. PCT/US2014/010543 (6 pages).
Gurwith et al, "Safety and Immunogenicity of an Oral, Replicating Adenovirus Serotype 4 Vector Vaccine for H5N1 Influenza: A Randomised, Double-Blind, Placebo-Controlled, Phase 1 Study", Lancet Infect Dis, vol. 13, No. 3, pp. 238-250 (2013).
Centlivre et al., "In HIV-1 Pathogenesis the Die is Cast During Primary Infections", AIDS, vol. 21, No. 1, pp. 1-11 (2007).
Flynn et al., "Placebo-controlled phase 3 trial of a recombinant glycoprotein 120 vaccine to prevent HIV-1 infection",. J. Infect Dis, vol. 191, No. 5, pp. 654-665 (2005).
Pitisuttithum et al., "Randomized, Double-Blind, Placebo-Controlled Efficacy Trial of a Bivalent Recombinant Glycoprotein 120 HIV-1 Vaccine Among Injection Drug Users in Bangkok, Thailand", J. Infect. Dis., vol. 194, No. 12, pp. 1661-1671 (2006).
Gray et al., "Safety and Efficacy of the HVTN 503/Phambili Study of a Clade-B-based HIV-1 Vaccine in South Africa: A Double-Blind, Randomised, Placebo-Controlled Test-of-Concept Phase 2b Study", Lancet Infect Dis, vol. 11, No. 7, pp. 507-515 (2011).
Buchbinder et al., Efficacy Assessment of a Cell-Mediated Immunity HIV-1 Vaccine (The Step Study): A Double-Blind, Randomised, Placebo-Controlled, Test-of-Concept Trial, Lancet, vol. 372 No. 9653, pp. 1881-1893 (2008).
Rerks-Ngarm et al.", Vaccination with ALVAC and AIDSVAX to Prevent HIV-1 Infection in Thailand", N. Engl J Med., vol. 361, No. 23, pp. 2209-2220 (2009).
McElrath et al., "HIV-1 Vaccine-Induced Immunity in the Test-of-Concept Step Study: A Case-Cohort Analysis", Lancet, vol. 372, No. 9653, pp. 1894-1905 (2008).
Vogels et al., "Replication-Deficient Human Adenovirus Type 35 Vecotrs for Gene Transfer and Vaccination: Efficient Human Cell Infection and Bypass of Preexisting Adenovirus Immunity", J. Virol, vol. 77, No. 15, pp. 8263-8271 (2003).
Farina et al., "Replication-defective Vector Based on a Chimpanzee Adenovirus", J. Virol, vol. 75, No. 23, pp. 11603-11613 (2001).
Barouch et al., "International Seroepidemiology of Adenovirus Serotypes 5, 36, 35 and 48 in Pediatric and Adult Populations", Vaccine, vol. 29: pp. 5203-5209 (2011).
Chen et al., "Adenovirus-Based Vaccines: Comparison of Vectors from Three Species of Adenoviridae", J. Virol, vol. 84, No. 20, pp. 10522-10532 (2010).
Thorner et al., "Age Dependence of Adenovirus-Specific Neutralizing Antibody Titer in Individuals From Sub-Saharan Africa", J. Clin. Microbiol, vol. 44, No. 10, pp. 3781-3783 (2006).
Spranger et al., "Quantifying Adenovirus-Neutralizing Antibodies by Luciferase Transgene Detection: Addressing Preexisting Immunity to Vaccine and Gene Therapy Vectors", J. Clin. Microbiol, vol. 41, No. 11, pp. 5046-5052 (2003).
Liu et al., "Magnitude and Phenotype of Cellular Immune Responses Elicited by Recombinant Adenovirus Vectors and Heterologous Prime Boost Regimens in Rhesus Monkeys", J. Viol., vol. 82, No. 10, pp. 4844-4852 (2008).
Liu et al., Immune Control of an SIV Challenge by a T-Cell-Based Vaccine in Rhesus Monkeys, Nature, vol. 457, No. 7225, pp. 87-91(2009).
Lore et al., "Myeloid and Plasmacytoid Dendritic Cells are Susceptible to Recombinant Adenovirus Vectors and Stimulate Polyfunctional Memory T Cell Responses", J. Immunol, vol. 179, No. 3, pp. 1721-1729 (2007).
Kuschner et al., "A Phase 3, Randomized, Double-Blind, Placebo-Controlled Study of the Safety and Efficacy of the Live, Oral Adenovirus Type 4 and Type 7 Vaccine, in U.S. Military Recruits", Vaccine, vol. 31(28), pp. 2963-2971 (2013).
Masopust et al., "Hidden Memories: Frontline Memory T Cells and Early Pathogen Interception", J. Immunol., vol. 188, No. 12, pp. 5811-5817 (2012).
Mast et al., "International Epidemiology of Human Pre-Existing Adenovirus (Ad) Type-5, Type-6, Type-26 and Type-36 Neutralizing Antibodies: Correlates of High Ad5 Titers and Implications for Potential HIV Vaccine Trials", Vaccine, vol. 28: pp. 950-957 (2010).

(56) References Cited

OTHER PUBLICATIONS

Hierholzer et al., "Adenoviruses from Patients with Aids: A Plethora of Serotypes and a Description of Five New Serotypes of Subgenus D (types 43-47).", J. Infect. Dis., vol. 158, No. 4 pp. 804-813 (1988) (Abstract Only).

Khoo et al., "Adenovirus Infections in Human Immunodeficiency Virus-Positive Patients: Clinical Features and Molecular Epidemiology", J. Infect. Dis, vol. 172, No. 3, pp. 629-637 (1995) (Abstract Only).

Janes et al., "MRKAd5 HIV-1 Gag/Pol/Nef Vaccine-Induced T-cell Responses Inadequately Predict Distance of Breakthrough HIV-1 Sequences to the Vaccine or Viral Load", PLoS One, vol. 7, No. 8, pp. e43396 (2012).

Santra et al., "Mosaic Vaccines Elicit CD8+ T Lymphocyte Responses That Confer Enhanced Immune Coverage of Diverse HIV Strains in Monkeys", Nat Med., vol. 16, No. 3, pp. 324-328 (2010).

Li et al., "Visualizing Antigen-Specific and Infected Cells in Situ Predicts Outcomes in Early Viral Infection", Science, vol. 323, No. 5922, pp. 1726-1729 (2009).

Baden et al., "First-in-human Evaluation of the Safety and Immunogenicity of a Recombinant Adenovirus Serotype 26 HIV-1 Env Vaccine (IPCAVD 001)", J. Infect. Dis., vol. 207, No. 2, pp. 240-247 (2013).

Barouch et al., "Characterization of Humoral and Cellular Immune Responses Elicited by a Recombinant Adenovirus Serotype 26 HIV-1 Env Vaccine in Healthy Adults (IPCAVD 001)", J. Infect. Dis, vol. 207, No. 2, pp. 248-256 (2013).

Jin et al., "Stabilizing Formulations for Inhalable Powders of an Adenovirus 35-Vectored Tuberculosis (TB) Vaccine (AERAS-402)", Vaccine, vol. 28, No. 27, pp. 4369-4375 (2010).

De Gruijl et al., Intradermal Delivery of Adenoviral Type-35 Vectors Leads to High Efficiency Transduction of Mature, CD8+ T Cell-Stimulating Skin-Emigrated Dendritic Cells, J. Immunol, vol. 177, No. 4, pp. 2208-2215 (2006).

Haslett et al., "Strong Human Immunodeficiency Virus (HIV)-Specific CD4+ T Cell Responses in a Cohort of Chronically Infected Patients are Associated with Interruptions in Anti-HIV Chemotherapy," J. Infect. Dis, vol. 81, No. 4, pp. 1264-1272 (2000).

Yang et al., "Highly Stable Trimers Formed by Human Immunodeficiency Virus Type 1 Envelope Glycoproteins Fused with the Trimeric Motif of T4 Bacteriophage Fibritin", J Virol., vol. 76, No. 9, pp. 4634-4642 (2002).

Chen et al., A Chimeric Protein of Simian Immunodeficiency Virus Envelope Glycoprotein gp140 and *Escherichia coli* Asparatate Transcarbamoylase, J. Virol, vol. 78, No. 9, pp. 4508-4516 (2004).

Cohen et al., "Chimpanzee Adenovirus CV-68 Adapted as a Gene Delivery Vector Interacts with the Coxsackievirus and Adenovirus Receptor", J. Gen. Virol., vol. 83, pp. 151-155 (2002).

Kobinger et al., "Chimpanzee Adenovirus Vaccine Protects Against Zaire Ebola Virus", Virology, vol. 346, pp. 394-401 (2006).

Tatsis et al., "A CD46-binding Chimpanzee Adenovirus Vector as a Vaccine Carrier", Molecular Therapy, vol. 15, No. 3, pp. 608-617 (2007).

Bangari et al., "Development of Nonhuman Adenoviruses as Vaccine Vectors", Vaccine, vol. 24, No. 7, pp. 849-26 (2006).

Lasaro et al., "New Insights on Adenovirus as Vaccine Vectors", Mol. Ther., vol. 17, No. 8, pp. 1333-1339 (2009).

Mayr et al., "The Small Pox Vaccination Strain MVA: Marker, Genetic Structure, Experience Gained with the Parenteral Vaccination and Behavior in Organisms with a Debilitated Defence Mechanism," Zentralbl Bacteriol. vol. 167, pp. 375-390 (1978) (Abstract Only).

Ambrosini et al., "Gene Transfer in Astrocytes: Comparison Between Different Delivering Methods and Expression of the HIV-1 Protein Nef.", J. Neurosci. Res., vol. 55, p. 569 (1999) (Abstract Only).

Letvin et al., "Potent, Protective Anti-HIV Immune Responses Generated by Bimodal HIV Envelope DNA Plus Protein Vaccination", Proc. Natl. Acad. Sci., vol. 94, pp. 9378-9383 (1997).

Patterson et al. "Protection Against Mucosal Simian Immunodeficiency Virus SIVmac251 Challenge by Using Replicating Adenovirus-SIV Multigene Vaccine Priming and Subunit Boosting," Journal of Virology, vol. 78, No. 5, pp. 2212-2221 (Mar. 2004).

Burke et al. "Neutralizing Antibody Responses to Subtype B and C Adjuvanted HIV Envelope Protein Vaccination in Rabbits," Virology, vol. 387, No. 1, pp. 147-156 (Apr. 2009).

Peng et al. "Replicating Rather than Nonreplicating Adenovirus-Human Immunodeficiency Virus Recombinant Vaccines Are Better at Eliciting Potent Cellular Immunity and Priming High-Titer Antibodies," Journal of Virology, vol. 79, No. 16, pp. 10200-10209 (Aug. 2005).

Lian et al., "Evaluation of Envelope Vaccines Derived from the South African Subtype C Human Immunodeficiency Virus Type 1 TV1 Strain," Journal of Virology, vol. 79, No. 21, pp. 13338-13349 (Nov. 2005).

Gomez-Roman et al., "An Adenovirus-Based HIV Subtype B Prime/Boost Vaccine Regimen Elicits Antibodies Mediating Broad Antibody-Dependent Cellular Cytotoxicity Against Non-Subtype B HIV Strains", J. Acquir. Immune Defic. Syndr., vol. 43, No. 3, pp. 270-277 (Nov. 2006).

"Endogenous Retrovirus Group K Member 25 Env Polyprotein", Database UNIPROT, Accession No. Q5GI17, 2 pages (Mar. 1, 2005).

"Recombinant Protein gp41 Heterologous Transmembrane Region, SEQ ID1," Database Geneseq, Accession No. AUR74751, 1 page, (Mar. 19, 2009).

"Transmembrane Domain Peptide, SEQ ID 14," Database Geneseq, Accession No. AEF06609, 1 page (Mar. 23, 2006).

"GCN4 Fusion Linker Peptide, SEQ ID No. 3," Database Geneseq, Accession No. AEN61500, 1 page (Mar. 8, 2007).

Abrahamyan et al, "The Cytoplasmic Tail Slows the Folding of Human Immunodeficiency Virus Type 1 Env from a late Prebundle Configuration into the Six-Helix Bundle", Journal of Virology, vol. 79, No. 1, pp. 106-115 (2005).

Wu et al, "Rational Design of Envelope Identifies Broadly Neutralizing Human Monoclonal Antibodies to HIV-1," Science, vol. 329, No. 5993, pp. 856-861 (Aug. 13, 2010).

Yang et al, "Improved Elicitation of Neutralizing Antibodies Against Primary Human Immunodeficiency Viruses by Soluble Stabilized Envelope Glycoprotein Trimers," Journal of Virology, vol. 75, No. 3, pp. 1165-1171 (Feb. 2001).

Yasmeen et al, "Differential Binding of Neutralizing and Non-Neutralizing Antibodies to Native-Like Soluble HIV-1 Env Trimers, Uncleaved Env Proteins, and Monomeric Subunits," Retrovirology, vol. 11, No. 41 (2014).

Zhou et al, "Structural Basis for Broad and Potent Neutralization of HIV-1 by Antibody VRC01," Science, vol. 329, No. 5993, pp. 811-817 (Aug. 13, 2010).

Lee et al, "A Single Point Mutation in HIV-1 V3 Loop Alters the Immunogenic Properties of rgp120," Archives of Virology, vol. 145, pp. 2087-2103 (2000).

Walker et al, "Toward an AIDS Vaccine," Science, vol. 320, pp. 760-764 (May 9, 2008).

McElrath et al, "Induction of Immunity to Human Immunodeficiency Virus Type-1 by Vaccination," Immunity, vol. 33, pp. 542-554 (Oct. 29, 2010).

Watkins et al, "Immune Escape by Human Immunodeficiency Virus Type 1 from Neutralizing Antibodies: Evidence for Multiple Pathways," Journal of Virology, vol. 67, No. 12, pp. 7493-7500 (Dec. 1993).

Sattentau, "Envelope Glycoprotein Trimers as HIV-1 Vaccine Immunogens", Vaccines, vol. 1, pp. 497-512 (2013).

Barnett et al., "Development of V2-deleted trimeric envelope vaccine candidates from human immunodeficiency virus type 1 (HIV-1) subtypes B and C," Microbes Infect, vol. 7, vol. 14, pp. 1386-1391 (2005).

Gao et al, "A Comprehensive Panel of Near-Full-Length Clones and Reference Sequences for Non-Subtype B solates of Human Immunodeficiency Virus Type 1," Journal of Virology, vol. 72, No. 7, pp. 5680-5698 (1998).

(56) References Cited

OTHER PUBLICATIONS

Yang et al, "Modifications That Stabilize Human Immunodeficiency Virus Envelope Glycoprotein Trimers in Solution," Journal of Virology, vol. 74, No. 10, pp. 4746-4754 (2000).
Desrosiers, "Prospects for an AIDS Vaccine", Nature Medicine, vol. 10, No. 3, pp. 221-223 (2004).
Gallo, "The End or the Beginning of the Drive to an HIV-Preventive Vaccine: A View from over 20 Years", The Lancet, vol. 366, No. 9500, pp. 1894-1898 (Nov. 2005).
Levine, "Why Do We Not Yet Have a Human Immunodeficiency Virus Vaccine," J. Virol., vol. 82, No. 24, pp. 11998-12000 (Dec. 2008).
Zhang et al, "Extensively Cross-Reactive Anti-HIV-1 Neutralizing Antibodies Induced by gp140 Immunization," PNAS, vol. 104, No. 24, pp. 10193-10198 (2007).
Beddows et al, "A Comparative Immunogenicity Study in Rabbits of Disulfide-Stablized, Proteolytically Cleaved, Soluble Trimeric Human Immunodeficiency Virus Type 1 gp140, Trimeric Cleavage-Defective gp140 and Monomeric gp120," Virology, vol. 360, pp. 329-340 (2007).
Berger et al, "Chemokine Receptors as HIV-1 Coreceptors: Roles in Viral Entry, Tropism and Disease," Annu. Rev. Immunol., vol. 17, pp. 657-700 (1999).
Berman et al, "Comparison of the Immune Response to Recombinant gp120 in Humans and Chimpanzees," AIDS, vol. 8, pp. 591-601 (1994).
Binley et al "A Recombinant Human Immunodeficiency Virus Type 1 Envelope Glycoprotein Complex Stabilized by 6 an Intermolecular Disulfide Bond Between the gp120 and gp41 Subunits is an Antigenic Mimic of the Trimeric Virion-Associated Structure," Journal of Virology, vol. 74, No. 2, pp. 627-643 (Jan. 2000).
Bower et al, "HIV-1 ENV gp 140 Trimers Elicit Neutralizing Antibodies Without Efficient Induction of Conformational Antibodies," Vaccine, vol. 24, pp. 5442-5451 (2006).
Burton et al, "HIV Vaccine Design and the Neutralizing Antibody Problem," Nature Immunology, vol. 5, No. 3, pp. 233-236 (Mar. 2004).
Carrow et al, "High Prevalance of Antibodies to the gp120 V3 Regional Principal Neutralizing Determinant of HIV-1 MN in Sera from Africa and the Americas," Aids Research and Human Retroviruses, vol. 7, No. 10, pp. 831-838 (1991).
Chen et al, "Expression, Purification, and Characterization of gp160e, the Soluble, Trimeric Ectodomain of the Simian Immunodeficiency Virus Envelope Glycoprotein, gp160," The Journal of Biological Chemistry, vol. 275, No. 45, pp. 34946-34953 (Nov. 10, 2000).
Crooks et al, "A Comparative Immunogenicity Study of HIV-1 Virus-Like Particles Bearing Various Forms of Envelope Proteins, Particles Bearing No Envelope and Soluble Monomeric gp120," ScienceDirect, Virology vol. 366, pp. 245-262 (2007).
Derby et al, "Isolation and Characterization of Monoclonal Antibodies Elicited by Trimeric HIV-1 ENV gp140 Protein 14 Immunogens," Virology, vol. 366, pp. 433-445 (2007).
Dey et al, "Characterization of Human Immunodeficiency Virus Type 1 Monomeric and Trimeric gp120 Glycoproteins Stabilized in the CD4-Bound State: Antigenicity, Biophysics, and Immunogenicity," Journal of Virology, vol. 81, No. 11, pp. 5579-5593 (Jun. 2007).
Gallo et al, "The HIV Env-mediated Fusion Reaction," Biochemics et Biophysica Acta, pp. 36-50 (2003).
Kang et al, "Structural and Immunogenicity Studies of a Cleaved, Stabilized Envelope Trimer Derived from Subtype A HIV-1," Vaccine, vol. 27, pp. 5120-5132 (2009).
Kim et al, "Comparison of HIV Type 1 ADA gp120 Monomers Versus gp140 Trimers as Immunogens for the Induction of Neutralizing Antibodies," AIDS Research and Human Retroviruses, vol. 21, No. 1, pp. 58-67 (2005).
Li et al, "Human Immunodeficiency Virus Type 1 env Clones from Acute and Early Subtype B Infections for Standardized Assessments of Vaccine-Elicited Neutralizing Antibodies," Journal of Virology, vol. 79, No. 16, pp. 10108-10125 (Aug. 2005).

Li et al, "Genetic and Neutralization Properties of Subtype C Human Immunodeficiency Virus Type 1 Molecular env Clones From Acute Early Heterosexually Acquired Infections in Southern Africa," Journal of Virology, vol. 80, No. 23, 11776-11790 (Dec. 2006).
Montefiori et al, "Antibody-Based HIV-1 Vaccines: Recent Developments and Future Directions," PLOS Medicine, vol. 4, No. 12, pp. e348 (2007).
Montefiori, "Measuring HIV Neutralization in a Luciferase Reporter Gene Assay," HIV Protocols Second 25 Edition, vol. 485, pp. 395-405 (2009).
Morner et al, "Human Immunodeficiency Virus Type 1 ENV Trimer Immunization of Macaques and Impact of D Priming with Viral Vector or Stabilized Core Protein," Journal of Virology, vol. 83, No. 2, pp. 540-551 (Jan. 2009).
Nara et al, "Purified Envelope Glycoproteins from Human Immunodeficiency Virus Type 1 Variants Induce Individual, Type-Specific Neutralizing Antibodies," Journal of Virology, vol. 62, No. 8, pp. 2622-2628 (Aug. 1988).
Page et al, "Studies on the Immunogenicity of Chinese Hamster Ovary Cell-Derived Recombinant gp120 (HIV-1111B)," Vaccine, vol. 9, pp. 47-52 (Jan. 1991).
Pantophlet et al, "GP120: Target for Neutralizing HIV-1 Antibodies," Annu. Rev. Immunol., vol. 24, pp. 739-769 (2006).
Polonis et al, "Recent Advances in the Characterization of HIV-1 Neutralization Assays for Standardized Evaluation of the Antibody Response to Infection and Vaccination," Virology, vol. 375, pp. 315-320 (2008).
Rodenburg et al, "Near Full-Length Clones and Reference Sequences for Subtype C Isolates of HIV Type 1 from Three Different Continents," AIDS Research and Human Retroviruses, vol. 17, No. 2, pp. 161-168 (2001).
Scheid et al, "Broad Diversity of Neutralizing Antibodies Isolated From Memory B Cells in HIV-Infected Individuals," D Nature, vol. 458, pp. 636-640 (Apr. 2, 2009).
Vaine et al, "Improved Induction of Antibodies Against Key Neutralizing Epitopes by Human Immunodeficiency Virus Type 1 gp120 DNA Prime-Protein Boost Vaccination Compared to gp120 Protein-Only Vaccination," Journal of Virology, vol. 82, No. 15, pp. 7369-7378 (Aug. 2008).
Vogel et al, "The Majority of Neutralizing Abs in HIV-1-Infected Patients Recognize Linear V3 Loop Sequences," The Journal of Immunology, vol. 153, pp. 1895-1904 (1994).
Wyatt et al, "The Antigenic Structure of the HIV gp120 Envelope Glycoprotein," Nature, vol. 393, pp. 705-711 (Jun. 18, 1998).
Zolla-Pazner et al, "Focusing the Immune Response on the V3 Loop, a Neutralizing Epitope of the HIV-1 gp210 Envelope," Virology, vol. 372, pp. 233-246 (2008).
Jeffs et al, "Expression and Characterization of Recombinant Oligomeric Envelope Glycoproteins Derived From Primary Isolates of HIV-1," Vaccine, vol. 22, No. 8, pp. 1032-1046 (2004).
Genbank Accession No. AF286227.1, "HIV-1 strain 97Za012 from South Africa, complete genome." Accessed Jan. 6, 2016.
Salminen et al, "Full-length Sequence of an Ethiopian Human Immunodeficiency Virus Type 1 (HIV-1) Isolate of Genetic Subtype C," AIDS Res. Human Retroviruses, vol. 12, No. 14, pp. 1329-1339 (1996).
Bower et al, "Elicitation of Neutralizing Antibodies with DNA Vaccines Expressing Soluble Stabilized Human Immunodefiency Virus Type 1 Envelope Glycoprotein Trimers Conjugated to C3d", Journ. of Viro., vol. 78, No. 9, pp. 4710-4719 (May 2004).
Nkolola et al, "Stability and Neutralization Capacity of a Novel Mosaic HIV-1 gp140 trimer in a Guinea Pig Model" AIDS Vaccine Poster, Ragon Institute, 1 pg. (2012).
Nkolola et al, "Stability and Neutralization Capacity of a Novel Mosaic HIV-1 gp140 Trimer in a Guinea Pig Model," Retrovirology, vol. 9, Supp. 2, pp. 299 (2012).
Pinter, "Roles of HIV-1 Env Variable Regions in Viral Neutralization and Vaccine Development", Current HIV Research, vol. 5, No. 6, pp. 542-553 (2007).
Shu et al., "Efficient Boosting After Plasmid DNA or Recombinant Adenovirus Immunization with HIV-1 Vaccine Constructs", Vaccine, vol. 25, No. 8, pp. 1398-1408 (2007).

(56) References Cited

OTHER PUBLICATIONS

Muthumani et al., "HIV-1 Env DNA Vaccine plus PRotein Boost Delivered by EP Expands B- and T-Cell Responses and Neutralizing Phenotype In Vivo", PLOS One, vol. 8, No. 12, 12 pgs (Dec. 2013).
Barouch et al., "Accelerating HIV-1 Vaccine Efficacy Trials", Cell, vol. 159, No. 5, pp. 969-792 (Nov. 2014).
Haynes et al, "Immune-Correlates Analysis of an HIV-1 Vaccine Efficacy Trial," The New England Journal of Medicine, vol. 366, No. 14, pp. 1275-1286 (2012).
Sarzotti-Kelsoe et al, "Optimization and Validation of the TZM-bl Assay for Standardized Assessments of Neutralizing Antibodies Against HIV-1," Journal of Immunological Methods, vol. 409, pp. 131-146 (2014).
Schnierle et al, "Pseudotyping of Murine Leukemia Virus with the Envelope Glycoproteins of HIV Generates a Retroviral Vector with Specificity of infection for CD4-Expressing Cells," Proceedings of the National Academy of Sciences of the United States of America, vol. 94, pp. 8640-8645 (Aug. 1997).
Walker et al, "Broad and Potent Neutralizing Antibodies from an African Donor Reveal a New HIV-1 Vaccine Target," Science, vol. 326, No. 5950, pp. 285-289 (Oct. 9, 2009).
Baicu et al., "Acid-base Buffering in Organ Preservation Solutions as a Function of Temperature: New Parameters for Comparing Buffer Capacity and Effciency", Cryobiology, vol. 45, pp. 33-48 (2002).
Barouch et al., "Protective Efficacy of Adenovirus/Protein Vaccines Against SIV Challenges in Rhesus Monkeys", Science, vol. 349, No. 6245, pp. 320-324 (Jul. 2015).
Barouch et al, "Protective Efficacy of a Global HIV-1 Mosaic Vaccine against Heterologous SHIV Challenges in Rhesus Monkeys," Cell, vol. 155, pp. 531-539 (Oct. 2013).
Hoganson et al., "Development of a Stable Adenoviral Vector Formulation", BioProcessing Journ., pp. 43-48 (Mar. 2002).
Kamerzell et al., "Protein-Excipient Interactions: Mechanisms and Biophysical Characterization Applied to Protein Formulation Development", Advanced Drug Delivery Review, vol. 63, pp. 1118-1159 (2011).
Kovacs et al., "HIV-1 Envelope Trimer Elicits more Potent Neutralizing Antibody Responses than Monomeric gp120", Proc. Natl. Acac. Sci., vol. 109, No. 30, pp. 12111-12116 (2012).
Lepe-Zuniga et al., "Toxicity of Light-Exposed Hepes Media", Journ. of Immun. Methods, vol. 103, pp. 145 (1987).
Sanders et al., "Brunenders: A Partially Attenuated Historic Poliovirus Type 1 Vaccine Strain", Journ. of General Viro., vol. 96, pp. 2614-2622 (2015).
Nkolola et al., "Breadth of Neutralizing Antibodies Elicited by Stable, Homogeneous Clade A and Clade C HIV-1 gp140 Envelope Trimers in Guinea Pigs", Journ. of Viro., vol. 84. No. 7, pp. 3270-3279 (Apr. 2010).
Nkolola et al., "Characterization and Immunogenicity of a Novel Mosaic M HIV-1 gp140 Trimer", Journ. of Virology, vol. 88, No. 17, pp. 9538-9552 (Sep. 2014).
Uchiyama, "Liquid Formulation for Antibody Drugs", Biochimica Biophysica, vol. 1844, pp. 2041-2052 (2014).
Zigler et al., "Analysis of the Cytotoxic Effects of Light-Exposed Hepes-Containing Culture Medium", In Vitro Cell Dev. Biol., vol. 21, No. 5, pp. 282-287 (1985).
Clapp et al. "Vaccines with Aluminum-Containing Adjuvants: Optimizing Vaccine Efficacy and Thermal Stability", J. Pharm. Sci. vol. 100, No. 2: pp. 388-401 (2011).
Wiggan et al. "Novel Formulations Enhance the Thermal Stability of Live-Attenuated Flavivirus Vaccines," Vaccine, vol. 29, pp. 7456-7462 (2011).
De Taeye et al, "Immunogenicity Of Stabilized HIV-1 Envelope Trimers With Reduced Exposure Of Non-Neutralizing Epitopes," Cell, vol. 163, pp. 1702-1715 (2015).
Julien et al, "Design And Structure Of Two HIV-1 Clade C SOSIP. 664 Trimers That Increase The Arsenal Of Native-Like Env Immunogens," PNAS, vol. 112, No. 38, pp. 11947-11952 (2015).

Kwon et al, "Crystal Structure, Conformational Fixation And Entry-Related Interactions Of Mature Ligand-Free HIV-1 ENV," Nature Structural & Molecular Biology, vol. 22, No. 7, pp. 522-531 (2015).
Pugach et al, "A Native-Like SOSIP.664 Trimer Based On An HIV-1 Subtype B Env Gene," Journal of Virology, vol. 89, No. 6, pp. 3380-3395 (2015).
Altschul et al, "Gapped BLAST and PSI-BLAST: a new generation of protein database search programs," Nucleic Acids Research, vol. 25, No. 17, pp. 3389-3402 (1997).
Eglen et al, "The Use Of AlphaScreen Technology In HTS: Current Status," Current Chemical Genomics, vol. 1, pp. 2-10 (2008).
Abbink et al, "Comparative seroprevalence and immunogenicity of six rare serotype recombinant adenovirus vaccine Vectors from subgroups B and D," Journal of Virology, vol. 81, No. 9, pp. 4654-4663 (2007).
Barouch et al, "Mosaic HIV-1 Vaccines Expand The Breadth And Depth Of Cellular Immune Responses In Rhesus Monkeys," Nat. Med., vol. 16, No. 3, pp. 319-323 (2010).
Georgiev et al, "Single-Chain Soluble BG505.SOSIP gp140 Trimers As Structural And Antigenic Mimics Of Mature Closed HIV-1 Env," Journal of Virology, vol. 89, pp. 5318-5329 (2015).
Bale et al, "Covalent Linkage Of HIV-1 Trimers To Synthetic Liposomes Elicits Improved B Cell And Antibody Responses," Journal of Virology, vol. 91, No. 16, pp. e00443-17 (2017).
Harris et al, "Trimeric HIV-1 Glycoprotein gp140 Immunogens And Native HIV-1 Envelope Glycoproteins Display The Same Closed And Open Quaternary Molecular Architectures," PNAS, vol. 108, No. 28, pp. 11440-11445 (2011).
Guenaga et al, "Glycine Substitution At Helix-To-Coil Transitions Facilitates The Structural Determination Of A Stabilized Subtype C HIV Envelope Glycoprotein," Immunity, vol. 46, pp. 792-803 (2017).
Lopez-Sagaseta et al, "Self-Assembling Protein Nanoparticles In The Design Of Vaccines," Computational and Structural Biotechnology Journal, vol. 14, pp. 58-68 (2016).
Kesavardhana et al, "Stabilizing The Native Trimer Of HIV-1 Env By Destabilizing The Heterodimeric Interface Of The gp41 Postfusion Six-Helix Bundle," Journal of Virology, vol. 88, No. 17, pp. 9590-9604 (2014).
He et al, "Presenting Native-Like Trimeric HIV-1 Antigens With Self-Assembling Nanoparticles," Nature Communications, vol. 7, No. 1, pp. 1-15 (2016).
Sanders et al, "Stabilization Of The Solubale, Cleaved, Trimeric Form Of The Envelope Glycoprotein Complex Of Human Immunodeficiency Virus Type 1," Journal of Virology, vol. 76, No. 17, pp. 8875-8889 (2002).
Kong et al, "Uncleaved Prefusion-Optimized gp140 Trimers Derived From Analysis Of HIV-1 Envelope Metastability," Nature Communications, vol. 7, No. 1, pp. 1-15 (2016).
Zhang et al, "Expression, Purification, And Characterization Of Recombinant HIV gp140," Journal of Biological Chemistry, vol. 276, No. 43, pp. 39577-39585 (2001).
Sanders et al, "HIV-1 Neutralizing Antibodies Induced By Native-Like Envelope Trimers," Science, vol. 349, Issue 6244, pp. 1-17 (2015).
Zhao et al, "Nanoparticle Vaccines," Vaccines, vol. 32, pp. 327-337 (2014).
Sharma et al, "Cleavage-Independent HIV-1 Env Trimers Engineered As Soluble Native Spike Mimetics For Vaccines Design," Cell Reports, vol. 11, pp. 1-12 (2015).
Kushnir et al, "Virus-Like Particles As A Highly Efficient Vaccine Platform: Diversity Of Targets And Production Systems And Advances In Clinical Development," Vaccine, vol. 31, pp. 58-83 (2012).
Achenbach et al., "Effect of Therapeutic Intensification Followed by HIV DNA Prime AND rAd5 Boost Vaccination on HIV-specific Immunity and HIV Reservoir (EraMune 02): a Multicentre Randomised Clinical Trial", The Lancet, vol. 2, No. 3, pp. e82-e91 (Mar. 2015).
Gach et al., "HIV-1-Specific Antibody Response and Function after DNA Prime and Recombinant Adenovirus 5 Boost HIV Vaccine in HIV-Infected Subjects", PLOS One, vol. 11, No. 8, pp. 17 (Aug. 2016).

(56) References Cited

OTHER PUBLICATIONS

Katlama et al., "Barriers to a Cure for HIV: New Ways to Target and Eradicate HIV-1 Reservoirs", The Lancet, vol. 381, No. 988., pp. 2109-2117 (Jun. 2013).
Thompson et al., "DNA/MVA Vaccination of HIV-1 Infected Participants with Viral Suppression on Antiretroviral Therapy, Followed by Treatment Interruption: Elicitation of Immune Responses without Control of Re-Emergent Virus", PLOS ONE, vol. 11, No. 10, pp. 25 (Oct. 2016).
Blanchard et al., "Modified Vaccinia Virus Ankara Undergoes Limited Replication in Human Cells and Lacks Several Immunomodulatory Proteins: Implications for Use as a Human Vaccine", Journ. of Gen. Viro., vol. 79, pp. 1159-1167 (1998).
Carcelain et al., "Immune Interventions in HIV Infection", Immunol Rev., vol. 254, No. 1, pp. 355-371 (2013).
Carroll et al., "Host Range and Cytopathogenicity of the Highly Attenuated MVA Strain of Vaccinia Virus: Propagation and Generation of Recombinant Viruses in a Nonhuman Mammalian Cell Line", Virology, vol. 238, pp. 198-211 (1997).
Chen et al., "Protection of Rhesus Macaques Against Disease Progression from Pathogenic SHIV-89.6PD by Vaccination with Phage-Displayed HIV-1 Epitopes", Nat. Med., vol. 7, No. 11, pp. 1225-1231 (2001).
Fischer et al., "Polyvalent Vaccines for Optimal Coverage of Potential T-Cell Epitopes in Global HIV-1 Variants", Nat. Med., vol. 13, No. 1, pp. 100-106 (Jan. 2007).
Gianella et al., "Effect of Early Antiretroviral Therapy During Primary HIV-1 Infection on Cell-Associated HIV-1 DNA and Plasma HIV-1 RNA", Antiviral Therapy, vol. 16, No. 4, pp. 535-545 (2011).
Goujard et al., "HIV-1 Control After Transient Antiretroviral Treatment Initiated in Primary Infection: Role of Patient Characteristics and Effect of Therapy", Antiviral Therapy, vol. 17, No. 6, pp. 1001-1009 (2012).
Hamlyn et al., "Plasma HIV Viral Rebound Following Protocol-Indicated Cessation of ART Commenced in Primary and Chronic HIV Infection", PLOS ONE, vol. 7, No. 8, 8 pgs (Aug. 2012).
Havenga et al., "Novel Replication-Incompetent Adenoviral B-Group Vectors: High Vector Stability and Yield in PER. C6 Cells", Journ. of Gen Viro., vol. 87, pp. 2135-2143 (2006).
Lodi et al., "Immunovirologic Control 24 Months After Interruption of Antiretroviral Therapy Initiated Close to HIV Seroconversion", Archives of Internal Medicine, vol. 172, No. 16, pp. 1252-1255 (2012).
Saez-Cirion et al., "Post-Treatment HIV-1 Controllers with a Long-Term Virological Remission after the Interruption of Early Initiated Antiretroviral Therapy ANRS VISCONTI Study", PLOS Pathogens, vol. 9, No. 3, 12 pgs (Mar. 2013).
UNAIDS, "Report on the Global AIDS Epidemic", 198 pgs (2013).
Williams et al., "HIV-1 DNA Predicts Disease Progression and Post-Treatment Virological Control", eLife, vol. 3, 16 pgs (2014).
Stickl, "Smallpox Vaccination and it's Consequences: First Experiences with the Highly Attenuated Smallpox Vaccine MVA", Preventive Medicine, vol. 3, pp. 97-101 (1974).
Blondelle et al., "Immunogenically Optimized Peptides Derived from Natural Mutants of HIV CTL Epitopes and Peptide Combinational Libraries", Biopolymers, vol. 90(5), pp. 683-694 (2008).
Fischer et al., "Coping with Viral Diversity in HIV vaccine Design: A Response to Nickle et al.," PLoS Comput Bioi., vol. 4, No. 1, pp. 175-179 (2008).
Kong et al., "Expanded Breadth of the T-Cell Response to Mosaic Human Immunodeficiency Virus Type 1 Envelope DNA Vaccination," J. Viral., vol. 83, No. 5, pp. 2201-2215 (2009).
Korber et al., "T-Cell Vaccine Strategies for Human Immunodeficiency Virus, The Virus with a Thousand Faces," J. Viral., vol. 83, No. 17, pp. 8300-8314 (2009).
NCBI Blast for GenBank AAY23526.1, Jul. 2016, "Envelope glycoprotein Human immunodeficiency virus 1", downloaded from web page: http://www.ncbi.nlm.nih.gov/protein/62956393, Download date: Feb. 8, 2018 (2 pages).

Thurmond et al., "Web-Based Design and Evaluation of T-cell Vaccine Candidates," Bioinformatics, vol. 24, No. 14, pp. 1639-1640 (2008).
Gotch et al., "Candidate Vaccines for Immunotherapy in HIV", HIV Medicine, vol. 2, pp. 260-265 (2001).
Girard et al., A Review of Vaccine Research and Development: The Human Immunodeficiency Virus (HIV), Vaccine, vol. 24, pp. 4062-4081 (2006).
Barouch, "Challenges in the Development of an HIV-1 Vaccine", Nature, vol. 455, No. 2, pp. 613-619 (2008).
Cohen, "Did Merck's Failed HIV Vaccine Cause Harm?" Science, vol. 318, pp. 1048-1049 (2007).
Abrahams et al, "Quantitating the Multiplicity of Infection with Human Immunodeficiency Virus Type 1 Subtype C Reveals a Non-Poisson Distribution of Transmitted Variants," Journal of Virology, vol. 83, No. 8, pp. 3556-3567 (Apr. 2009).
Amanna et al, "Contributions of Humoral and Cellular Immunity to Vaccine-Induced Protection in Humans," Virology, vol. 411, No. 2, pp. 206-215 (2011).
Baba et al, "Human Neutralizing Monoclonal Antibodies of the IgG1 Subtype Protect Against Mucosal Simian-Human Immunodeficiency Virus Infection," Nature Medicine, vol. 6, No. 2, pp. 200-206 (2000).
Calarese et al, "Antibody Domain Exchange is an Immunological Solution to Carbohydrate Cluster Recognition," Science, vol. 300, No. 5628, pp. 2065-2071 (2003).
Cardoso et al, "Broadly Neutralizing Anti-HIV Antibody 4E10 Recognizes a Helical Conformation of a Highly Conserved Fusion-Associated Motif in gp41," Immunity, vol. 22, No. 2, pp. 163-173 (Feb. 2005).
Cardoso et al, "Structural Basis of Enhanced Binding of Extended and Helically Constrained Peptide Epitopes of the Broadly Neutralizing HIV-1 Antibody 4E1 0," Journal of Molecular Biology, vol. 365, No. 5, pp. 1533-1544 (2007).
Catanzaro et al, "Phase I Clinical Evaluation of a Six-Plasmid Multiclade HIV-1 DNA Candidate Vaccine," Vaccine, vol. 25, No. 20, pp. 4085-4092 (2007).
Checkley et al, "HIV-1 Envelope Glycoprotein Biosynthesis, Trafficking, and Incorporation," Journal of Molecular Biology, vol. 410, No. 4, pp. 582-608 (2011).
Cho et al, "Polyvalent Envelope Glycoprotein Vaccine Elicits a Broader Neutralizing Antibody Response But is Unable to Provide Sterilizing Protection Against Heterologous Simian/Human Immunodeficiency Virus Infection in Pigtailed Macaques," Journal of Virology, vol. 75, No. 5, pp. 2224-2234 (Mar. 2001).
Cohen, "Naked DNA Points Way to Vaccines," Science, vol. 259, pp. 1691-1692 (Mar. 1993).
Davenport et al, "Binding Interactions Between Soluble HIV Envelope Glycoproteins and Quaternary-Structure-Specific Monoclonal Antibodies PG9 and PG16," Journal of Virology, vol. 85, No. 14, pp. 7095-7107 (Jul. 2011).
Doores et al, "Antibody 2G12 Recognizes Di-Mannose Equivalently in Domain- and Nondomain-Exchanged Forms but Only Binds the HIV-1 Glycan Shield if Domain Exchanged," Journal of Virology, vol. 84, No. 20, pp. 10690-10699 (2010).
Doria-Rose et al, "Frequency and Phenotype of Human Immunodeficiency Virus Envelope-Specific B Cells from Patients with Broadly Cross-Neutralizing Antibodies," Journal of Virology, vol. 83, No. 1, pp. 188-199 (Jan. 2009).
Engelhardt et al, "Ablation of E2A in Recombinant Adenoviruses Improves Transgene Persistence and Decreases Inflammatory Response in Mouse Liver," Proceedings of the National Academy of Sciences of the United States of America, vol. 91, No. 13, pp. 6196-6200 (Jun. 1994).
Falkowska et al, "PGV04, an HIV-1 gp120 CD4 Binding Site Antibody, is Broad and Potent in Neutralization but Does Not Induce Conformational Changes Characteristic of CD4," Journal of Virology, vol. 86, No. 8, pp. 4394-4403 (2012).
Fiebig et al, "Neutralizing Antibodies Against Conserved Domains of p15E of Porcine Endogenous Retroviruses: Basis for a Vaccine for Xenotransplantation?" Virology, vol. 307, No. 2, pp. 406-413 (2003).

(56) References Cited

OTHER PUBLICATIONS

Fischer et al, "Identification of a Peptide Mimicking the Binding Pattern of an Antiphospholipid Antibody," Immunobiology, vol. 211, No. 9, pp. 695-699 (2006).
Freeman et al, "Crystal Structure of HIV-1 Primary Receptor CD4 in Complex with a Potent Antiviral Antibody," Structure, vol. 18, No. 12, pp. 1632-1641 (Dec. 8, 2010).
Frey et al, "A Fusion-Intermediate State of HIV-1 gp41 Targeted by Broadly Neutralizing Antibodies," Proceedings of the National Academy of Sciences of the United States of America, vol. 105, No. 10, pp. 3739-3744 (Mar. 11, 2008).
Fynan et al, "DNA Vaccines: Protective Immunizations by Parenteral, Mucosal, and Gene-Gun Inoculations," Proceedings of the National Academy of Sciences of the United States of America, vol. 90, No. 24, pp. 11478-11482 (Dec. 1993).
Gao et al, "Antigenicity and Immunogenicity of a Synthetic Human Immunodeficiency Virus Type 1 Group M Consensus Envelope Glycoprotein," Journal of Virology, vol. 79, No. 2, pp. 1154-1163 (Jan. 2005).
Gao et al, "Centralized HIV-1 Envelope Immunogens and Neutralizing Antibodies," Current HIV Research, vol. 5, No. 6, pp. 572-577 (2007).
Gao et al, "Molecular Cloning and Analysis of Functional Envelope Genes from Human Immunodeficiency Virus Type 1 Sequence Subtypes A through G" Journal of Virology, vol. 70, No. 3, pp. 1651-1667 (Mar. 1996).
Gaschen et al, "Diversity Consideration in HIV-1 Vaccine Selection," Science, vol. 296, No. 5577, pp. 2354-2360 (Jun. 28, 2002).
GenBank Accession No. KC769514. Retrieved on Dec. 30, 2014 (2 pages).
Georgiev et al, "Delineating Antibody Recognition in Polyclonal Sera from Patterns of HIV-1 Isolate Neutralization," Science, vol. 340, No. 6133, pp. 751-756 (2013).
Graham et al, "Phase 1 Safety and Immunogenicity Evaluation of a Multiclade HIV-1 DNA Candidate Vaccine," The Journal of Infectious Diseases, vol. 194, No. 12, pp. 1650-1660 (Dec. 15, 2006).
Gray et al, "Isolation of a Monoclonal Antibody That Targets the Alpha-2 Helix of gp120 and Represents the Initial Autologous Neutralizing-Antibody Response in an HIV-1 Subtype C-Infected Individual," Journal of Virology, vol. 85, No. 15, pp. 7719-7729 (Aug. 2011).
Grundner et al, "Analysis of the Neutralizing Antibody Response Elicited in Rabbits by Repeated Inoculation with Trimeric HIV-1 Envelope Glycoproteins," Virology, vol. 331, No. 1, pp. 33-46 (2005).
Hammer et al, "Efficacy Trial of a DNA/rAd5 HIV-1 Preventive Vaccine," The New England Journal of Medicine, vol. 369, No. 22, pp. 2083-2092 (Nov. 28, 2013).
Huang et al, "Broad and Potent Neutralization of HIV-1 by a gp41-Specific Human Antibody," Nature, vol. 491, No. 7424, pp. 406-412 (2012).
Julien et al, "Asymmetric Recognition of the HIV-1 Trimer by Broadly Neutralizing Antibody PG9," Proceedings of the National Academy of Sciences of the United States of America, vol. 110, No. 11, pp. 4351-4356 (Mar. 12, 2013).
Julien et al, "Broadly Neutralizing Antibody PGT121 Allosterically Modulates CD4 Binding via Recognition of the HIV-1 gp120 V3 Base and Multiple Surrounding Glycans," PLOS Pathogens, vol. 9, No. 5, pp. e1003342 (May 2013).
Kochanek et al, "A New Adenoviral Vector: Replacement of All Viral Coding Sequences with 28 kb of DNA Independently Expressing Both Full-Length Dystrophin and Beta-Galactosidase," Proceedings of the National Academy of Sciences of the United States of America, vol. 93, No. 12, pp. 5731-5736 (Jun. 1996).
Kothe et al, "Ancestral and Consensus Envelope Immunogens for HIV-1 Subtype C," Virology, vol. 352, No. 2, pp. 438-449 (2006).
Kothe et al, "Antigenicity and Immunogenicity of HIV-1 Consensus Subtype B Envelope Glycoproteins," Virology, vol. 360, No. 1, pp. 218-234 (Mar. 30, 2007).
Kwong et al, "Structure of an HIV gp120 Envelope Glycoprotein in Complex with the CD4 Receptor and a Neutralizing Human Antibody," Nature, vol. 393, No. 6686, pp. 648-659 (Jun. 18, 1998).
Li et al, "Broad HIV-1 Neutralization Mediated by CD4-Binding Site Antibodies," Nature Medicine, vol. 13, No. 9, pp. 1032-1039 (Sep. 2007).
Li et al, "Characterization of Antibody Responses Elicited by Human Immunodeficiency Virus Type 1 Primary Isolate Trimeric and Monomeric Envelope Glycoproteins in Selected Adjuvants," Journal of Virology, vol. 80, No. 3, pp. 1414-1426 (Feb. 2006).
Li et al, "Evidence for Potent Autologous Neutralizing Antibody Titers and Compact Envelopes in Early Infection with Subtype C Human Immunodeficiency Virus Type 1," Journal of Virology, vol. 80, No. 11, pp. 5211-5218 (Jun. 2006).
Li et al, "Removal of a Single N-Linked Glycan in Human Immunodeficiency Virus Type 1 gp120 Results in an Enhanced Ability to Induce Neutralizing Antibody Responses," Journal of Virology, vol. 82, No. 2, pp. 638-651 (Jan. 2008).
Liao et al, "A Group M Consensus Envelope Glycoprotein Induces Antibodies That Neutralize Subsets of Subtype B and C HIV-1 Primary Viruses," Virology, vol. 353, No. 2, pp. 268-282 (Sep. 30, 2006).
Liao et al, "Antigenicity and Immunogenicity of Transmitted/Founder, Consensus, and Chronic Envelope Glycoproteins of Human Immunodeficiency Virus Type 1," Journal of Virology, vol. 87, No. 8, pp. 4185-4201 (Apr. 2013).
Liao et al, "Co-Evolution of a Broadly Neutralizing HIV-1 Antibody and Founder Virus," Nature, vol. 496, No. 7446, pp. 469-476 (Apr. 25, 2013).
Lin et al, "Designing Immunogens to Elicit Broadly Neutralizing Antibodies to the HIV-1 Envelope Glycoprotein," Current HIV Research, vol. 5, No. 6, pp. 514-541 (2007).
Lynch et al, "The Development of CD4 Binding Site Antibodies During HIV-1 Infection," Journal of Virology, vol. 86, No. 14, pp. 7588-7595 (Jul. 2012).
Malherbe et al, "Sequential Immunization with a Subtype B HIV-1 Envelope Quasispecies Partially Mimics the In Vivo Development of Neutralizing Antibodies," Journal of Virology, vol. 85, No. 11, pp. 5262-5274 (Jun. 2011).
Mangeat et al, "Lentiviral Vectors and Antiretroviral Intrinsic Immunity," Human Gene Therapy, vol. 16, No. 8, pp. 913-920 (Aug. 2005).
Mascola et al, "Protection of Macaques Against Pathogenic Simian/Human Immunodeficiency Virus 89.6PD by Passive Transfer of Neutralizing Antibodies," Journal of Virology, vol. 73, No. 5, pp. 4009-4018 (May 1999).
Mascola et al, "Protection of Macaques Against Vaginal Transmission of a Pathogenic HIV-1/SIV Chimeric Virus by Passive Infusion of Neutralizing Antibodies," Nature Medicine, vol. 6, No. 2, pp. 207-210 (Feb. 2000).
McBurney et al, "Evaluation of Heterologous Vaginal SHIV SF162p4 Infection Following Vaccination with a Polyvalent Clade B Virus-Like Particle Vaccine," AIDS Research and Humam Retroviruses, vol. 28, No. 9, pp. 863-872 (2012).
McBurney et al, "Human Immunodeficiency Virus-Like Particles with Consensus Envelopes Elicited Broader Cell-Mediated Peripheral and Mucosal Immune Responses than Polyvalent and Monovalent Env Vaccines," Vaccine, vol. 27, No. 32, pp. 4337-4349 (2009).
McCoy et al, "Potent and Broad Neutralization of HIV-1 by a Llama Antibody Elicited by Immunization," The Journal of Experimental Medicine, vol. 209, No. 6, pp. 1091-1103 (2012).
McGuire et al, "Engineering HIV Envelope Protein to Activate Germline B Cell Receptors of Broadly Neutralizing Anti-CD4 Binding Site Antibodies," The Journal of Experimental Medicine, vol. 210, No. 4, pp. 655-663 (2013).
Pancera et al, "Crystal Structure of PG16 and Chimeric Dissection with Somatically Related PG9: Structure-Function Analysis of Two Quaternary-Specific Antibodies That Effectively Neutralize HIV-1," Journal of Virology, vol. 84, No. 16, pp. 8098-8110 (Aug. 2010).
McLellan et al, "Structure of HIV-1 gp120 V1/V2 Domain with Broadly Neutralizing Antibody PG9," Nature, vol. 480, No. 7377, pp. 336-343 (2011).

(56) References Cited

OTHER PUBLICATIONS

Montefiori, "Evaluating Neutralizing Antibodies Against HIV, SIV, and SHIV in Luciferase Reporter Gene Assays," Current Protocols in Immunology, vol. 12, No. 11, pp. 1-17 (2004).
Mouquet et al, "Complex-Type N-Glycan Recognition by Potent Broadly Neutralizing HIV Antibodies," Proceedings of the National Academy of Sciences of the United States of America, vol. 109, No. 47, pp. E3268-E3277 (2012).
Ofek et al, "Structure and Mechanistic Analysis of the Anti-Human Immunodeficiency Virus Type 1 Antibody 2F5 in Complex with Its gp41 Epitope," Journal of Virology, vol. 78, No. 19, pp. 10724-10737 (Oct. 2004).
Pancera et al, "Structure of HIV-1 gp120 with gp41-Interactive Region Reveals Layered Envelope Architecture and Basis of Conformational Mobility," Procedures of the National Academy of Sciences of the United States of America, vol. 107, No. 3, pp. 1166-1171 (2010).
Pejchal et al, "A Potent and Broad Neutralizing Antibody Recognizes and Penetrates the HIV Glycan Shield," Science, vol. 334, No. 6059, pp. 1097-1103 (2011).
Pejchal et al, "Structure and Function of Broadly Reactive Antibody PG16 Reveal an H3 Subdomain that Mediates Potent Neutralization of HIV-1," Proceedings of the National Academy of Sciences of the United States of America, vol. 107, No. 25, pp. 11483-11488 (2010).
Plotkin et al, "Postscript Relating to New Allegations Made by Edward Hooper at The Royal Society Discussion Meeting on Sep. 11, 2000," Philosophical Transactions of the Royal Society of London B: Biological Sciences, vol. 356, No. 1410, pp. 825-829 (2001).
Plotkin, "Correlates of Protection Induced by Vaccination," Clinical and Vaccine Immunology, vol. 17, No. 7, pp. 1055-1065 (Jul. 2010).
Plotkin, "Immunologic Correlates of Protection Induced by Vaccination," Pediatric Infectious Disease Journal, vol. 20, No. 1, pp. 63-75 (2001).
Plotkin, "The RV144 Thai HIV Vaccine Trial," Human Vaccines, vol. 6, No. 2, p. 159 (Feb. 2010).
Saphire et al, "Crystal Structure of a Neutralizing Human IgG Against HIV-1: A Template for Vaccine Design," Science, vol. 293, No. 5532, pp. 1155-1159 (2001).
Scheid et al, "Sequence and Structural Convergence of Broad and Potent HIV Antibodies That Mimic CD4 Binding," Science, vol. 333, pp. 1633-1637 (2011).
Seaman et al, "Multiclade Human Immunodeficiency Virus Type 1 Envelope Immunogens Elicit Broad Cellular and Humoral Immunity in Rhesus Monkeys," Journal of Virology, vol. 79, No. 5, pp. 2956-2963 (2005).
Seaman et al, "Standardized Assessment of NAb Responses Elicited in Rhesus Monkeys Immunized with Single- or Multi-Clade HIV-1 Envelope Immunogens," Virology, vol. 367, pp. 175-186 (2007).
Simek et al, "Human Immunodeficiency Virus Type 1 Elite Neutralizers: Individuals With Broad and Potent Neutralizing Activity Identified by Using a High-Throughput Neutralization Assay Together With an Analytical Selection Algorithm," Journal of Virology, vol. 83, No. 14, pp. 7337-7748 (2009).
Sok et al, "Promiscuous Glycan Site Recognition by Antibodies to the High-Mannose Patch of gp120 Broadens Neutralization of HIV," Science Translational Medicine, vol. 6, No. 236, pp. 236ra63 (May 14, 2014).
Stamatatos et al, "Neutralizing Antibodies Generated During Natural HIV-1 Infection: Good News for an HIV-1 Vaccine?," Nature Medicine, vol. 15, No. 8, pp. 866-870 (2009).
Vaine et al, "Antibody Responses Elicited through Homologous or Heterologous Prime-Boost DNA and Protein Vaccinations Differ in Functional Activity and Avidity," Vaccine, vol. 28, No. 17, pp. 2999-3007 (2010).
Vaine et al, "Profiles of Human Serum Antibody Responses Elicited by Three Leading HIV Vaccines Focusing on the Induction of Env-Specific Antibodies," PLoS One, vol. 5, No. 11, pp. e13916 (Nov. 2010).
Walker et al, "Broad Neutralization Coverage of HIV by Multiple Highly Potent Antibodies," Nature, vol. 477, No. 7365, pp. 466-470 (Sep. 22, 2011).
Wang et al, "Cross-Subtype Antibody and Cellular Immune Responses Induced by a Polyvalent DNA Prime-Protein Boost HIV-1 Vaccine in Healthy Human Volunteers," Vaccine, vol. 26, No. 31, pp. 3947-3957 (Jul. 23, 2008).
Wang et al, "Enhanced Immunogenicity of gp120 Protein when Combined with Recombinant DNA Priming to Generate Antibodies that Neutralize the JR-FL Primary Isolate of Human Immunodeficiency Virus Type 1," Journal of Virology, vol. 79, No. 12, pp. 7933-7937 (Jun. 2005).
Wang et al, "Polyvalent HIV-1 Env Vaccine Formulations Delivered by the DNA Priming Plus Protein Boosting Approach are Effective in Generating Neutralizing Antibodies Against Primary Human Immunodeficiency Virus Type 1 Isolates from Subtypes A, B, C, D and E," Virology, vol. 350, No. 1, pp. 34-47 (2006).
Wattanapitayakul et al, "Recent Developments in Gene Therapy for Cardiac Disease," Biomed & Pharmacother, vol. 54, No. 1, pp. 487-504 (2000).
Wiznerowicz et al, "Harnessing HIV for Therapy, Basic Research and Biotechnology," TRENDS in Biotechnology, vol. 23, No. 1, pp. 42-47 (Jan. 2005).

\* cited by examiner

COMPOSITIONS AND METHODS FOR INDUCING PROTECTIVE IMMUNITY AGAINST HUMAN IMMUNODEFICIENCY VIRUS INFECTION

CROSS REFERENCE TO RELATED APPLICATIONS

This application is a continuation of U.S. patent application Ser. No. 15/968,834, filed May 2, 2018, which is a divisional of U.S. patent application Ser. No. 14/863,808, filed Sep. 24, 2015, now U.S. Pat. No. 10,137,191, issued on Nov. 27, 2018, which is entitled to priority pursuant to 35 U.S.C. § 119(e) to U.S. Provisional Patent Application No. 62/056,059, filed Sep. 26, 2014, the disclosures of which are incorporated by reference herein in their entireties.

STATEMENT REGARDING FEDERALLY SPONSORED RESEARCH OR DEVELOPMENT

This invention was made with government support under Grant Nos. AI078526 and AI096040 awarded by the National Institutes of Health. The government has certain rights in the invention.

REFERENCE TO SEQUENCE LISTING SUBMITTED ELECTRONICALLY

This application contains a sequence listing, which is submitted electronically via EFS-Web as an ASCII formatted sequence listing with a file name "688097-53U3_Sequence Listing", creation date of Sep. 19, 2019, and having a size of 47 kB. The sequence listing submitted via EFS-Web is part of the specification and is herein incorporated by reference in its entirety.

FIELD OF THE INVENTION

This invention relates to compositions, vaccines and methods for inducing protective immunity against human immunodeficiency virus (HIV) infection. In particular, the invention relates to heterologous vaccine combinations of one or more viral expression vectors and an isolated antigenic polypeptide for inducing protective immunity against infections by one or more clades of HIV.

BACKGROUND OF THE INVENTION

Human Immunodeficiency Virus (HIV) affects millions of people worldwide, and the prevention of HIV remains a very high priority, even in an era of widespread antiretroviral treatment. In the United States, the Center for Disease Control (CDC) estimates that of all HIV-positive US residents, approximately one fifth are unaware of their status, and this small proportion is responsible for transmitting half the new infections each year [2]. Worldwide, the gap in prompt diagnosis and treatment is far greater. At the end of 2010, an estimated 34 million people were living with HIV worldwide, up 17% from 2001. Although the majority of new HIV infections continue to occur in sub-Saharan Africa, the CDC estimated that the annual incidence of HIV infection from 2008-2011 in the United States has remained stable at around 15-16/100,000, with over 40,000 new infections each year. Thus, it is an urgent global health priority to find a safe and potent HIV vaccine that would prevent HIV infection or blunt its initial impact prior to diagnosis, including both destruction of the gut CD4 pool [3] and high risk of transmission [4].

A fully efficacious vaccine is anticipated to be able to elicit both potent cellular responses and broadly neutralizing antibodies capable of neutralizing HIV-1 variants from different clades.

Moreover, a recent clinical study indicates that non-neutralizing Env-specific antibodies may have some protective capacity that is linked to subtype-specific antibody function [9]. Broadly neutralizing antibodies are directed against highly conserved regions in the viral envelope. Until recently, most anti-HIV vaccines used purified HIV antigenic proteins, such as gp160, gp41 or gp120 presented in a soluble form. Most envelope (Env) protein-based immunogens are monomeric envelope molecules that elicit binding antibodies, but not potent neutralizing antibodies. This is in part due to the fact that neutralizing antibodies recognize tertiary and quaternary epitopes on the native, trimeric structure of the viral envelope proteins. In addition, most monomeric Env-based immunogens do not induce a cell-mediated response. It was reported that stabilized trimers of HIV-1 Env induced broadly neutralizing antisera against HIV-1 in vivo. See, e.g., US 2012/0045472.

Live attenuated vaccines have proven to be highly efficacious in humans and in non-human primates (NHP) against certain viral diseases, such as a live attenuated simian immunodeficiency virus (SIV) based vaccine for preventing SIV infection. Unfortunately, due to safety risks associated with live attenuated HIV, such a strategy is not applicable for HIV human vaccine.

In order to elicit both potent cellular responses and broadly neutralizing antibodies, recombinant vectors have been used to express genes for HIV antigenic proteins in vivo as an alternative to live attenuated viral vaccines. The use of replication incompetent recombinant viral vectors has been explored for vaccines and other types of gene therapy. In particular, replication incompetent recombinant adenoviral vectors, particularly adenovirus serotypes 2 and 5 (Ad2 and Ad5) have been extensively studied for gene delivery applications, including vaccination. Although such replication incompetent Ad5 vector-based vaccines have been shown to elicit protective immune responses in a variety of animal models, the utility of recombinant Ad5 vector-based vaccines for HIV and other pathogens can be limited by the high seroprevalence of Ad5-specific neutralizing antibodies (NAbs) in human populations [17]. For example, in a seroepidemiology study of 4,381 subjects worldwide, it was observed that Ad5 NAb titers were nearly universal and high titer in sub-Saharan Africa, with the majority of individuals exhibiting Ad5 NAb titers >200 [14].

Several HIV-1 vaccine efficacy trials have been conducted using vaccines based on recombinant Ad5 vector-based vaccines. These studies include the HVTN 502/STEP (Merck Ad5), HVTN 503/Phambili (Merck Ad5), and HVTN 505 (NIH VRC DNA/Ad5) HIV-1 vaccine efficacy trials. However, all three of these HIV-1 vaccine efficacy studies, which utilized nonreplicating Ad5 and DNA/Ad5 vaccines, showed no efficacy against HIV-1 infection. Moreover, a trend towards increased HIV-1 infection was observed in subjects vaccinated with the Merck Ad5 vaccine from the STEP study as compared with placebo. Experience to date with replication incompetent vectors such as adenovirus subtype 5 for HIV vaccine has been disappointing, with failure to show benefit in several efficacy trials [5-8].

Concerns regarding the safety of Ad5 vectors, particularly from the STEP study [8, 10], have led to the exploration of biologically substantially different Ad vectors from alternative serotypes as viral vaccine vectors [11-13]. One example of an alternative adenovirus serotype to Ad5 is Adenovirus serotype 26 (Ad26). Ad26 is a relatively uncommon virus in humans, and is not known to replicate in any other species. A number of surveys for adenovirus in different populations have shown it to be isolated only rarely, and even when isolated, seldom associated with symptoms. Experimental immunization, likewise, showed little evidence for serious infection. See, e.g., references [14], and [27]-[43]. Thus, there is no evidence from observational studies that Ad26 causes clinical symptoms in healthy adults, and experimental data from an Ad26 challenge study also suggested that enteric Ad26 infection does not produce symptoms [44]. Replication-defective adenovirus vectors, rAd26, can be grown to high titers in Ad5 E1-complementing cell lines suitable for manufacturing these vectors at a large scale and at clinical grade [11], and this vector has been shown to induce humoral and cell-mediated immune responses in prime-boost vaccine strategies [11, 21]. Another alternative is rAd35, a replication-defective adenovirus vector derived from Adenovirus serotype 35. The rAd35 vectors grow to high titers on cell lines suitable for production of clinical-grade vaccines [61], and have been formulated for injection as well as stable inhalable powder [62].

These alternative adenovirus vectors show efficient transduction of human dendritic cells [63, 22], and thus have the capability to mediate high level antigen delivery and presentation.

In terms of at least receptor usage, in vivo tropism, interactions with dendritic cells, innate immune profiles, adaptive immune phenotypes, and protective efficacy against SIV in rhesus monkeys, Ad26 has proven to be biologically very different from Ad5 [11, 12, 15, 19-22]. Moreover, the safety and immunogenicity of nonreplicating Ad26 vector in humans have been demonstrated (ClinicalTrials.Gov NCT01215149). Furthermore, many of the advantageous biological differences between Ad5 and Ad26, such as lower seroprevalance and low neutralizing antibody titers in humans are also present between Ad5 and Ad35.

Modified Vaccinia Ankara (MVA) virus, a replication-deficient strain of vaccinia virus, has also been used as a viral vector for recombinant expression of HIV antigenic proteins. See, e.g., US20110159036, U.S. Pat. No. 8,197,825, etc. MVA is related to Vaccinia virus, a member of the genera Orthopoxvirus in the family of Poxviridae. Poxviruses are known to be good inducers of CD8 T cell responses because of their intracytoplasmic expression. However, they are generally believed to be poor at generating CD4 MHC class II restricted T cells. See, e.g., [64].

One possible drawback of replication-incompetent viral vectors is that expression of the target gene to be delivered to the host from the viral vector can decrease following administration of the vector. Being unable to replicate or propagate in the host, the viral vector cannot produce any new copies that can subsequently be used to augment gene expression, thus requiring re-administration of the viral vector. If the same adenovirus serotype is re-administered to the host, the host can generate neutralizing antibodies to that particular adenovirus serotype, resulting in a serotype specific anti-adenovirus response. Such a serotype specific anti-adenovirus response can prevent effective re-administration of the viral vector, rendering it less effective as a vaccine or gene delivery vehicle.

Accordingly, there is a need in the art for improved vaccines that can be used to induce a protective immunity against HIV infection. Such a vaccine preferably would be simple to administer, long-acting, and have minimal adverse effects. It further would preferably be effective against a wide diversity of circulating types of HIV transmission, including the most frequent for multiple regions of the world.

BRIEF SUMMARY OF THE INVENTION

The invention is based in part on the discovery that combinations of an isolated HIV antigenic protein with expression vectors, such as replication incompetent viral vectors, encoding HIV antigens, induce increased protective immunity against one or more clades of HIV.

Accordingly, one general aspect of the invention relates to a vaccine combination for inducing an immune response against a human immunodeficiency virus (HIV) in a subject in need thereof, comprising:

(i) a first composition comprising an immunogenically effective amount of one or more expression vectors encoding one or more HIV antigenic polypeptides and a pharmaceutically acceptable carrier;

(ii) a second composition comprising an immunogenically effective amount of an isolated antigenic polypeptide and a pharmaceutically acceptable carrier; and (iii) an immunogenically effective amount of one or more additional expression vectors encoding one or more additional antigenic polypeptides, wherein one of the first and the second compositions is for priming immunization and the other composition is for boosting immunization, and the immunogenically effective amount of the additional expression vectors is present in the second composition or in a third composition to be administered together with the second composition for priming or boosting immunization.

In an embodiment of the invention, the isolated antigenic polypeptide of the vaccine combination comprises an HIV envelope glycoprotein, and preferably a stabilized trimer of HIV gp140. In particular embodiments of the invention, the isolated antigenic polypeptide comprises the amino acid sequence of SEQ ID NO: 5 or SEQ ID NO: 6.

In an embodiment of the invention, the one or more expression vectors and the one or more additional expression vectors of the vaccine combination are adenovirus vectors, such as rAd26, rAd35, rAd48, rAd5HVR48 vectors, or MVA vectors. In a particular embodiment of the invention, the one or more additional expression vectors is present in the third composition of the vaccine combination.

In particular embodiments of the invention, the one or more antigenic polypeptides encoded by the one or more expression vectors and/or the one or more additional expression vectors comprise one or more HIV mosaic antigens, more preferably, one or more mosaic HIV Gag-Pol-Env antigens, and more preferably comprise the amino acid sequences selected from the group consisting of SEQ ID NOs: 1-4. In other particular embodiments of the invention the one or more expression vectors are rAd26 vectors encoding one or more HIV antigenic polypeptides comprising the amino acid sequences selected from the group consisting of SEQ ID NOs: 1-4, and the one or more additional expression vectors are MVA vectors encoding one or more HIV antigenic polypeptides comprising the amino acid sequences selected from the group consisting of SEQ ID NOs: 1-4.

In a preferred embodiment of the invention, a vaccine combination comprises a first composition comprising an immunogenically effective amount of rAd26 vectors encoding three HIV antigenic polypeptides having the amino acid sequences of SEQ ID NO: 1, SEQ ID NO: 3, and SEQ ID NO: 4, respectively, and a pharmaceutically acceptable carrier; a second composition comprising an immunogenically effective amount of an isolated antigenic polypeptide comprising a stabilized trimer of HIV gp140 having the amino acid sequence of SEQ ID NO: 5, and a pharmaceutically acceptable carrier; and a third composition comprising an immunogenically effective amount of MVA vectors encoding four HIV antigenic polypeptides having the amino acid sequences of SEQ ID NO: 1, SEQ ID NO: 2, SEQ ID NO: 3, and SEQ ID NO: 4.

Another general aspect of the invention relates to a vaccine combination according to an embodiment of the invention for use in generating a protective immune response against a human immunodeficiency virus (HIV) infection, wherein the first composition is used for priming the immune response, and the second composition and the immunogenically effective amount of the one or more additional expression vectors are used for boosting the immune response.

Another general aspect of the invention relates to a kit comprising a vaccine combination according to an embodiment of the invention.

Yet another general aspect of the invention relates to a method of inducing an immune response against a human immunodeficiency virus (HIV) in a subject in need thereof, the method comprising:

(i) administering to the subject a first composition comprising an immunogenically effective amount of one or more expression vectors encoding one or more HIV antigenic polypeptides and a pharmaceutically acceptable carrier;

(ii) administering to the subject a second composition comprising an immunogenically effective amount of an isolated antigenic polypeptide and a pharmaceutically acceptable carrier; and (iii) administering to the subject an immunogenically effective amount of one or more additional expression vectors encoding one or more additional HIV antigenic polypeptides, wherein steps (i) and (ii) are conducted in either order, with one of the steps for priming immunization and the other for boosting immunization, and the immunogenically effective amount of the one or more additional expression vectors is present in the second composition or in a third composition administered together with the second composition for the priming or the boosting immunization.

In an embodiment of the invention, the first composition is for the priming immunization, and the second composition and the immunogenically effective amount of the one or more additional expression vectors are for the boosting immunization.

In another embodiment of the invention, the one or more additional expression vectors is present in a third composition.

A further general aspect of the invention relates to a method of inducing an immune response against a human immunodeficiency virus (HIV) in a subject in need thereof, the method comprising:

(i) administering to the subject a primer vaccine comprising an immunogenically effective amount of one or more expression vectors encoding one or more HIV antigenic polypeptides and a pharmaceutically acceptable carrier; and (ii) administering to the subject a booster vaccine comprising an immunogenically effective amount of an isolated antigenic polypeptide, an immunogenically effective amount of one or more additional expression vectors encoding one or more additional HIV antigenic polypeptides, and a pharmaceutically acceptable carrier;

wherein the isolated antigenic polypeptide and the one or more additional expression vectors are present in the same composition or separate compositions; and wherein the booster vaccine is administered after the primer vaccine is administered.

In a preferred embodiment of the invention, one or both of the primer vaccine and the booster vaccine are re-administered once or multiple times to further induce the immune response, wherein the primer vaccine is re-administered after its initial administration but before the booster vaccine is first administered.

In a preferred embodiment of the invention, the isolated antigenic protein is an HIV envelope glycoprotein, more preferably, a stabilized HIV envelope glycoprotein, such as a stabilized HIV gp140 trimeric protein or a stabilized mosaic gp140 trimeric protein, and yet more preferably, comprises the amino acid sequence of SEQ ID NO: 5 or SEQ ID NO: 6.

In another preferred embodiment of the invention, the one or more expression vectors and/or the one or more additional expression vectors encode one or more HIV mosaic antigens, more preferably, one or more mosaic HIV Gag-Pol-Env antigens, and yet more preferably encode one or more mosaic HIV Gag-Pol-Env antigens comprising the amino acid sequences selected from the group consisting of SEQ ID NOs: 1-4.

In yet another preferred embodiment of the invention, the one or more expression vectors or additional expression vectors are adenovirus vectors, such as rAd26, rAd35, rAd48, rAd5HVR48 vectors, or MVA vectors. More preferably, the one or more vectors used for priming immunization are derived from a different type of virus than those used for boosting immunization. For example, when adenovirus vectors, such as rAd26 or rAd35 vectors, are used for the priming immunization, MVA vectors are used together with the isolated HIV antigenic protein for the boosting immunization.

In one embodiment of the invention, the one or more expression vectors are rAd26 vectors and the one or more additional expression vectors are MVA vectors. In another embodiment, the one or more expression vectors are MVA vectors and the one or more additional expression vectors are rAd26 vectors. In yet another embodiment, the one or more expression vectors are rAd26 vectors and the one or more additional expression vectors are also rAd26 vectors.

In one particular embodiment of the invention, the composition used for the priming immunization comprises rAd26 vectors encoding one or more antigenic proteins comprising the amino acid sequences of SEQ ID NOs: 1, 3 and 4, respectively; and the one or more compositions used for the boosting immunization comprise an isolated protein comprising the amino acid sequence of SEQ ID NO: 5 or SEQ ID NO: 6, and MVA vectors encoding one or more antigenic proteins having the amino acid sequences of SEQ ID NOs: 1-4, respectively. Most preferably, the MVA vectors are present in a third composition.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

In the drawings:

FIG. 1A: Glade C gp140 Env and mosaic Env ELISA titers at week 28; FIG. 1B: Glade C gp140 Env and mosaic Env ELISA titers at week 56;

DETAILED DESCRIPTION OF THE INVENTION

Figure 1A:
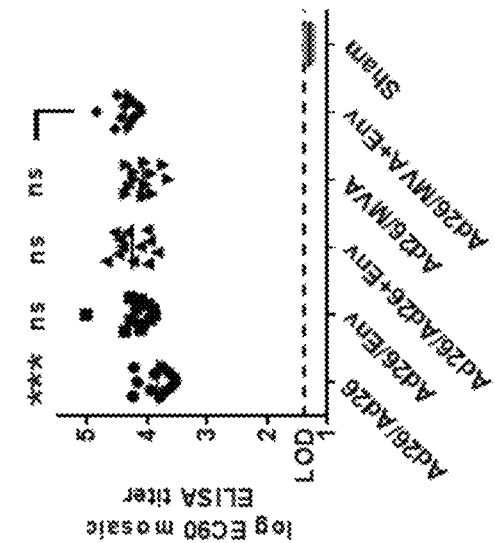
FIGS. 1A and 1B show the results from a Glade C gp140 envelope (Env) protein and mosaic envelope (Env) protein Enzyme-Linked Immunosorbent Assay (ELISA) on serum samples taken from Rhesus monkeys (*Macaca mulatta*) (NHPs) vaccinated with different vaccine combinations at weeks 28 and 56 after the initial administration of the primer vaccine; $\log_{10}$-transformed $EC_{90}$ ELISA titers are shown, and the symbols represent the titers from the individual animals tested; horizontal lines indicate group geometric mean titers and dotted lines represent lower limits of detection.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein.

It must be noted that as used herein and in the appended claims, the singular forms "a," "an," and "the" include plural reference unless the context clearly dictates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising", "containing", "including", and "having", whenever used herein in the context of an aspect or embodiment of the invention can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, "subject" means any animal, preferably a mammal, most preferably a human, to whom will be or has been treated by a method according to an embodiment of the invention. The term "mammal" as used herein, encompasses any mammal. Examples of mammals include, but are not limited to, cows, horses, sheep, pigs, cats, dogs, mice, rats, rabbits, guinea pigs, non-human primates (NHPs) such as monkeys or apes, humans, etc., more preferably a human.

As used herein, the term "protective immunity" or "protective immune response" means that the vaccinated subject is able to control an infection with the pathogenic agent against which the vaccination was done. Usually, the subject having developed a "protective immune response" develops only mild to moderate clinical symptoms or no symptoms at all. Usually, a subject having a "protective immune response" or "protective immunity" against a certain agent will not die as a result of the infection with said agent.

An "adenovirus capsid protein" refers to a protein on the capsid of an adenovirus (e.g., Ad26, Ad35, rAd48, rAd5HVR48 vectors) that is involved in determining the serotype and/or tropism of a particular adenovirus. Adenoviral capsid proteins typically include the fiber, penton and/or hexon proteins. As used herein a "capsid protein" for a particular adenovirus, such as an "Ad26 capsid protein" or an "Ad35 capsid protein" can be, for example, a chimeric capsid protein that includes at least a part of an Ad26 or Ad35 capsid protein. In certain embodiments, the capsid protein is an entire capsid protein of Ad26 or of Ad35. In certain embodiments, the hexon, penton and fiber are of Ad26 or of Ad35.

As used herein, the term "co-delivery" or "administered together with" refers to simultaneous administration of two components, such as a viral expression vector and an isolated antigenic polypeptide. "Simultaneous administration" can be administration of the two components at least within the same day. When two components are "administered together with," they can be administered in separate compositions sequentially within a short time period, such as 24, 20, 16, 12, 8 or 4 hours, or within 1 hour, or they can be administered in a single composition at the same time.

The terms "adjuvant" and "immune stimulant" are used interchangeably herein, and are defined as one or more substances that cause stimulation of the immune system. In this context, an adjuvant is used to enhance an immune response to the expression vectors and antigenic polypeptides of the invention, such as adenovirus vectors, MVA vectors, and/or HIV antigenic polypeptides of the invention.

As used herein, the term "infection" refers to the invasion of a host by a disease causing agent. A disease causing agent is considered to be "infectious" when it is capable of invading a host, and replicating or propagating within the host. Examples of infectious agents include viruses, e.g., human immunodeficiency virus (HIV) and certain species of adenovirus, prions, bacteria, fungi, protozoa and the like.

Human immunodeficiency virus (HIV) is a member of the genus *Lentivirinae*, which is part of the family of Retroviridae. Two species of HIV infect humans: HIV-1 and HIV-2. HIV-1 is the most common strain of HIV virus, and is known to be more pathogenic than HIV-2. As used herein, the terms "human immunodeficiency virus" and "HIV" refer, but are not limited to, HIV-1 and HIV-2. In certain exemplary embodiments, the envelope proteins described herein refer to those present on any of the five serogroups of lentiviruses that are recognized: primate (e.g., HIV-1, HIV-2, simian immunodeficiency virus (SIV)); sheep and goat (e.g., visna virus, caprine arthritis encephalitis virus); horse (equine infectious anemia virus); cat (e.g., feline immunodeficiency virus (FIV)); and cattle (e.g., bovine immunodeficiency virus (BIV)) (See International Committee on Taxonomy of Viruses descriptions).

HIV is categorized into multiple clades with a high degree of genetic divergence. As used herein, the term "HIV Glade" or "HIV subtype" refers to related human immunodeficiency viruses classified according to their degree of genetic similarity. There are currently three groups of HIV-1 isolates: M, N and O. Group M (major strains) consists of at least ten clades, A through J. Group O (outer strains) can consist of a similar number of clades. Group N is a new HIV-1 isolate that has not been categorized in either group M or O. In certain exemplary embodiments, a broadly neutralizing antibody described herein will recognize and raise an immune response against two, three, four, five, six, seven, eight, nine, ten or more clades and/or two or more groups of HIV.

It is discovered in the invention that heterologous prime-boost combinations, in particular, priming with an expression vector, such as rAd26, encoding one or more HIV antigenic proteins, followed by boosting with an isolated HIV antigenic protein, such as an HIV envelope glycoprotein, and preferably further boosting with rAd26 or MVA encoding one or more HIV antigenic proteins, are surprisingly effective in generating protective immune responses against one or more subtypes of HIV.

HIV Antigenic Proteins

As used herein, the term "antigenic polypeptide of an HIV," "HIV antigenic polypeptide," "HIV antigenic protein," "HIV immunogenic polypeptide," or "HIV immunogen" refers to a polypeptide capable of inducing an immune response, e.g., a humoral and/or cellular mediated response, against the HIV in a subject in need thereof. The antigenic polypeptide can be a protein of the HIV, a fragment or epitope thereof, or a combination of multiple HIV proteins or portions thereof, that can induce an immune response or produce an immunity, e.g., protective immunity, against the HIV in a subject in need thereof.

Preferably, an antigenic polypeptide is capable of raising in a host a protective immune response, e.g., inducing an immune response against a viral disease or infection, and/or producing an immunity in (i.e., vaccinates) a subject against a viral disease or infection, that protects the subject against the viral disease or infection. For example, the antigenic polypeptide can comprise a protein or fragments thereof from Simian Immunodeficiency Virus (SIV) or an HIV, such as the HIV or SIV envelope gp160 protein, the HIV or SIV matrix/capsid proteins, and the HIV or SIV gag, pol and env gene products.

According to embodiments of the invention, the antigenic polypeptide can be an HIV-1 or HIV-2 antigen or fragments thereof. Examples of HIV antigens include, but are not limited to gag, pol, and env gene products, which encode structural proteins and essential enzymes. Gag, pol, and env gene products are synthesized as polyproteins, which are further processed into multiple other protein products. The primary protein product of the gag gene is the viral structural protein gag polyprotein, which is further processed into MA, CA, SP1, NC, SP2, and P6 protein products. The pol gene encodes viral enzymes (Pol, polymerase), and the primary protein product is further processed into RT, RNase H, IN, and PR protein products. The env gene encodes structural proteins, specifically glycoproteins of the virion envelope. The primary protein product of the env gene is gp160, which is further processed into gp120 and gp41. Other examples of HIV antigens include gene regulatory proteins Tat and Rev; accessory proteins Nef, Vpr, Vif and Vpu; capsid proteins, nucleocapsid proteins, and p24 viral protein. A heterologous nucleic acid sequence according to the invention can encode any HIV antigen, and preferably encodes a gag, env, and/or pol gene product, or portion thereof.

According to a preferred embodiment, the antigenic polypeptide comprises an HIV Gag, Env, or Pol antigen, or any portion or combination thereof, more preferably an HIV-1 Gag, Env, or Pol antigen or any portion or combination thereof.

According to another preferred embodiment, the antigenic polypeptide or a peptide encoded by a vector according to the invention is a mosaic HIV antigen. As used herein, "mosaic antigen" refers to a recombinant protein assembled from fragments of natural sequences. The "mosaic antigen" can be computationally generated and optimized using a genetic algorithm. Mosaic antigens resemble natural antigens, but are optimized to maximize the coverage of potential T-cell epitopes found in the natural sequences, which improves the breadth and coverage of the immune response.

A mosaic HIV antigen according to the invention is preferably a mosaic Gag-Pol-Env antigen, and more preferably a mosaic HIV-1 Gag-Pol-Env antigen. As used herein, "a mosaic HIV Gag-Pol-Env antigen" specifically refers to a mosaic antigen comprising multiple epitopes derived from one or more of the Gag, Pol and Env polyprotein sequences of HIV. The epitope sequences of the mosaic HIV Gag-Pol-Env antigens according to the invention resemble the sequences of the natural HIV antigens, but are optimized to present a broader possible array of T cell epitopes to improve coverage of epitopes found in circulating HIV sequences.

For example, to provide maximal coverage of potential T-cell epitopes, mosaic Gag, Pol and Env antigens are designed to provide optimal coverage of one or more HIV clades. Sequence Database in silico recombinant sequences of fragments of 9 contiguous amino acids (9-mers) are selected that resemble real proteins and that maximize the number of 9-mer sequence matches between vaccine candidates and the global database. The mosaic Gag, Pol and Env antigens have similar domain structure to natural antigens and consist entirely of natural sequences with no artificial junctions. The Pol antigens can contain mutants to eliminate catalytic activity. The monomeric Env gp140 mosaic antigens can contain point mutations to eliminate cleavage and fusion activity.

In one embodiment, a mosaic HIV Gag-Pol-Env antigen according to the invention is a mosaic HIV Gag antigen with epitopes derived from the sequences of gag gene products; a mosaic HIV Pol antigen with epitopes derived from the sequences of pol gene products; or a mosaic HIV Env antigen with epitopes derived from the sequences of env gene products.

In another embodiment, a mosaic HIV Gag-Pol-Env antigen according to the invention comprises a combination of epitopes derived from sequences of gag, pol, and/or env gene products. Illustrative and non-limiting examples include mosaic Env-Pol antigens with epitopes derived from the sequences of env and pol gene products; mosaic Env-Gag antigens with epitopes derived from the sequences of env and gag gene products; mosaic Gag-Pol antigens with epitopes derived from the sequences of gag and pol gene products; and mosaic Gag-Env antigens with epitopes derived from the sequences of gag and env gene products.

In yet another embodiment, a mosaic HIV Gag-Pol-Env antigen according to the invention comprises a combination of epitopes derived from sequences of gag, pol, and env gene products from one or more clades.

Examples of mosaic HIV Gag-Pol-Env antigens include those described in, e.g., US20120076812, Barouch et al., *Nat Med* 2010, 16:319-323 [54]; Barouch et al., *Cell* 155: 1-9, 2013 [65], all of which are incorporated herein by reference in their entirety.

Preferably, mosaic HIV Gag-Pol-Env antigens include, but are not limited to, antigens comprising the amino acid sequences selected from the group consisting of SEQ ID NOs: 1-4.

In view of the present disclosure, a mosaic HIV antigen can be produced using methods known in the art. See, for example, US20120076812, Fischer et al., *Nat Med,* 2007. 13(1): p. 100-6 [53]; Barouch et al., *Nat Med* 2010, 16:319-323 [54], all of which are incorporated herein by reference in their entirety.

Envelope Glycoprotein

As used herein, each of the terms "envelope glycoprotein," "env glycoprotein," and "Env" refers to, but is not limited to, the glycoprotein that is expressed on the surface of the envelope of HIV virions and the surface of the plasma membrane of HIV infected cells, or a fragment thereof that can induce an immune response or produce an immunity against the HIV in a subject in need thereof.

The env gene encodes gp160, which is proteolytically cleaved into gp120 and gp41. More specifically, gp160 trimerizes to (gp160)3 and then undergoes cleavage into the two noncovalently associated fragments gp120 and gp41. Viral entry is subsequently mediated by a trimer of gp120/gp41 heterodimers. Gp120 is the receptor binding fragment, and binds to the CD4 receptor on a target cell that has such a receptor, such as, e.g., a T-helper cell. Gp41, which is non-covalently bound to gp120, is the fusion fragment and provides the second step by which HIV enters the cell. Gp41 is originally buried within the viral envelope, but when gp120 binds to a CD4 receptor, gp120 changes its conformation causing gp41 to become exposed, where it can assist in fusion with the host cell. Gp140 is the uncleaved ectodomain of trimeric gp160, i.e., $(gp160)_3$, that has been used as a surrogate for the native state of the cleaved, viral spike.

According to one embodiment of the invention, env glycoproteins (e.g., gp160, gp140, gp120, or gp41), preferably stabilized trimeric gp140 protein, can be administered for priming or boosting immunizations to enhance the immunity induced by expression vectors alone.

As used herein, each of the terms "stabilized trimeric gp140 protein" and "stabilized trimer of gp140" refers to a trimer of gp140 polypeptides that includes a polypeptide sequence that increases the stability of the trimeric structure. The gp140 polypeptides can have, or can be modified to include a trimerization domain that stabilizes trimers of gp140. Examples of trimerization domains include, but are not limited to, the T4-fibritin "foldon" trimerization domain; the coiled-coil trimerization domain derived from GCN4 [66]; and the catalytic subunit of *E. coli* aspartate transcarbamoylase as a trimer tag [67].

In a particular embodiment of the invention, a stabilized trimeric gp140 protein comprises the amino acid sequence of SEQ ID NO: 5.

According to one embodiment of the invention, a stabilized trimeric gp140 protein can be administered as a boosting immunization or as a component of a boosting immunization together with viral expression vectors. Preferably, the stabilized trimeric gp140 protein is a Glade C or Glade A gp140 protein, and more preferably a Glade C gp140 protein. A Glade C trimeric gp140 protein is able to induce potent neutralizing antibody responses against a set of HIV-1 variants from different clades and with different neutralization sensitivities in guinea pigs [68, 60].

According to another embodiment of the invention, the "envelope glycoprotein" is a mosaic envelope protein comprising multiple epitopes derived from one or more of Env polyprotein sequences of one or more HIV clades. For example, as used herein a "gp140 protein" can be a "mosaic gp140 protein" that contains multiple epitopes derived from one or more gp140 protein sequences of one or more HIV clades.

In a particular embodiment of the invention, a mosaic gp140 protein is a stabilized trimer of mosaic gp140 comprising the amino acid sequence of SEQ ID NO: 6.

An isolated gp140 protein can be co-delivered with an adenovirus expression vector or MVA expression vector. According to a preferred embodiment, a gp140 protein and Ad26 or MVA vector are administered separately, as two distinct formulations, or together in a single formulation. Simultaneous administration or co-delivery can take place at the same time, within one hour, or within the same day. Furthermore, a gp140 protein can be administered in an adjuvanted formulation. Suitable adjuvants can be, for example, aluminum phosphate or a saponin-based adjuvant.

Antigenic polypeptides can be produced and isolated using any method known in the art in view of the present disclosure. For example, an antigenic polypeptide can be expressed from a host cell, preferably a recombinant host cell optimized for production of the antigenic polypeptide. According to an embodiment of the invention, a recombinant gene is used to express a gp140 protein containing mutations to eliminate cleavage and fusion activity, preferably an optimized gp140 protein with increased breadth, intensity, depth, or longevity of the antiviral immune response (e.g., cellular or humoral immune responses) generated upon immunization (e.g., when incorporated into a composition of the invention, e.g., vaccine of the invention) of a subject (e.g., a human). The optimized gp140 protein can also include cleavage site mutation(s), a factor Xa site, and/or a foldon trimerization domain. A leader/signal sequence can be operably linked to the N-terminal of an optimized gp140 protein for maximal protein expression. The leader/signal sequence is usually cleaved from the nascent polypeptide during transport into the lumen of the endoplasmic reticulum. Any leader/signal sequence suitable for a host cell of interest can be used. An exemplary leader/signal sequence comprises the amino acid sequence of SEQ ID NO:7.

In a preferred embodiment of the invention, the isolated antigenic polypeptide is a stabilized trimeric gp140 as those described in Nkolola et al. 2010, *J. Virology* 84(7): 3270-3279 [68]; Kovacs et al., *PNAS* 2012, 109(30):12111-6 [60], WO 2010/042942 and WO 2014/107744, all of which are incorporated by reference in their entirety.

Adenoviruses

An adenovirus according to the invention belongs to the family of the Adenoviridae, and preferably is one that belongs to the genus *Mastadenovirus*. It can be a human adenovirus, but also an adenovirus that infects other species, including but not limited to a bovine adenovirus (e.g. bovine adenovirus 3, BAdV3), a canine adenovirus (e.g. CAdV2), a porcine adenovirus (e.g. PAdV3 or 5), or a simian adenovirus (which includes a monkey adenovirus and an ape adenovirus, such as a chimpanzee adenovirus or a gorilla adenovirus). Preferably, the adenovirus is a human adenovirus (HAdV, or AdHu), or a simian adenovirus such as chimpanzee or gorilla adenovirus (ChAd, AdCh, or SAdV). In the invention, a human adenovirus is meant if referred to as Ad without indication of species, e.g. the brief notation "Ad5" means the same as HAdV5, which is human adenovirus serotype 5. Also as used herein, the notation "rAd" means recombinant adenovirus, e.g., "rAd26" refers to recombinant human adenovirus 26.

Most advanced studies have been performed using human adenoviruses, and human adenoviruses are preferred according to certain aspects of the invention. In certain preferred embodiments, a recombinant adenovirus according to the invention is based upon a human adenovirus. In preferred embodiments, the recombinant adenovirus is based upon a human adenovirus serotype 5, 11, 26, 34, 35, 48, 49, 50, 52, etc. According to a particularly preferred embodiment of the invention, an adenovirus is a human adenovirus of one of the serotypes 26 or 35. An advantage of these serotypes is a low seroprevalence and/or low pre-existing neutralizing antibody titers in the human population. Preparation of rAd26 vectors is described, for example, in WO 2007/104792 and in Abbink et al., (2007) *Virol* 81(9): 4654-63 [11], both of which are incorporated by reference herein in their entirety. Exemplary genome sequences of Ad26 are found in GenBank Accession EF 153474 and in SEQ ID NO: 1 of WO 2007/104792. Preparation of rAd35 vectors is described, for example, in U.S. Pat. No. 7,270,811, in WO 00/70071, and in Vogels et al., (2003) *J Virol* 77(15): 8263-71 [12], all of which are incorporated by reference herein in their entirety. Exemplary genome sequences of Ad35 are found in GenBank Accession AC_000019 and in FIG. 6 of WO 00/70071.

Simian adenoviruses generally also have a low seroprevalence and/or low pre-existing neutralizing antibody titers in the human population, and a significant amount of work has been reported using chimpanzee adenovirus vectors (e.g. U.S. Pat. No. 6,083,716; WO 2005/071093; WO 2010/086189; WO 2010085984; Farina et al., 2001, *J Virol* 75: 11603-13 [13]; Cohen et al., 2002, *J Gen Virol* 83: 151-55 [69]; Kobinger et al., 2006, *Virology* 346: 394-401 [70]; Tatsis et al., 2007, *Molecular Therapy* 15: 608-17 [71]; see also review by Bangari and Mittal, 2006, *Vaccine* 24: 849-62 [72]; and review by Lasaro and Ertl, 2009, *Mol Ther* 17: 1333-39 [73]). Hence, in other preferred embodiments, the recombinant adenovirus according to the invention is based upon a simian adenovirus, e.g. a chimpanzee adenovirus. In certain embodiments, the recombinant adenovirus is based upon simian adenovirus type 1, 7, 8, 21, 22, 23, 24, 25, 26, 27.1, 28.1, 29, 30, 31.1, 32, 33, 34, 35.1, 36, 37.2, 39, 40.1, 41.1, 42.1, 43, 44, 45, 46, 48, 49, 50 or SA7P.

Preferably, the adenovirus vector is a replication deficient recombinant viral vector, such as rAd26, rAd35, rAd48, rAd5HVR48, etc.

In a preferred embodiment according to the invention the adenoviral vectors comprise capsid proteins from two rare serotypes: Ad26 and Ad35. In the typical embodiment, the vector is an rAd26 or rAd35 virus.

Thus, the vectors that can be used in an embodiment of the invention comprise an Ad26 or Ad35 capsid protein (e.g., a fiber, penton or hexon protein). One of ordinary skill in the art will recognize that it is not necessary that an entire Ad26 or Ad35 capsid protein be used in the vectors of the invention. Thus, chimeric capsid proteins that include at least a part of an Ad26 or Ad35 capsid protein can be used in the vectors of the invention. The vectors according to embodiments of the invention can also comprise capsid proteins in which the fiber, penton, and hexon proteins are each derived from a different serotype, so long as at least one capsid protein is derived from Ad26 or Ad35. In preferred embodiments, the fiber, penton and hexon proteins are each derived from Ad26 or each from Ad35.

One of ordinary skill in the art will recognize that elements derived from multiple serotypes can be combined in a single recombinant adenovirus vector. Thus, a chimeric adenovirus that combines desirable properties from different serotypes can be produced. Thus, in some embodiments, a chimeric adenovirus of the invention could combine the absence of pre-existing immunity of the Ad26 and Ad35 serotypes with characteristics such as temperature stability, assembly, anchoring, production yield, redirected or improved infection, stability of the DNA in the target cell, and the like.

In certain embodiments the recombinant adenovirus vector useful in the invention is derived mainly or entirely from Ad35 or from Ad26 (i.e., the vector is rAd35 or rAd26). In some embodiments, the adenovirus is replication deficient, e.g., because it contains a deletion in the E1 region of the genome. For the adenoviruses of the invention, being derived from Ad26 or Ad35, it is typical to exchange the E4-orf6 coding sequence of the adenovirus with the E4-orf6 of an adenovirus of human subgroup C such as Ad5. This allows propagation of such adenoviruses in well-known complementing cell lines that express the E1 genes of Ad5, such as for example 293 cells, PER.C6 cells, and the like (see, e.g. Havenga, et al., 2006, *J Gen Virol* 87: 2135-43 [61]; WO 03/104467). However, such adenoviruses will not be capable of replicating in non-complementing cells that do not express the E1 genes of Ad5.

In certain embodiments, the adenovirus is a human adenovirus of serotype 35, with a deletion in the E1 region into which the nucleic acid encoding the one or more HIV antigenic polypeptides has been cloned, and with an E4-orf6 region of AdS. In certain embodiments, the adenovirus is a human adenovirus of serotype 26, with a deletion in the E1 region into which the nucleic acid encoding the one or more HIV antigenic polypeptides has been cloned, and with an E4 orf6 region of AdS. For the Ad35 adenovirus, it is typical to retain the 3' end of the E1B 55K open reading frame in the adenovirus, for instance the 166 bp directly upstream of the pIX open reading frame or a fragment comprising this such as a 243 bp fragment directly upstream of the pIX start codon, marked at the 5' end by a Bsu36I restriction site, since this increases the stability of the adenovirus because the promoter of the pIX gene is partly residing in this area (see, e.g. [61], supra; WO 2004/001032).

The preparation of recombinant adenoviral vectors is well known in the art. Preparation of rAd26 vectors is described, for example, in WO 2007/104792 and in Abbink et al., (2007) Virol 81(9): 4654-63 [11]. Exemplary genome sequences of Ad26 are found in GenBank Accession EF 153474 and in SEQ ID NO: 1 of WO 2007/104792. Preparation of rAd35 vectors is described, for example, in U.S. Pat. No. 7,270,811 and in Vogels et al., (2003) J Virol 77(15): 8263-71 [12]. An exemplary genome sequence of Ad35 is found in GenBank Accession AC_000019.

In an embodiment of the invention, the vectors useful for the invention include those described in WO2012/082918, the disclosure of which is incorporated herein by reference in its entirety.

Typically, a vector useful in the invention is produced using a nucleic acid comprising the entire recombinant adenoviral genome (e.g., a plasmid, cosmid, or baculovirus vector). Thus, the invention also provides isolated nucleic acid molecules that encode the adenoviral vectors of the invention. The nucleic acid molecules of the invention can be in the form of RNA or in the form of DNA obtained by cloning or produced synthetically. The DNA can be double-stranded or single-stranded.

The adenovirus vectors useful in the invention are typically replication deficient. In these embodiments, the virus is rendered replication deficient by deletion or inactivation of regions critical to replication of the virus, such as the E1 region. The regions can be substantially deleted or inactivated by, for example, inserting a gene of interest, such as a gene encoding an antigenic polypeptide (usually linked to a promoter) within the region. In some embodiments, the vectors of the invention can contain deletions in other regions, such as the E2, E3 or E4 regions, or insertions of heterologous genes linked to a promoter within one or more of these regions. For E2-and/or E4-mutated adenoviruses, generally E2-and/or E4-complementing cell lines are used to generate recombinant adenoviruses. Mutations in the E3 region of the adenovirus need not be complemented by the cell line, since E3 is not required for replication.

A packaging cell line is typically used to produce sufficient amounts of adenovirus vectors for use in the invention. A packaging cell is a cell that comprises those genes that have been deleted or inactivated in a replication deficient vector, thus allowing the virus to replicate in the cell. Suitable packaging cell lines include, for example, PER.C6, 911, 293, and E1 A549.

As noted above, a wide variety of HIV antigenic polypeptides can be expressed in the vectors. If required, the heterologous gene encoding the HIV antigenic polypeptides can be codon-optimized to ensure proper expression in the treated host (e.g., human). Codon-optimization is a technology widely applied in the art. Typically, the heterologous gene is cloned into the E1 and/or the E3 region of the adenoviral genome.

The heterologous HIV gene can be under the control of (i.e., operably linked to) an adenovirus-derived promoter (e.g., the Major Late Promoter), or can be under the control of a heterologous promoter. Examples of suitable heterologous promoters include the cytomegalovirus (CMV) promoter and the Rous Sarcoma virus (RSV) promoter. Preferably, the promoter is located upstream of the heterologous gene of interest within an expression cassette.

As noted above, the adenovirus vectors useful for the invention can encode a wide variety of HIV antigenic polypeptides known to those of skill in the art, including but not limited to, the antigenic polypeptides discussed herein.

In a preferred embodiment of the invention, the adenovirus vectors are rAd26 vector, such as that described in Abbink, J Virol, 2007. 81(9): p. 4654-63 [11], which is incorporated herein by reference.

MVA Vectors

MVA vectors useful for the invention utilize attenuated virus derived from Modified Vaccinia Ankara virus, which is characterized by the loss of their capabilities to reproductively replicate in human cell lines. The MVA vectors can express any of the HIV antigenic polypeptides known to those of skill in the art, including but not limited to the antigenic polypeptides discussed herein.

MVA has been generated by more than 570 serial passages on chicken embryo fibroblasts of the dermal vaccinia strain Ankara [Chorioallantois vaccinia virus Ankara virus, CVA; for review see Mayr et al. (1975), Infection 3, 6-14 [74]] that was maintained in the Vaccination Institute, Ankara, Turkey for many years and used as the basis for vaccination of humans. However, due to the often severe post-vaccination complications associated with vaccinia viruses, there were several attempts to generate a more attenuated, safer smallpox vaccine.

During the period of 1960 to 1974, Prof. Anton Mayr succeeded in attenuating CVA by over 570 continuous passages in CEF cells [74]. It was shown in a variety of animal models that the resulting MVA was avirulent [75]. As part of the early development of MVA as a pre-smallpox vaccine, there were clinical trials using MVA-517 in combination with Lister Elstree [77, 78] in subjects at risk for adverse reactions from vaccinia. In 1976, MVA derived from MVA-571 seed stock (corresponding to the 571$^{st}$ passage) was registered in Germany as the primer vaccine in a two-stage parenteral smallpox vaccination program. Subsequently, MVA-572 was used in approximately 120,000 Caucasian individuals, the majority children between 1 and 3 years of age, with no reported severe side effects, even though many of the subjects were among the population with high risk of complications associated with vaccinia [76]. MVA-572 was deposited at the European Collection of Animal Cell Cultures as ECACC V94012707.

As a result of the passaging used to attenuate MVA, there are a number of different strains or isolates, depending on the number of passages conducted in CEF cells. For example, MVA-572 was used in a small dose as a pre-vaccine in Germany during the smallpox eradication program, and MVA-575 was extensively used as a veterinary vaccine. MVA as well as MVA-BN lacks approximately 15% (31 kb from six regions) of the genome compared with ancestral CVA virus. The deletions affect a number of virulence and host range genes, as well as the gene for Type A inclusion bodies. MVA-575 was deposited on December 7, 2000, at the European Collection of Animal Cell Cultures (ECACC) under Accession No. V00120707. The attenuated CVA-virus MVA (Modified Vaccinia Virus Ankara) was obtained by serial propagation (more than 570 passages) of the CVA on primary chicken embryo fibroblasts.

Even though Mayr et al. demonstrated during the 1970s that MVA is highly attenuated and avirulent in humans and mammals, certain investigators have reported that MVA is not fully attenuated in mammalian and human cell lines since residual replication might occur in these cells [79, 80; U.S. Pat. No. 5,185,146; 81]. It is assumed that the results reported in these publications have been obtained with various known strains of MVA, since the viruses used essentially differ in their properties, particularly in their growth behaviour in various cell lines. Such residual replication is undesirable for various reasons, including safety concerns in connection with use in humans.

Strains of MVA having enhanced safety profiles for the development of safer products, such as vaccines or pharmaceuticals, have been developed, for example by Bavarian Nordic. MVA was further passaged by Bavarian Nordic and is designated MVA-BNA. A representative sample of MVA-BN was deposited on Aug. 30, 2000 at the European Collection of Cell Cultures (ECACC) under Accession No. V00083008. MVA-BN is further described in WO 02/42480 (US 2003/0206926) and WO 03/048184 (US 2006/0159699), both of which are incorporated by reference herein in their entirety.

"Derivatives" or "variants" of MVA refer to viruses exhibiting essentially the same replication characteristics as MVA as described herein, but exhibiting differences in one or more parts of their genomes. For example, MVA-BN as well as a derivative or variant of MVA-BN fails to reproductively replicate in vivo in humans and mice, even in severely immune suppressed mice. More specifically, MVA-BN or a derivative or variant of MVA-BN has preferably also the capability of reproductive replication in chicken embryo fibroblasts (CEF), but no capability of reproductive replication in the human keratinocyte cell line HaCat [82], the human bone osteosarcoma cell line 143B (ECACC Deposit No. 91112502), the human embryo kidney cell line 293 (ECACC Deposit No. 85120602), and the human cervix adenocarcinoma cell line HeLa (ATCC Deposit No. CCL-2). Additionally, a derivative or variant of MVA-BN has a virus amplification ratio at least two fold less, more preferably three-fold less than MVA-575 in Hela cells and HaCaT cell lines. Tests and assays for these properties of MVA variants are described in WO 02/42480 (US 2003/0206926) and WO 03/048184 (US 2006/0159699).

The term "not capable of reproductive replication" or "no capability of reproductive replication" is, for example, described in WO 02/42480, which also teaches how to obtain MVA having the desired properties as mentioned above. The term applies to a virus that has a virus amplification ratio at 4 days after infection of less than 1 using the assays described in WO 02/42480 or in U.S. Pat. No. 6,761,893, both of which are incorporated by reference herein in their entirety.

The term "fails to reproductively replicate" refers to a virus that has a virus amplification ratio at 4 days after infection of less than 1. Assays described in WO 02/42480 or in U.S. Pat. No. 6,761,893 are applicable for the determination of the virus amplification ratio.

The amplification or replication of a virus is normally expressed as the ratio of virus produced from an infected cell (output) to the amount originally used to infect the cell in the first place (input), and is referred to as the "amplification ratio". An amplification ratio of "1" defines an amplification status where the amount of virus produced from the infected cells is the same as the amount initially used to infect the cells, meaning that the infected cells are permissive for virus infection and reproduction. In contrast, an amplification ratio of less than 1, i.e., a decrease in output compared to the input level, indicates a lack of reproductive replication and therefore attenuation of the virus.

The advantages of MVA-based vaccines include their safety profile as well as availability for large scale vaccine production. Furthermore, in addition to its efficacy, the feasibility of industrial scale manufacturing can be beneficial. Additionally, MVA-based vaccines can deliver multiple heterologous antigens and allow for simultaneous induction of humoral and cellular immunity.

MVA vectors useful for the invention can be prepared using methods known in the art, such as those described in WO/2002/042480, WO/2002/24224, US20110159036, U.S. Pat. No. 8,197,825, etc., the relevant disclosures of which are incorporated herein by reference.

In another aspect, replication deficient MVA viral strains can also be suitable for use in the invention, such as strains MVA-572 and MVA-575, or any other similarly attenuated MVA strain. Also suitable can be a mutant MVA, such as the deleted chorioallantois vaccinia virus Ankara (dCVA). A dCVA comprises del I, del II, del III, del IV, del V, and del VI deletion sites of the MVA genome. The sites are particularly useful for the insertion of multiple heterologous sequences. The dCVA can reproductively replicate (with an amplification ratio of greater than 10) in a human cell line (such as human 293, 143B, and MRC-5 cell lines), which then enables the optimization by further mutation useful for a virus-based vaccination strategy (see WO 2011/092029).

In a preferred embodiment of the invention, the MVA vector(s) comprise a nucleic acid that encodes one or more antigenic HIV proteins, such as the HIV mosaic antigen. In other preferred embodiments, the MVA vectors encode one or more HIV antigenic polypeptides comprising the amino acid sequences selected from the group consisting of SEQ ID NOs: 1-4, and more preferably encode four HIV antigenic polypeptides having the amino acid sequences of SEQ ID NO: 1, SEQ ID NO: 2, SEQ ID NO: 3, and SEQ ID NO: 4.

Nucleic acid sequences encoding the HIV antigenic protein can be inserted into one or more intergenic regions (IGR) of the MVA. In certain embodiments, the IGR is selected from IGR07/08, IGR 44/45, IGR 64/65, IGR 88/89, IGR 136/137, and IGR 148/149. In certain embodiments, less than 5, 4, 3, or 2 IGRs of the recombinant MVA comprise heterologous nucleotide sequences encoding antigenic determinants of a HIV, such as a mosaic antigen and/or a further HIV antigenic polypeptide. The heterologous nucleotide sequences can, additionally or alternatively, be inserted into one or more of the naturally occurring deletion sites, in particular into the main deletion sites I, II, III, IV, V, or VI of the MVA genome. In certain embodiments, less than 5, 4, 3, or 2 of the naturally occurring deletion sites of the recombinant MVA comprise heterologous nucleotide sequences encoding antigenic determinants of a HIV envelope glycoprotein and/or a further HIV protein.

The number of insertion sites of MVA comprising heterologous nucleotide sequences encoding antigenic determinants of a HIV protein can be 1, 2, 3, 4, 5, 6, 7, or more. In certain embodiments, the heterologous nucleotide sequences are inserted into 4, 3, 2, or fewer insertion sites. Preferably, two insertion sites are used. In certain embodiments, three insertion sites are used. Preferably, the recombinant MVA comprises at least 2, 3, 4, 5, 6, or 7 genes inserted into 2 or 3 insertion sites.

The recombinant MVA viruses provided herein can be generated by routine methods known in the art. Methods to obtain recombinant poxviruses or to insert exogenous coding sequences into a poxviral genome are well known to the person skilled in the art. For example, methods for standard molecular biology techniques such as cloning of DNA, DNA and RNA isolation, Western blot analysis, RT-PCR and PCR amplification techniques are described in Molecular Cloning, A laboratory Manual (2nd Ed.) [83], and techniques for the handling and manipulation of viruses are described in Virology Methods Manual [B. W. J. Mahy et al. (eds.), Academic Press (1996)]. Similarly, techniques and know-how for the handling, manipulation and genetic engineering of MVA are described in Molecular Virology: A Practical Approach [A. J. Davison & R. M. Elliott (Eds.), The Practical Approach Series, IRL Press at Oxford University Press, Oxford, UK (1993) (see, e.g., Chapter 9: Expression of genes by Vaccinia virus vectors)] and Current Protocols in Molecular Biology [John Wiley & Son, Inc. (1998)(see, e.g., Chapter 16, Section IV: Expression of proteins in mammalian cells using vaccinia viral vector)].

For the generation of the various recombinant MVAs disclosed herein, different methods can be applicable. The DNA sequence to be inserted into the virus can be placed into an *E. coli* plasmid construct into which DNA homologous to a section of DNA of the MVA has been inserted. Separately, the DNA sequence to be inserted can be ligated to a promoter. The promoter-gene linkage can be positioned in the plasmid construct so that the promoter-gene linkage is flanked on both ends by DNA homologous to a DNA sequence flanking a region of MVA DNA containing a non-essential locus. The resulting plasmid construct can be amplified by propagation within *E. coli* bacteria and isolated. The isolated plasmid containing the DNA gene sequence to be inserted can be transfected into a cell culture, e.g., of chicken embryo fibroblasts (CEFs), at the same time the culture is infected with MVA. Recombination between homologous MVA DNA in the plasmid and the viral genome, respectively, can generate an MVA modified by the presence of foreign DNA sequences.

According to a preferred embodiment, a cell of a suitable cell culture such as, e.g., CEF cells, can be infected with a poxvirus. The infected cell can be, subsequently, transfected with a first plasmid vector comprising a foreign or heterologous gene or genes, preferably under the transcriptional control of a poxvirus expression control element. As explained above, the plasmid vector also comprises sequences capable of directing the insertion of the exogenous sequence into a selected part of the poxviral genome. Optionally, the plasmid vector also contains a cassette comprising a marker and/or selection gene operably linked to a poxviral promoter. Suitable markers or selection genes are, e.g., the genes encoding the green fluorescent protein, β-galactosidase, neomycin-phosphoribosyltransferase or other markers. The use of selection or marker cassettes simplifies the identification and isolation of the generated recombinant poxvirus. However, a recombinant poxvirus can also be identified by PCR technology. Subsequently, a further cell can be infected with the recombinant poxvirus obtained as described above and transfected with a second vector comprising a second foreign or heterologous gene or genes. In case, this gene shall be introduced into a different insertion site of the poxviral genome, the second vector also differs in the poxvirus-homologous sequences directing the integration of the second foreign gene or genes into the genome of the poxvirus. After homologous recombination has occurred, the recombinant virus comprising two or more foreign or heterologous genes can be isolated. For introducing additional foreign genes into the recombinant virus, the steps of infection and transfection can be repeated by using the recombinant virus isolated in previous steps for infection and by using a further vector comprising a further foreign gene or genes for transfection.

Alternatively, the steps of infection and transfection as described above are interchangeable, i.e., a suitable cell can at first be transfected by the plasmid vector comprising the foreign gene and, then, infected with the poxvirus. As a further alternative, it is also possible to introduce each foreign gene into different viruses, co-infect a cell with all the obtained recombinant viruses and screen for a recombinant including all foreign genes. A third alternative is ligation of DNA genome and foreign sequences in vitro and reconstitution of the recombined vaccinia virus DNA genome using a helper virus. A fourth alternative is homologous recombination in *E. coli* or another bacterial species between a vaccinia virus genome cloned as a bacterial artificial chromosome (BAC) and a linear foreign sequence flanked with DNA sequences homologous to sequences flanking the desired site of integration in the vaccinia virus genome.

The heterologous HIV gene, e.g., nucleic acid encoding one or more HIV antigenic polypeptides, can be under the control of (i.e., operably linked to) one or more poxvirus promoters. In certain embodiments, the poxvirus promoter is a Pr7.5 promoter, a hybrid early/late promoter, or a PrS promoter, a PrS5E promoter, a synthetic or natural early or late promoter, or a cowpox virus ATI promoter.

In a preferred embodiment of the invention, the MVA vectors express polyvalent mosaic Env/Gag/Pol antigens, such as those described in Barouch et al., *Nat Med* 2010, 16:319-323 [54]; Barouch et al., *Cell* 155:1-9, 2013 [65], all of which are incorporated herein by reference in their entirety. According to embodiments of the invention, MVA vectors can express any of the antigenic polypeptides described herein including, but not limited to, HIV mosaic antigens, such as HIV mosaic Gag-Pol-Env antigens.

Immunogenic Compositions

As used herein, "an immunogenically effective amount" or "immunologically effective amount" means an amount of a composition sufficient to induce a desired immune effect or immune response in a subject in need thereof. In one embodiment, an immunogenically effective amount means an amount sufficient to induce an immune response in a subject in need thereof. In another embodiment, an immunogenically effective amount means an amount sufficient to produce immunity in a subject in need thereof, e.g., provide a protective effect against a disease such as viral infection. An immunogenically effective amount can vary depending upon a variety of factors, such as the physical condition of the subject, age, weight, health, etc.; the particular application, whether inducing immune response or providing protective immunity; the specific recombinant vector administered; the immunogen encoded by the recombinant vector administered; the specific antigenic polypeptide administered; and the particular disease, e.g., viral infection, for which immunity is desired. An immunogenically effective amount can readily be determined by one of ordinary skill in the art in view of the present disclosure.

As general guidance, an immunogenically effective amount when used with reference to a recombinant viral vector can range from about $10^8$ viral particles to about $10^{12}$ viral particles, for example $10^8$, $10^9$, $10^{10}$, $10^{11}$, or $10^{12}$ viral particles. An immunogenically effective amount can be administered in a single composition, or in multiple compositions, such as 1, 2, 3, 4, 5, 6, 7, 8, 9, or 10 compositions (e.g., tablets, capsules or injectables), wherein the administration of the multiple capsules or injections collectively provides a subject with the immunogenically effective amount. In general, when used with reference to a polypeptide, such as an isolated antigenic polypeptide, an immunogenically effective amount can range from, e.g. about 0.3 to about 3000 microgram (μg), e.g. 1-1000 μg, e.g. 10-500 μg, e.g. about 50, 100, 150, 200, 250, 300, 350, 400, 450 or 500 μg. It is also possible to administer an immunogenically effective amount to a subject, and subsequently administer another dose of an immunogenically effective amount to the same subject, in a so-called prime-boost regimen. This general concept of a prime-boost regimen is well known to the skill person in the vaccine field. Further booster administrations can optionally be added to the regimen, as needed.

Immunogenic compositions are compositions comprising an immunogenically effective amount of purified or partially purified adenovirus or MVA vectors for use in the invention. Said compositions can be formulated as a vaccine (also referred to as an "immunogenic composition") according to methods well known in the art. Such compositions can include adjuvants to enhance immune responses. The optimal ratios of each component in the formulation can be determined by techniques well known to those skilled in the art in view of the present disclosure.

The preparation and use of immunogenic compositions are well known to those of ordinary skill in the art. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can also be included.

The compositions of the invention can comprise other HIV-1 antigens or the priming or boosting immunizations can comprise other antigens. The other antigens used in combination with the adenovirus vectors of the invention are not critical to the invention and can be, for example, HIV-1 antigens and nucleic acids expressing them.

The immunogenic compositions useful in the invention can comprise adjuvants. Adjuvants suitable for co-administration in accordance with the invention should be ones that are potentially safe, well tolerated and effective in people including QS-21, Detox-PC, MPL-SE, MoGM-CSF, Titer-Max-G, CRL-1005, GERBU, TERamide, PSC97B, Adjumer, PG-026, GSK-I, GcMAF, B-alethine, MPC-026, Adjuvax, CpG ODN, Betafectin, Aluminium salts (e.g. AdjuPhos), Adjuplex, and MF59.

Other adjuvants that can be administered include lectins, growth factors, cytokines and lymphokines such as alpha-interferon, gamma interferon, platelet derived growth factor (PDGF), granulocyte-colony stimulating factor (gCSF), granulocyte macrophage colony stimulating factor (gMCSF), tumor necrosis factor (TNF), epidermal growth factor (EGF), IL-I, IL-2, IL-4, IL-6, IL-8, IL-IO, and IL-12 or encoding nucleic acids therefore.

The compositions of the invention can comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g., intramuscular, subcutaneous, oral, intravenous, cutaneous, intramucosal (e.g., gut), intranasal or intraperitoneal routes.

The ability to induce or stimulate an anti-HIV immune response upon administration in an animal or human organism can be evaluated either in vitro or in vivo using a variety of assays which are standard in the art. For a general description of techniques available to evaluate the onset and activation of an immune response, see for example Coligan et al. (1992 and 1994, Current Protocols in Immunology; ed J Wiley & Sons Inc, National Institute of Health). Measurement of cellular immunity can be performed by measurement of cytokine profiles secreted by activated effector cells including those derived from CD4+ and CD8+ T-cells (e.g. quantification of IL-10 or IFN gamma-producing cells by ELISPOT), by determination of the activation status of immune effector cells (e.g. T cell proliferation assays by a classical [$^3$H] thymidine uptake), by assaying for antigen-specific T lymphocytes in a sensitized subject (e.g. peptide-specific lysis in a cytotoxicity assay, etc.).

The ability to stimulate a cellular and/or a humoral response can be determined by antibody binding and/or competition in binding (see for example Harlow, 1989, Antibodies, Cold Spring Harbor Press). For example, titers of antibodies produced in response to administration of a composition providing an immunogen can be measured by enzyme-linked immunosorbent assay (ELISA). The immune responses can also be measured by neutralizing antibody assay, where a neutralization of a virus is defined as the loss of infectivity through reaction/inhibition/neutralization of the virus with specific antibody. The immune response can further be measured by Antibody-Dependent Cellular Phagocytosis (ADCP) Assay.

According to embodiments of the invention, upon administration to a subject, an expression vector, such as a recombinant adenovirus vector or recombinant MVA vector, expresses an immunogenic polypeptide. Any of the antigenic polypeptides described herein can be encoded by an expression vector and administered to a subject in a method of the invention. The expressed immunogenic polypeptide is presented to the immune system of the subject, thereby inducing the required response to produce immunity, or induce an immune response to treat or prevent a disease or infection. For example, the response can be the production of antibodies specific to the immunogenic polypeptide.

Preferably, upon administration to a subject, an expression vector expresses a mosaic HIV Gag-Pol-Env antigen. Presentation of a mosaic HIV Gag-Pol-Env antigen according to the invention to the immune system of a subject can induce the production of antibodies specific to the HIV gag, pol, and/or env gene products, depending on the sequence composition of the expressed mosaic HIV antigen.

Vaccine Combination

A general aspect of the invention relates to a vaccine combination for inducing an immune response against a human immunodeficiency virus (HIV) in a subject in need thereof, comprising:

(i) a first composition comprising an immunogenically effective amount of one or more expression vectors encoding one or more HIV antigenic polypeptides and a pharmaceutically acceptable carrier;

(ii) a second composition comprising an immunogenically effective amount of an isolated antigenic polypeptide and a pharmaceutically acceptable carrier; and (iii) an immunogenically effective amount of one or more additional expression vectors encoding one or more additional antigenic polypeptides, wherein one of the first and the second compositions is for priming immunization and the other composition is for boosting immunization, and the immunogenically effective amount of the additional expression vectors is present in the second composition or in a third composition to be administered together with the second composition for priming or boosting immunization.

In a preferred embodiment, the isolated antigenic polypeptide comprises an HIV envelope glycoprotein. Examples of the envelope glycoprotein include any of the HIV envelope glycoproteins described above, including but not limited to, gp160, gp140, gp120, or gp41 from any Glade of HIV. Preferably, the isolated antigenic polypeptide comprises a stabilized trimer of an HIV envelope protein, such as a stabilized trimer of HIV gp140, particularly a Glade C stabilized trimer of HIV gp140, such as that comprising the amino acid sequence of SEQ ID NO: 5. In another embodiment of the invention, the HIV envelope glycoprotein is a mosaic HIV envelope glycoprotein, such as a mosaic HIV gp140 protein, such as that comprising the amino acid sequence of SEQ ID NO:6.

In another preferred embodiment, the expression vector or the additional expression vector is an adenovirus vector or an MVA vector. Preferably, vectors of different origin are used for priming and boosting immunization. For example, when an adenovirus vector is used for the priming immunization, a MVA vector is used for the boosting immunization. Likewise, when a MVA vector is used for the priming immunization, an adenovirus vector is used for the boosting immunization. In a preferred embodiment of the invention, one or more adenovirus vectors, more preferably rAd26 vectors, are used for the priming immunization, and one or more MVA vectors, together with the isolated HIV antigenic polypeptide, such as an HIV envelope protein, are used for the boosting immunization.

In other embodiments of the invention, one or more adenovirus vectors, preferably rAd26 vectors, are used for the priming immunization, and one or more adenovirus vectors, preferably rAd26 vectors, together with an isolated HIV antigenic polypeptide, such as an HIV envelope protein, preferably a stabilized trimeric gp140 protein, are used for the boosting immunization. The adenovirus vectors used for boosting immunization can encode the same antigenic proteins as those encoded by the adenovirus vectors used for priming immunization.

In yet another embodiment of the invention, an isolated HIV antigenic polypeptide and one or more adenovirus vectors, preferably rAd26 vectors, are used for priming immunization, and an isolated HIV antigenic polypeptide and one or more adenovirus vectors, preferably rAd26 vectors, are used for boosting immunization.

According to embodiments of the invention, any of the HIV antigenic polypeptides discussed above can be encoded by the expression vector(s) and the additional expression vector(s). In a preferred embodiment, the antigenic polypeptide is an HIV mosaic antigen, more preferably a mosaic HIV Gag-Pol-Env antigen. Examples of mosaic HIV Gag-Pol-Env antigens include, but are not limited to mosaic antigens comprising the amino acid sequences of SEQ ID NOs: 1 to 4.

In one embodiment of the invention, the first composition comprises rAd26 vectors encoding one or more mosaic HIV antigenic polypeptides, such as mosaic HIV Gag-Pol-Env antigens; the second composition comprises an isolated HIV envelope protein, such as a stabilized trimer of HIV gp140 or a mosaic HIV envelope protein; and the additional expression vectors are MVA vectors encoding one or more mosaic HIV antigenic polypeptides, such as mosaic HIV Gag-Pol-Env antigens.

In a preferred embodiment of the invention, the first composition comprises rAd26 vectors encoding one or more proteins having the amino acid sequences of SEQ ID NOs: 1 to 4; the second composition comprises an isolated antigenic polypeptide having the amino acid sequence of SEQ ID NO: 5 or SEQ ID NO:6; and the additional expression vectors are MVA vectors encoding one or more proteins having the amino acid sequences of SEQ ID NOs: 1-4.

In a particularly preferred embodiment of the invention, the first composition comprises rAd26 vectors encoding three mosaic HIV proteins having the amino acid sequences of SEQ ID NO: 1, SEQ ID NO: 3 and SEQ ID NO: 4, respectively; the second composition comprises an isolated stabilized trimer of HIV gp140 having the amino acid sequence of SEQ ID NO: 5; and the MVA vectors are present in a third composition, and encode four mosaic HIV antigenic proteins having the amino acid sequences of SEQ ID NOs: 1 to 4.

According to embodiments of the invention, the first composition can comprise one expression vector, or more than one expression vector. In one embodiment, the first composition comprises one expression vector, such as an adenovirus vector, and more preferably a rAd26 vector. In another embodiment, the first composition comprises more than one expression vector, such as one, two, three, or four, etc. expression vectors, which are preferably adenovirus vectors, such as rAd26 vectors. The one or more expression vectors can express the same or different HIV antigenic polypeptides. Each of the expression vectors can express one HIV antigenic polypeptide sequence, or more than one HIV antigenic polypeptide sequence. As an illustrative and non-limiting example, the first composition can comprise three rAd26 vectors, each expressing a different HIV antigenic polypeptide, preferably selected from the group consisting of SEQ ID NOs: 1-4, and more preferably SEQ ID NOs: 1, 3, and 4.

According to embodiments of the invention, the one or more additional expression vectors can be one expression vector, or more than expression vector, such as two, three, four or more expression vectors. The one or more additional expression vectors can express the same or different antigenic polypeptides. Each of the one more additional expression vectors can express one antigenic polypeptide sequence, or multiple antigenic polypeptide sequences. As an illustrative and non-limiting example, two additional expression vectors are used, preferably MVA vectors, with each MVA vector encoding a different mosaic HIV antigen sequence, such as mosaic HIV Gag-Pol-Env antigen sequences selected from the group consisting of SEQ ID NOs: 1-4. Preferably, in such embodiment of the invention, one MVA vector encodes HIV antigenic polypeptides comprising SEQ ID NOs: 1 and 3, and the other MVA vector encodes HIV antigenic polypeptides comprising SEQ ID NOs: 2 and 4.

The vaccine combination according to embodiments of the invention is effective to induce an immune response against one or multiple clades of HIV.

Method for Inducing Protective Immunity Against HIV Infection

The invention provides a method of priming and boosting an immune response to one or more HIV clades in a subject in need thereof using one or more expression vectors in combination with an isolated antigenic polypeptide.

According to one general aspect of the invention, a method of inducing an immune response against a human immunodeficiency virus (HIV) in a subject in need thereof comprises:

(i) administering to the subject a first composition comprising an immunogenically effective amount of one or more expression vectors encoding one or more HIV antigenic polypeptides and a pharmaceutically acceptable carrier;

(ii) administering to the subject a second composition comprising an immunogenically effective amount of an isolated antigenic polypeptide and a pharmaceutically acceptable carrier;

(iii) administering to the subject an immunogenically effective amount of one or more additional expression vectors encoding one or more additional HIV antigenic polypeptides, wherein steps (a) and (b) are conducted in either order, with one of the steps for priming immunization and the other for boosting immunization, and the immunogenically effective amount of the one or more additional expression vectors is present in the second composition or in a third composition administered together with the second composition for the priming or the boosting immunization.

Any of the vaccine combinations according to embodiments of the invention can be used in the present method.

According to embodiments of the invention, "inducing an immune response" when used with reference to the methods described herein encompasses providing protective immunity and/or vaccinating a subject against an infection, such as a HIV infection, for prophylactic purposes, as well as causing a desired immune response or effective in a subject in need thereof against an infection, such as a HIV infection, for therapeutic purposes. Preferably, the methods of the invention are for prophylactic purposes, such as for providing protective immunity.

Embodiments of the isolated antigenic polypeptides, expression vectors, additional expression vectors, antigenic polypeptide encoded by the expression vectors, etc. that can be used in the methods of the invention are discussed in detail above and in the illustrative examples below.

In one embodiment of the disclosed methods, one or more adenovirus vectors encoding one or more HIV antigenic polypeptides are used to prime the immune response. One or more isolated HIV antigenic polypeptides can be used together with the one or more adenovirus vectors for the priming immunization. The priming immunization can be administered multiple times, for example, initial priming administration at time 0, followed by another priming administration about 10-14 weeks after the initial priming administration. One or more isolated HIV antigenic polypeptides together with one or more additional adenovirus or MVA vectors encoding one or more additional HIV antigenic polypeptides are used to boost the immune response. The boosting immunization can also be administered multiple times, for example, first at about 22-26 weeks after the initial priming administration, followed by another boosting administration at about 46-50 weeks after the initial priming administration. The immune response induced by the immunization is monitored.

Embodiments of the disclosed methods also contemplate shorter prime-boost regimens, meaning that the final boosting immunization is administered about 22-26 weeks after the initial priming administration. The priming immunization can be administered at week 0. The boosting immunization can be administered multiple times, for example, first at about 7-9 weeks or 11-13 weeks after the initial priming administration, followed by another boosting administration at about 22-26 weeks after the initial priming administration. In certain embodiments, one or more isolated HIV antigenic polypeptides is administered together with the one or more adenovirus vectors for the priming immunization.

It is readily appreciated by those skilled in the art that the regimen for the priming and boosting administrations can be adjusted based on the measured immune responses after the administrations. For example, the boosting compositions are generally administered weeks or months after administration of the priming composition, for example, about 2-3 weeks or 4 weeks, or 8 weeks, or 16 weeks, or 20 weeks, or 24 weeks, or 28 weeks, or 30 weeks or 32 weeks or one to two years after administration of the priming composition.

In a preferred embodiment of the invention, the adenovirus vectors used in the methods disclosed herein include an rAd26 vector. In one exemplary embodiment, an rAd26 vector is used to prime the immune response, and an MVA vector together with an isolated antigenic polypeptide is used to boost the immune response, or vice versa.

In one or more embodiments of the described method, a plurality of rAd26 vectors are used to prime the immune response, and a plurality of isolated antigenic proteins, optionally together with a plurality of MVA vectors, are used to boost the immune response, or vice versa.

In a preferred embodiment according to the method herein, a plurality of rAd26 vectors are used for the priming immunization, followed by a boosting immunization with a plurality of MVA vectors and an isolated antigenic polypeptide. Preferably, the boosting immunization is administered 10-36 weeks after the last priming, more preferably 12-24 weeks after priming.

The antigens in the respective priming and boosting compositions (however many boosting compositions are employed) need not be identical, but should share antigenic determinants or be substantially similar to each other.

Administration of the immunogenic compositions comprising the expression vectors and/or antigenic polypeptides is typically intramuscular or subcutaneous. However other modes of administration such as intravenous, cutaneous, intradermal or nasal can be envisaged as well. Intramuscular administration of the immunogenic compositions can be achieved by using a needle to inject a suspension of the expression vectors, e.g. adenovirus and/or MVA vectors, and/or antigenic polypeptides. An alternative is the use of a needleless injection device to administer the composition (using, e.g., Biojector™) or a freeze-dried powder containing the vaccine.

For intravenous, cutaneous or subcutaneous injection, or injection at the site of affliction, the vector will be in the form of a parenterally acceptable aqueous solution which is pyrogen-free and has suitable pH, isotonicity and stability. Likewise, the isolated antigenic polypeptide will be in the form of a parenterally acceptable solution having a suitable pH, isotonicity, and stability. Those of ordinary skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required. A slow-release formulation can also be employed.

Typically, administration of the vaccine compositions according to embodiments of the invention will have a prophylactic aim to generate an immune response against an HIV antigen before infection or development of symptoms. Diseases and disorders that can be treated or prevented in accordance with the invention include those in which an immune response can play a protective or therapeutic role. In other embodiments, the expression vectors, e.g., adenovirus and/or MVA vectors, and/or antigenic polypeptides can be administered for post-exposure prophylactics.

The immunogenic compositions containing the expression vectors, e.g., adenovirus vectors and/or MVA vectors, and antigenic polypeptides are administered to a subject, giving rise to an anti-HIV immune response in the subject. An amount of a composition sufficient to induce a detectable immune response is defined to be an "immunogenically effective dose." As shown in the Examples below, the immunogenic compositions of the invention induce a humoral as well as a cell-mediated immune response. In a typical embodiment of the invention, the immune response is a protective immune response.

The actual amount administered, and rate and time-course of administration, will depend on the nature and severity of what is being treated. Prescription of treatment, e.g., decisions on dosage etc., is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. ed., 1980.

Following production of adenovirus and MVA vectors and optional formulation of such particles into compositions, the vectors can be administered to an individual, particularly human or other primate. Administration can be to humans, or another mammal, e.g., mouse, rat, hamster, guinea pig, rabbit, sheep, goat, pig, horse, cow, donkey, monkey, dog or cat. Delivery to a non-human mammal need not be for a therapeutic purpose, but can be for use in an experimental context, for instance in investigation of mechanisms of immune responses to the gp140 protein or the antigens expressed by the adenovirus or MVA vectors.

In one exemplary regimen, the adenovirus or MVA vector is administered (e.g., intramuscularly) in the range of from about 100 µl to about 10 ml of saline solution containing concentrations of from about $10^4$ to $10^{12}$ virus particles/ml. Typically, the adenovirus or MVA vector is administered in an amount of about $10^9$ to about $10^{12}$ viral particles (vp) to a human subject during one administration, more typically from about $10^{10}$ to about $10^{12}$ vp. The initial vaccination is followed by a boost as described above. The isolated HIV antigenic polypeptide can for instance be administered ranging from about 0.001 to 30 mg/kg body weight. The skilled artisan will appreciate that certain factors may influence the dosage required to effectively treat a subject, including but not limited to the severity of the disease or disorder, previous treatments, the general health and/or age of the subject, and other diseases present.

The composition can, if desired, be presented in a kit, pack or dispenser, which can contain one or more unit dosage forms containing the active ingredient. The kit, for example, can comprise metal or plastic foil, such as a blister pack. The kit, pack, or dispenser can be accompanied by instructions for administration.

The compositions of the invention can be administered alone or in combination with other treatments, either simultaneously or sequentially depending upon the condition to be treated, and other factors that may affect the treatment.

EMBODIMENTS

Embodiment 1 is a vaccine combination for inducing an immune response against a human immunodeficiency virus (HIV) in a subject in need thereof, comprising:

(i) a first composition comprising an immunogenically effective amount of one or more expression vectors encoding one or more HIV antigenic polypeptides and a pharmaceutically acceptable carrier;

(ii) a second composition comprising an immunogenically effective amount of an isolated antigenic polypeptide and a pharmaceutically acceptable carrier; and (iii) an immunogenically effective amount of one or more additional expression vectors encoding one or more additional antigenic polypeptides, wherein one of the first and the second compositions is for priming immunization and the other composition is for boosting immunization, and the immunogenically effective amount of the additional expression vectors is present in the second composition or in a third composition to be administered together with the second composition for priming or boosting immunization.

Embodiment 2 is a vaccine combination according to embodiment 1, wherein the isolated antigenic polypeptide comprises an HIV envelope glycoprotein.

Embodiment 3 is a vaccine combination according to embodiment 2, wherein the isolated antigenic polypeptide comprises a stabilized trimer of HIV gp140.

Embodiment 4 is a vaccine combination according to any one of embodiments 1 to 3, wherein the one or more expression vectors and the one or more additional expression vectors are adenovirus vectors or MVA vectors.

Embodiment 5 is a vaccine combination according to embodiment 4, wherein the one or more expression vectors are rAd26 vectors and the one or more additional expression vectors are MVA vectors; the one or more expression vectors are MVA vectors and the one or more additional expression vector are rAd26 vectors; or the one or more expression vectors are rAd26 vectors and the one or more additional expression vector are also rAd26 vectors.

Embodiment 6 is a vaccine combination according to any one of embodiments 1-5, wherein the one or more expression vectors and the one or more additional expression vectors encode one or more HIV antigenic polypeptides comprising the amino acid sequences selected from the group consisting of SEQ ID NOs: 1-4.

Embodiment 7 is a vaccine combination according to embodiment 6, wherein the one or more expression vectors are rAd26 vectors encoding one or more HIV antigenic polypeptides comprising the amino acid sequences selected from the group consisting of SEQ ID NOs: 1-4; the isolated antigenic polypeptide comprises the amino acid sequence of SEQ ID NO: 5 or SEQ ID NO:6; and the one or more additional expression vectors are MVA vectors encoding one or more HIV antigenic polypeptides comprising the amino acid sequences selected from the group consisting of SEQ ID NOs: 1-4.

Embodiment 8 is a vaccine combination according to embodiment 7, wherein the first composition is for the priming immunization, and the second composition and the immunogenically effective amount of the one or more additional expression vectors are for the boosting immunization.

Embodiment 9 is a vaccine combination according to embodiment 8, wherein the immunogenically effective amount of the one or more additional expression vectors is present in the third composition.

Embodiment 10 is a vaccine combination according to embodiment 9, wherein the first composition comprises rAd26 vectors encoding three HIV antigenic polypeptides having the amino acid sequences of SEQ ID NO: 1, SEQ ID NO: 3, and SEQ ID NO: 4, respectively; the isolated antigenic polypeptide comprises a stabilized trimer of HIV gp140 having the amino acid sequence of SEQ ID NO: 5; and the third composition comprises MVA vectors encoding four HIV antigenic polypeptides having the amino acid sequences of SEQ ID NO: 1, SEQ ID NO: 2, SEQ ID NO: 3 and SEQ ID NO: 4.

Embodiment 11 is a vaccine combination according to any one of embodiments 1-10, wherein administration of the vaccine combination to a subject induces an immune response against multiple clades of HIV.

Embodiment 12 is a vaccine combination according to any one of embodiments 1-11 for use in generating a protective immune response against HIV infection, wherein the first composition is used for priming the immune response, and the second composition and the immunogenically effective amount of the one or more additional expression vectors are used for boosting the immune response.

Embodiment 13 is a kit comprising the vaccine combination of any of embodiments 1-12.

Embodiment 14 is a method of inducing an immune response against a human immunodeficiency virus (HIV) in a subject in need thereof, the method comprising:
(i) administering to the subject a first composition comprising an immunogenically effective amount of one or more expression vectors encoding one or more HIV antigenic polypeptides and a pharmaceutically acceptable carrier;
(ii) administering to the subject a second composition comprising an immunogenically effective amount of an isolated antigenic polypeptide and a pharmaceutically acceptable carrier; and
(iii) administering to the subject an immunogenically effective amount of one or more additional expression vectors encoding one or more additional HIV antigenic polypeptides,
wherein steps (i) and (ii) are conducted in either order, with one of the steps for priming immunization and the other for boosting immunization, and the immunogenically effective amount of the one or more additional expression vectors is present in the second composition or in a third composition administered together with the second composition for the priming or the boosting immunization.

Embodiment 15 is a method according to embodiment 14, wherein the isolated antigenic polypeptide comprises an HIV envelope glycoprotein.

Embodiment 16 is a method according to embodiment 15, wherein the isolated antigenic polypeptide comprises a stabilized trimer of HIV gp140.

Embodiment 17 is a method according to any one of embodiments 14 to 16, wherein the one or more expression vectors and the one or more additional expression vectors are adenovirus vectors or MVA vectors.

Embodiment 18 is a method according to embodiment 17, wherein the one or more expression vectors are rAd26 vectors and the one or more additional expression vectors are MVA vectors; the one or more expression vectors are MVA vectors and the one or more additional expression vectors are rAd26 vectors; or the one or more expression vectors are rAd26 vectors and the one or more additional expression vectors are also rAd26 vectors.

Embodiment 19 is a method according to any one of embodiments 14-18, wherein the one or more expression vectors and the one or more additional expression vectors encode one or more HIV antigenic polypeptides comprising the amino acid sequences selected from the group consisting of SEQ ID NOs: 1-4.

Embodiment 20 is a method according to embodiment 19, wherein the one or more expression vectors are rAd26 vectors encoding one or more HIV antigenic polypeptides comprising the amino acid sequences selected from the group consisting of SEQ ID NOs: 1-4; the isolated antigenic polypeptide comprises the amino acid sequence of SEQ ID NO: 5 or SEQ ID NO: 6; and the one or more additional expression vectors are MVA vectors encoding one or more HIV antigenic polypeptides comprising the amino acid sequences selected from the group consisting of SEQ ID NOs: 1-4.

Embodiment 21 is a method according to embodiment 20, wherein the first composition is for the priming immunization, the second composition and the immunogenically effective amount of the one or more additional expression vectors are for the boosting immunization.

Embodiment 22 is a method according to embodiment 21, wherein the immunogenically effective amount of the one or more additional expression vectors is present in the third composition.

Embodiment 23 is a method according to embodiment 22, wherein the first composition comprises rAd26 vectors encoding three HIV antigenic polypeptides having the amino acid sequences of SEQ ID NO: 1, SEQ ID NO: 3 and SEQ ID NO: 4, respectively; the isolated antigenic polypeptide comprises a stabilized trimer of HIV gp140 having the amino acid sequence of SEQ ID NO: 5; and the third composition comprises MVA vectors encoding four HIV antigenic polypeptides having the amino acid sequences of SEQ ID NO: 1, SEQ ID NO: 2, SEQ ID NO: 3 and SEQ ID NO: 4.

Embodiment 24 is a method according to any one of embodiments 14-23, wherein administration of the vaccine combination to a subject induces an immune response against multiple clades of HIV.

Embodiment 25 is a method of inducing an immune response against a human immunodeficiency virus (HIV) in a subject in need thereof, the method comprising:
(i) administering to the subject a primer vaccine comprising an immunogenically effective amount of one or more expression vectors encoding one or more HIV antigenic polypeptides and a pharmaceutically acceptable carrier; and
(ii) administering to the subject a booster vaccine comprising an immunogenically effective amount of an isolated HIV antigenic polypeptide, an immunogenically effective amount of one or more additional expression vectors encoding one or more additional HIV antigenic polypeptides, and a pharmaceutically acceptable carrier,
wherein the isolated antigenic polypeptide and the one or more additional expression vectors are present in the same composition or separate compositions; and
wherein the booster vaccine is administered after the primer vaccine is administered.

Embodiment 26 is a method according to embodiment 25, wherein the booster vaccine is first administered at about 22-26 weeks after the primer vaccine is initially administered.

Embodiment 27 is a method according to embodiment 25 or 26, further comprising re-administering the primer vaccine to the subject after the primer vaccine is initially administered, but before the booster vaccine is first administered.

Embodiment 28 is a method according to embodiment 27, wherein the primer vaccine is re-administered at about 10-14 weeks after the primer vaccine is initially administered.

Embodiment 29 is a method according to any of embodiments 25-28, further comprising re-administering the booster vaccine to the subject.

Embodiment 30 is a method according to embodiment 29, wherein the booster vaccine is re-administered at about 22-26 weeks after the previous administration of the booster vaccine.

Embodiment 31 is a method according to any one of embodiments 25-30, wherein the one or more expression vectors are rAd26 vectors and the one or more additional expression vector are MVA vectors; the one or more expression vectors are MVA vectors and the one or more additional expression vector are rAd26 vectors; or the one or more expression vectors are rAd26 vectors and the one or more additional expression vector are also rAd26 vectors.

Embodiment 32 is a method according to any one of embodiments 25-30, wherein the one or more expression vectors are rAd26 vectors encoding one or more HIV antigenic polypeptides comprising the amino acid sequences selected from the group consisting of SEQ ID NOs: 1-4; wherein the isolated antigenic polypeptide comprises the amino acid sequence of SEQ ID NO: 5 or SEQ ID NO: 6; and the one or more additional expression vectors are rAd26 vectors or MVA vectors encoding one or more HIV antigenic polypeptides comprising the amino acid sequences selected from the group consisting of SEQ ID NOs: 1-4.

Embodiment 33 is a method according to embodiment 32, wherein the one or more additional expression vectors are rAd26 vectors.

Embodiment 34 is a method according to embodiment 32, wherein the one or more additional expression vectors are MVA vectors.

Embodiment 35 is a method according to embodiment 25, wherein the booster vaccine is first administered about 8-12 weeks after the primer vaccine is initially administered, and is re-administered at about 24 weeks after the primer vaccine is initially administered.

Embodiment 36 is a method according to embodiment 35, wherein the primer vaccine further comprises an immunogenically effective amount of the isolated HIV antigenic polypeptide, wherein the isolated HIV antigenic polypeptide are present in the same composition or separate compositions.

Embodiment 37 is a method according to any one of embodiments 34-35, wherein the one or more expression vectors are rAd26 vectors encoding one or more HIV antigenic polypeptide sequences preferably comprising the amino acid sequences selected from the group consisting of SEQ ID NOs: 1-4; wherein the isolated antigenic polypeptide is an HIV envelope glycoprotein preferably comprising the amino acid sequence of SEQ ID NO: 5 or SEQ ID NO: 6; and the one or more additional expression vectors are rAd26 or MVA vectors encoding one or more HIV antigenic polypeptide sequences preferably comprising the amino acid sequences selected from the group consisting of SEQ ID NOs: 1-4.

Embodiment 38 is a method according to embodiment 37, wherein the one or more expression vectors are rAd26 vectors encoding HIV antigenic polypeptide sequences of SEQ ID NOs: 1, 3 and 4; and the one or more additional expression vectors are rAd26 vectors encoding HIV antigenic polypeptide sequences of SEQ ID NOs: 1, 3 and 4.

Embodiment 39 is a method of inducing an immune response against a human immunodeficiency virus (HIV) in a subject in need thereof, the method comprising:

(i) administering to the subject a primer vaccine comprising an immunogenically effective amount of one or more rAd26 expression vectors encoding HIV antigenic polypeptides of SEQ ID NOs: 1, 3 and 4 and a pharmaceutically acceptable carrier; and (ii) administering to the subject a booster vaccine comprising an immunogenically effective amount of an isolated HIV envelope glycoprotein comprising the amino acid sequence of SEQ ID NO: 5 or SEQ ID NO: 6, and a pharmaceutically acceptable carrier; and wherein the booster vaccine is administered after the primer vaccine is administered.

Embodiment 40 is a method according to embodiment 39, wherein the booster vaccine comprises an adjuvant, preferably an aluminum salt, and more preferably aluminum phosphate.

Embodiment 41 is a method according to embodiment 39 or 40, wherein the isolated HIV envelope glycoprotein in the booster vaccine comprises the amino acid sequence of SEQ ID NO: 5.

Embodiment 42 is a method according to any one of embodiments 39-41, wherein a second primer vaccine comprising an immunogenically effective amount of one or more rAd26 expression vectors encoding HIV antigenic polypeptides of SEQ ID NOs: 1, 3 and 4 and a pharmaceutically acceptable carrier is administered to the subject after step (i) and before step (ii).

Embodiment 43 is a method according to any one of embodiments 39-42, wherein a further booster vaccine comprising an immunogenically effective amount of an isolated HIV envelope glycoprotein comprising the amino acid sequence of SEQ ID NO: 5 or SEQ ID NO: 6, preferably SEQ ID NO: 5, and a pharmaceutically acceptable carrier, is administered to the subject after step (ii).

Embodiment 44 is a method according to any one of embodiments 39-43, wherein the immunogenically effective amount of the isolated HIV envelope glycoprotein comprising the amino acid sequence of SEQ ID NO: 5 is 250 µg.

Embodiment 45 is a method according to any one of embodiments 39-44, wherein the immunogenically effective amount of one or more rAd26 expression vectors encoding HIV antigenic polypeptides of SEQ ID NOs: 1, 3 and 4 consists of three rAd26 vectors of which a first vector encodes HIV antigenic polypeptide of SEQ ID NO: 1, a second vector encodes HIV antigenic polypeptide of SEQ ID NO: 3, and a third vector encodes HIV antigenic polypeptide of SEQ ID NO: 4, wherein the three rAd26 expression vectors are administered at a total dose of $5 \times 10^{10}$ vp.

The following examples of the invention are to further illustrate the nature of the invention. It should be understood that the following examples do not limit the invention and the scope of the invention is to be determined by the appended claims.

EXAMPLES

Example 1. Study of HIV Vaccine Regimens in Non-Human Primates

An animal study was conducted to identify a multivalent HIV-1 vaccine regimen for continued advanced development. The study tested an extended vaccination schedule using two priming immunizations (at 0 weeks and 12 weeks) and a first boosting immunization (at 24 weeks). A second boosting immunization was administered at week 52. In particular, the study tested the impact of using a combination of an adenovirus or MVA vector with an envelope glycoprotein in heterologous vaccine combinations. The humoral and cellular immunological responses were tested in vaccinated non-human primates (also referred to as "NHP").

Vaccination and Experimental Design

Rhesus monkeys (*Macaca mulatta*) (NHPs) were vaccinated using four different vaccine platforms with 12 animals per group (Groups II-V), in addition to two control groups (Groups I and VI) also with 12 animals each. The first control group (Group I) received primer and booster vaccines of Ad26 vectors expressing HIV-1 mosaic Env1 (SEQ ID NO: 1), mosaic GagPol1 (SEQ ID: NO 3), and mosaic GagPol2 (SEQ ID NO: 4) genes without any isolated HIV antigenic protein. The Ad26 vectors are termed "Ad26.mos1Env, Ad26.mos1Gag-Pol, and Ad26.mos2Gag-Pol, respectively, and are collectively referred to as "Ad26$_{mos}$." The second control group (Group VI) received only placebo ("Sham") primer and booster vaccines.

All groups, except Group VI, received two primer vaccines with Ad26$_{mos}$ at weeks 0 and 12, followed by a first booster vaccine at 24 weeks. A subsequent booster vaccine was administered at 52 weeks.

In particular, Group II received two primer vaccines of Ad26$_{mos}$, followed by two booster vaccines with 250 μg Glade C Env gp140 trimeric protein (SEQ ID NO: 5) dosed with the adjuvant aluminum phosphate (hereinafter referred to as "gp140 drug product" or "gp140 DP"). Group III received two primer vaccines of Ad26$_{mos}$, followed by two booster vaccines with co-delivered Ad26$_{mos}$ and the gp140 DP. Group IV received two primer vaccines of Ad26$_{mos}$, followed by two booster vaccines with a composition containing two different MVA vectors, with one MVA vector expressing a mosaic Env1 gene (SEQ ID NO: 1) and a mosaic GagPol1 gene (SEQ ID NO: 3), and the other MVA vector expressing a mosaic Env2 gene (SEQ ID NO: 2) and a mosaic GagPol2 gene (SEQ ID NO: 4), with the genes being at separate locations on the vectors. The MVA vectors are termed "MVA.mos1Env/Gag-Pol" and "MVA.mos2Env/Gag-Pol," and are collectively referred to as "MVA$_{mos}$." Group V received two primer vaccines of Ad26$_{mos}$, followed by two booster vaccines with co-delivered MVA$_{mos}$ and the gp140 DP. The vaccine regimens tested on NHPs are summarized in Table 1A below.

TABLE 1A

Vaccine regimens tested on NHPs.

| Group | 0 weeks | 12 weeks | 24 weeks | 52 weeks |
|---|---|---|---|---|
| Group I | Ad26$_{mos}$[1] | Ad26$_{mos}$ | Ad26$_{mos}$ | Ad26$_{mos}$ |
| Group II | Ad26$_{mos}$ | Ad26$_{mos}$ | gp140 DP[3] | gp140 DP |
| Group III | Ad26$_{mos}$ | Ad26$_{mos}$ | Ad26$_{mos}$ + gp140 DP | Ad26$_{mos}$ + gp140 DP |
| Group IV | Ad26$_{mos}$ | Ad26$_{mos}$ | MVA$_{mos}$[2] | MVA$_{mos}$ |
| Group V | Ad26$_{mos}$ | Ad26$_{mos}$ | MVA$_{mos}$ + gp140 DP | MVA$_{mos}$ + gp140 DP |
| Group VI | Sham | Sham | Sham | Sham |

[1]Ad26$_{mos}$ = Ad26.mos1Gag-Pol + Ad26.mos1Env + Ad26.mos2Gag-Pol (5 × 10$^{10}$ vp in total)
[2]MVA$_{mos}$ = MVA.mos1Env/Gag-Pol + MVA.mos2Env/Gag-Pol (1 × 10$^8$ pfu in total)
[3]gp140 DP = purified clade C Env gp140 trimeric protein dosed with an adjuvant (250 μg protein + 0.425 mg aluminum phosphate) prepared by extemporaneous mixing The following initial core assay experiments, including ELISA binding antibody assays, antibody-dependent cellular phagocytosis (ADCP) assays, and ELISPOT assays were performed on samples taken from the NHPs treated according to the regimens described in Table 1A at 28 weeks and/or 54/56 weeks following the initial administration of the primer vaccine. A simian/human immunodeficiency virus (SHIV) challenge experiment is performed at week 72.

ELISA Binding Antibody (Ab) Assay

HIV-1-specific humoral response was determined at 28 and 56 weeks by a modified enzyme-linked immunosorbent assay (ELISA). The wells in one column of 96-well flat-bottomed plates (Nunc) were coated with 10 μg of Glade C (C97ZA.012) gp140 coating protein (SEQ ID NO: 5), or 10 μg of mosaic 1 protein (SEQ ID NO: 6) diluted in 10 mL of 1× Dulbecco's Phosphate Buffered Saline (DPBS) (Gibco/Life Technologies) at 100 μL per well, and incubated overnight at 4° C. A known positive serum sample from an earlier study was used as a positive control, and a pre-vaccination serum sample was used as a negative control.

Plate-wells were washed once with 200 μL of ELISA Wash (1000 mL PBS (1×) and 0.5 mL Tween 20 (Sigma)). Wells were blocked with 250 μL of blocking solution (Blocker Casein in PBS (Pierce)) and incubated at room temperature for 3-4 hours. After incubation, the blocking solution was discarded. Then, 150 μL of blocking solution and 6 μL of the sample serum were added to the first column of each plate and 100 μL blocking solution in all other wells. Serial dilutions of 50 μL into 100 μL of blocking solution were then performed across the plate, and 50 μL were discarded from the final column so each well had 100 μL of sample. Plates were incubated at room temperature for 1 hour. The contents of the wells were discarded, and then the wells were washed 3 times with 200 μL of ELISA Wash.

Then, 100 μL of 1:2000 secondary antibody Peroxidase-AffiniPure Goat anti-human IgG (Jackson ImmunoResearch Labs) in blocking solution were added to each well. Plates were again incubated at room temperature for 1 hour and washed 3 times with ELISA Wash. The wells were developed with 100 μL of SeruBlue TMB Microwell Solution (KPL Laboratories), and development was stopped after 0.5 min with 100 μL of TMB Stop Solution (KPL Research Products).

The plates were read on an ELISA plate reader at 450 nm and 550 nm (Molecular Devices-Versamax, and Softmax Pro 4.7.1 software). ELISA EC$_{90}$ titers were calculated using the following equation (I), in which the variables were derived from the 4-parameter curve fit generated by SoftMaxPro:

$$EC_F = \left(\frac{F}{100-F}\right)^{\sqrt{H}} \cdot EC_{50}, \tag{I}$$

wherein H represents the slope and F represents the percent response.

Statistical analyses of data were performed by nonparametric comparison with control using the Dunn method for joint ranking, and the group with the highest geometric mean titer was defined as control, respectively.

Figure 1B:
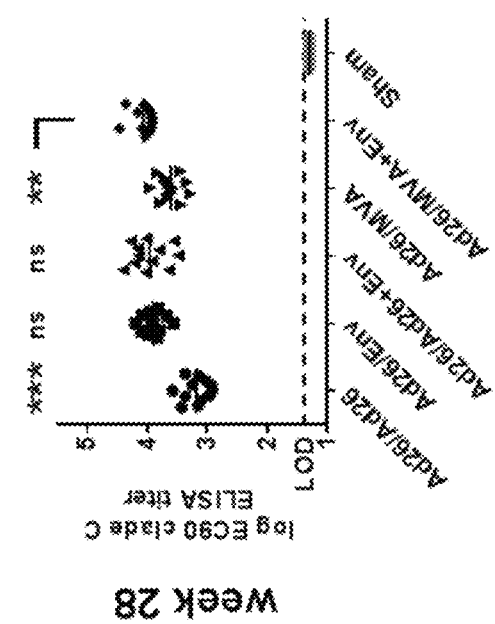

The results from the Glade C gp140 (C97) and Mosaic 1 (Mos1) ELISA assay experiments are summarized in FIG. 1A (week 28) and FIG. 1B (week 56). Clade C gp140 Env and Mosaic 1 Env antigens displayed good correlation with no bias (data not shown).

Antibody-Dependent Cellular Phagocytosis (ADCP) Assay

Functional non-neutralizing antibody responses were measured using immunoglobulin G (IgG) antibodies purified from serum samples obtained at week 28 from the treated NHPs. IgG was purified using Melon Gel columns (Thermo Scientific), and quantitated using a Nanodrop spectrophotometer (Thermo Scientific). ADCP assays were performed as described in Ackerman et al. (2011) (A robust, high-throughput assay to determine the phagocytic activity of clinical antibody samples. *J. Immunol. Methods* 366, 8-19), which is incorporated by reference herein in its entirety.

More specifically, Glade C (C97) Env (SEQ ID NO: 5) and Mosaic M (mos 1) (SEQ ID NO: 6) Env biotinylated antigen were incubated with 1μm yellow-green fluorescent neutravidin beads (Invitrogen) overnight. The beads were then washed and resuspended at a final dilution of 1:100 in Phosphate Buffered Saline-Bovine Serum Albumin (PBS-BSA). Antibodies purified from the serum samples and $9 \times 10^5$ antigen-labelled beads were mixed in a round-bottom 96-well plate, and the plate was incubated for 2 hours. Human monocytic cells derived from acute myeloid leukemia (THP-1 cells; $2 \times 10^4$ cells) were then added to each well in a final volume of 200 μL, and the plate was incubated overnight.

The next day, half the culture volume was removed and replaced with 100 μL of 4% paraformaldehyde before the plates were analyzed on a BD LSR II Flow Cytometer equipped with an HTS plate reader. For analysis, the samples were gated on live cell, and the proportion of THP-1 cells phagocytosing beads was determined. A phagocytic score was calculated as follows: (percent bead positive) multiplied by (mean fluorescense intensity bead positive).

Figure 2:
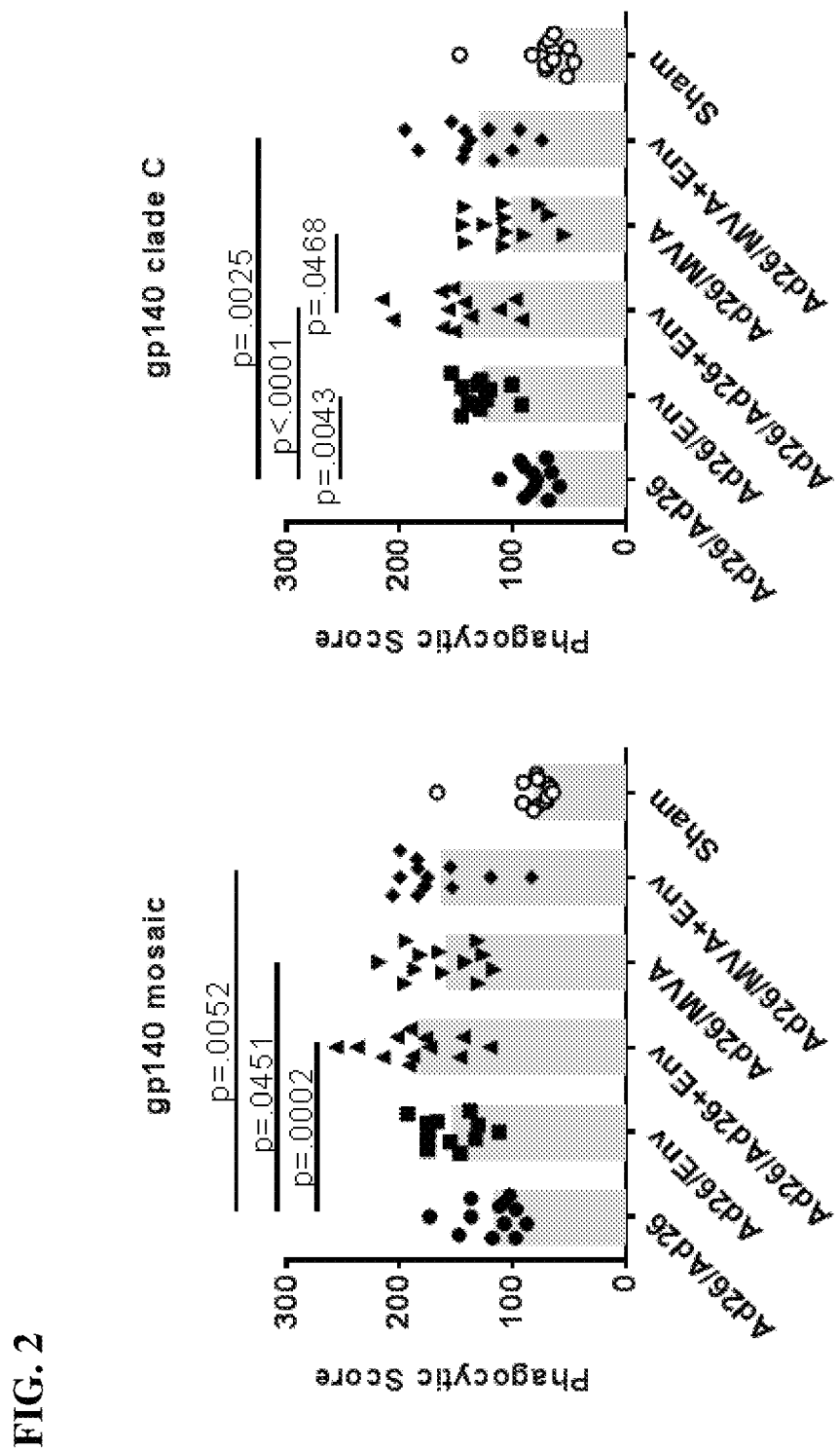
FIG. 2 shows the results from an antibody-dependent cellular phagocytosis (ADCP) assay on immunoglobulin G (IgG) antibodies purified from serum samples obtained at week 28 from the vacinnated NHPs using biotinylated Glade C Env and mosaic Env antigens; the phagocytic score responses of individual animals are shown; symbols represent the score values from the individual animals tested and gray columns indicate group geometric mean titers.

The results obtained in the ADCP Assay at week 28 are summarized in FIG. 2, which shows the phagocytic score responses of individual animals. Statistical analyses of data were performed by nonparametric comparisons for all pairs using the Dunn method for joint ranking.

Clade C gp140 Env and Mosaic M Env antigens displayed good correlation with no bias, which are consistent with the results from the ELISA assay described above, and the neutralizing antibody (nAb) assay described below.

Neutralizing Antibody (nAb) Assay

Neutralizing antibody (nAb) responses against tier 1 HIV-1 Env pseudoviruses were measured using luciferase-based virus neutralization assays in TZM.b1 cells. Specifically, viruses in the tier 1 panel included MW965.26 (clade C), SF162.LS (clade B), MN-3 (clade A), DJ263.8 (clade A), and BaL.26 (clade B).

Briefly, 96-well flat bottomed-plates were coated with serum samples obtained from the NHPs at week 56, and three-fold dilutions of the serum samples in 100 μL of 10% Dulbecco's Modified Eagle Medium (DMEM) were made. Then, 200 $TCID_{50}$ of virus (tissue culture infectious dose, or the amount of a pathogenic agent that will produce pathological change in 50% of cell cultures inoculated) was added to each well in a volume of 50 μL. The plates were incubated for 1 hour at 37° C. TZM.b1 cells were then added at $1 \times 10^4$ cells/well in a volume of 100 μL 10% DMEM containing DEAE-Dextran (Sigma) at a final concentration of 11 μg/mL.

The $IC_{50}$ was calculated as the serum dilution that resulted in 50% reduction in relative luminescence units as compared to undiluted virus control, after the subtraction of cell control relative luminescence units (TZM.b1 cells with no virus present).

Figure 3:
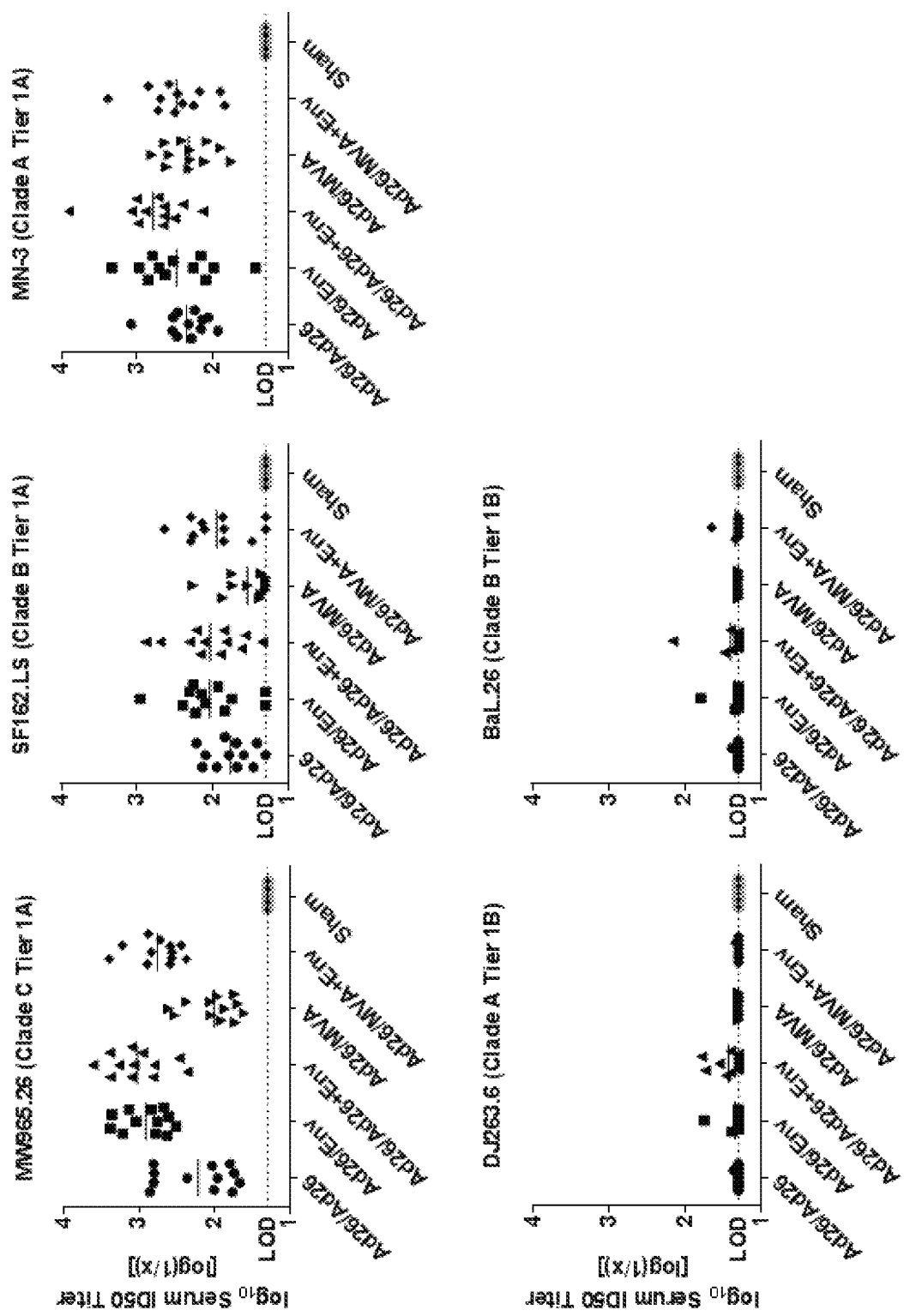
FIG. 3 shows the results from a neutralizing antibody (nAb) assay on serum samples obtained at week 56 from the vacinnated NHPs in TZM-b1 cells against tier 1 Env HIV-1 pseudoviruses; the tier 1 Env HIV-1 pseudoviruses tested included MW965.26 (Glade C), SF162.LS (Glade B), MN-3 (Glade A), DJ263.8 (Glade A), and BaL.26 (Glade B); symbols represent login-transformed $ID_{50}$ (median infective dose) titers from individual animals with group geometric mean titers indicated as horizontal lines.

The results from the HIV-1 tier 1 TZM-b1 neutralization assays against MW965.26 (clade C), SF162.LS (clade B), MN-3 (clade A), DJ263.8 (clade A), and BaL.26 (clade B) in samples obtained from the NHPs at week 56 are shown in FIG. 3. Symbols represent $\log_{10}$-transformed $ID_{50}$ titers from the individual animals tested with group geometric mean titers indicated as horizontal lines. The results from the nAb assay are consistent with the results from the ELISA assay.

ELISPOT Assay

HIV-1-specific cellular immune responses were assessed by IFN-γ ELISPOT assays as previously described in Liu et al., 2009, *Nature* 457: 87-91, which is herein incorporated by reference in its entirety. ELISPOT assays utilized pools of HIV-1 potential T-cell epitope (PTE) peptides covering global potential human T cell epitopes. In earlier studies, analyses of cellular immune breadth utilized subpools of 10-16 peptides covering each antigen followed by epitope mapping using individual peptides, essentially as previously reported in Barouch et al., 2010, *Nat. Med.* 16:319-323 [54], which is incorporated by reference herein in its entirety. Epitope-specific CD8+ and CD4+ T lymphocyte responses were determined by cell depletion studies.

Figure 4:
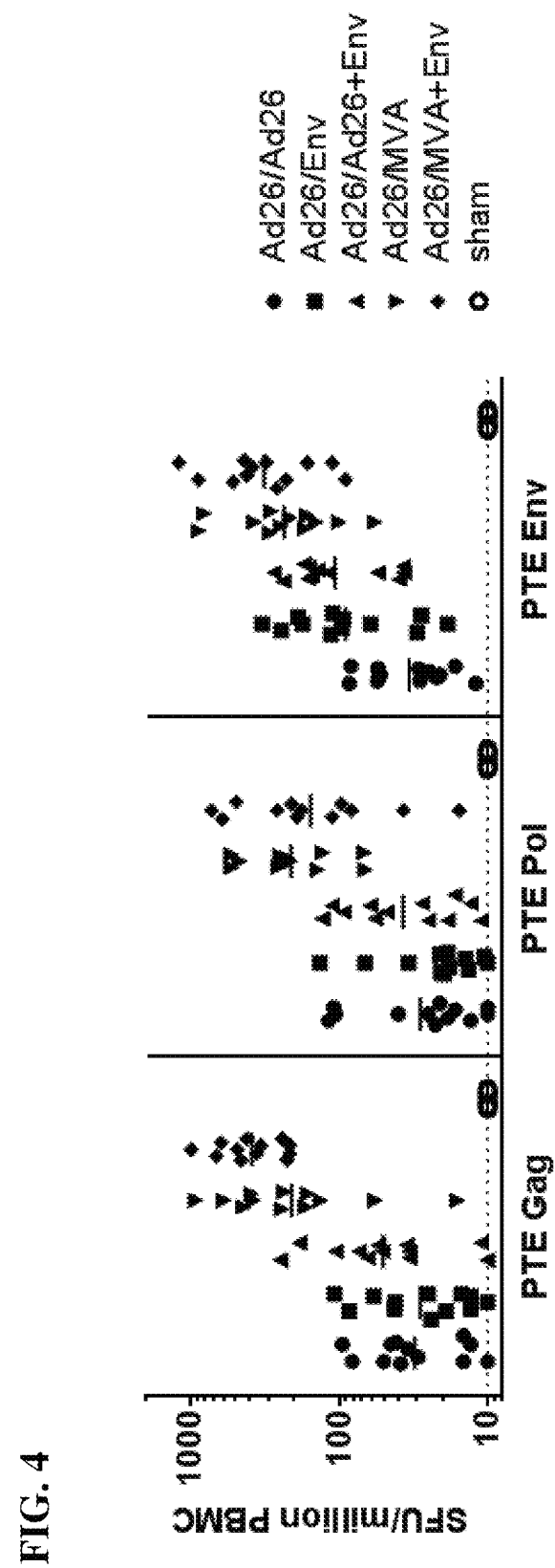
FIG. 4 shows the results from an IFN-γ Enzyme-Linked Immunospot (ELISPOT) Assay on samples obtained at week 54 from the vacinnated NHPs using global potential T-cell epitope (PTE) peptide pools; the results are shown as mean spot-forming units (SFU) per $10^6$ peripheral blood mononuclear cells (PBMCs); symbols represent the values for individual animals; horizontal lines indicate group geometric mean values and the dotted line represents the lower threshold of detection.

Briefly, immunogenicity of the treated NHPs was assessed in samples obtained at week 54 by IFN-γ ELISPOT assays using PTE peptide pools. Peripheral blood mononuclear cells (PBMCs) were stimulated with the PTE peptide pools, and after incubation, the cells were washed, labeled, and developed to visualize spot forming cells. The results of the ELISPOT assay, expressed as mean spot-forming units (SFU) per $10^6$ PBMC, are shown in FIG. 4.

Study Conclusions

As shown by the results of the animal studies described above and as summarized in FIGS. 1-4, the combination of rAd vectors and/or MVA vectors with isolated antigenic polypeptide in prime-boost combinations is useful for raising broad HIV- specific humoral and cellular immune responses in primates. Specifically, the utility of incorporating a gp140 protein in one or more boosting immunizations in raising broad HIV-specific humoral and cellular immune responses in primates was demonstrated. Moreover, all vaccine regimens tested were shown to be immunogenic in all immunized animals (Group II-V).

In particular, the administration of one or more rAd26 vectors (week 0 and 12) expressing one or more HIV-1 antigens followed by a boosting immunization at weeks 24 and 52 with rAd26 vectors or MVA vectors and an isolated Glade C gp140 protein, resulted in efficient boosting of the humoral response to HIV-1, as shown by the results of the ELISA and ADCP assays (see FIGS. 1A, 1B, and 2, specifically Group III (labeled "Ad26/Ad26+Env") and Group V (labeled "Ad26/MVA+Env")). Furthermore, administration of one or more rAd26 vectors, followed by a boosting immunization at weeks 24 and 52 with MVA vectors with or without Glade C gp140 protein was able to significantly increase cellular immune responses as measured by ELISPOT assay (see FIG. 4, specifically Group IV (labeled "Ad26/MVA") and Group V (labeled "Ad26/MVA+Env")).

Example 2. Study of HIV Vaccine Regimens in Humans

The following multicenter, randomized, parallel group, placebo-controlled, double-blind clinical study in healthy HIV-uninfected adult men and women is performed: A Phase 1/2a Study to Evaluate the Safety/Tolerability and Immunogenicity of Homologous Ad26 Mosaic Vector Vaccine Regimens or Ad26 Mosaic and MVA Mosaic Heterologous Vector Vaccine Regimens, with High-Dose, Low-Dose or no Clade C gp140 Protein Plus Adjuvant for HIV Prevention. This study is ongoing.

Overall Rationale

A study is performed to assess the safety/tolerability and immunogenicity of seven prime-boost vaccine regimens. Subjects receive four doses of study vaccine: $Ad26_{mos}$ or placebo is given at weeks 0 and 12; and $Ad26_{mos}$ or $MVA_{mos}$, both with or without glycoprotein 140 drug product (low or high dose), or placebo only is given at Weeks 24 and 48.

Study vaccines used are Ad26mos, MVAmos and gp140 DP as follows (see also Example 1):

(i) $Ad26_{mos}$ is composed of the following three vaccine products supplied in the same vial and administered in a 2:1:1 ratio: Ad26.Mos1Env, Ad26.Mos1Gag-Pol, and Ad26.Mos2Gag-Pol expressing HIV-1 mosaic Env 1 (SEQ ID NO: 1), mosaic GagPol1 (SEQ ID: NO 3), and mosaic GagPol2 (SEQ ID NO: 4) genes, respectively;

(ii) $MVA_{mos}$ is composed of the following two vaccine products supplied in separate vials and administered in a 1:1 ratio: MVA-Mosaic1 (MVA virus expressing Mosaic1 HIV-1 Gag, Pol, and Env proteins having SEQ ID NOs: 1 and 3) and MVA-Mosaic2 (MVA virus expressing Mosaic2 HIV-1 Gag, Pol, and Env proteins having SEQ ID NOs: 2 and 4); and (iii) gp140 drug product contains HIV-1 Clade C glycoprotein 140 (recombinant trimeric gp140 having SEQ ID NO: 5), produced by a transformed PER.C6® cell line constructed to produce gp140. In this study, gp140 drug product is dosed with aluminum phosphate as adjuvant, and the dosed gp140 drug product is simply referred to as "gp140 DP."

Objectives

The primary objectives of the study include (1) assessing the safety/tolerability of various prime-boost regimens containing $Ad26_{mos}$, $MVA_{mos}$, and/or gp140 DP components; and (2) comparing HIV Env binding antibody responses between the different vaccine regimens.

The secondary objective of the study includes assessing other antibody binding, antibody effector function and antibody characterization, and cellular responses.

The exploratory objectives of the study include (1) exploring immune responses to the different vaccine regimens in mucosal secretions in a subset of subjects; (2) exploring gene expression patterns between the different vaccine regimens; and (3) exploring neutralization antibodies against the Ad26 vectors.

Vaccination and Experimental Design

The study comprises a 48-week vaccination period during which subjects are vaccinated at baseline (Week 0), Week 12 and Week 24, with a booster at Week 48, and a 48-week follow-up period to a final visit at Week 96. Vaccinations are administered as shown in Table 1B, and blood samples are taken at specific clinic visits to assess immune responses.

A long-term follow-up period (approximately 2 years after Week 96) will continue for subjects randomized to the regimen that are subsequently selected for future studies, based on the analysis of the Week 28 data. If the Week 28 data are inconclusive, then Week 52 data is taken into consideration in regimen selection. In the event that no clear decision can be made, this extended follow-up period can include subjects from more than one group with the purpose of assessing durability of immune responses. The end of the study is the last subject's final visit.

TABLE 1B

Vaccine regimens tested on humans

| Group | N | Week 0 (baseline) | Week 12 | Week 24 | Week 48 booster |
|---|---|---|---|---|---|
| Group 1 | 50 | $Ad26_{mos}$ | $Ad26_{mos}$ | $Ad26_{mos}$ + gp140 DP (250 µg protein/adj*) | $Ad26_{mos}$ + gp140 DP (250 µg protein/adj*) |
| Group 2 | 50 | $Ad26_{mos}$ | $Ad26_{mos}$ | $Ad26_{mos}$ + gp140 DP (50 µg protein/adj*) | $Ad26_{mos}$ + gp140 DP (50 µg protein/adj*) |
| Group 3 | 50 | $Ad26_{mos}$ | $Ad26_{mos}$ | $Ad26_{mos}$ | $Ad26_{mos}$ |
| Group 4 | 50 | $Ad26_{mos}$ | $Ad26_{mos}$ | $MVA_{mos}$ + gp140 DP (250 µg protein/adj*) | $MVA_{mos}$ + gp140 DP (250 µg protein/adj*) |
| Group 5 | 50 | $Ad26_{mos}$ | $Ad26_{mos}$ | $MVA_{mos}$ + gp140 DP (50 µg protein/adj*) | $MVA_{mos}$ + gp140 DP (50 µg protein/adj*) |
| Group 6 | 50 | $Ad26_{mos}$ | $Ad26_{mos}$ | $MVA_{mos}$ | $MVA_{mos}$ |
| Group 7 | 50 | $Ad26_{mos}$ | $Ad26_{mos}$ | gp140 DP (250 µg protein/adj*) | gp140 DP (250 µg protein/adj*) |
| Group 8 | 50 | Placebo | Placebo | Placebo | Placebo |

*adj is AdjuPhos ® (sterilized aluminum phosphate wet gel suspension; used as adjuvant for gp140; aluminum content is 0.425 mg/0.5 mL dose; 50 µg (low dose) and 250 µg (high dose) refer to total protein content of gp140 protein.

Dosage and Administration

Subjects receive doses of study vaccine at four time points according to randomization, on Day 1 of Week 0, at Week 12, and at Week 24, with a booster at Week 48, administered by intramuscular injection into the deltoid. For visits with only one injection (i.e., at Weeks 0 and 12), either deltoid can be used for the injection. When two study vaccine injections are given at one visit (i.e., at Weeks 24 and 48), a different deltoid is used for each injection (with exceptions allowed upon medical indication). Study vaccines with the administered doses are as follows:

(i) Ad26mos (Ad26.Mos1Env+Ad26.Mos1Gag-Pol+Ad26.Mos2Gag-Pol): Total dose is $5\times10^{10}$ viral particles (vp) per 0.5 mL injection (ii) $MVA_{mos}$ (MVA-Mosaic1+MVA-Mosaic2): Total dose is $10^8$ plaque-forming units (pfu) per 0.5 mL injection (iii) gp140 DP:

Low-dose: gp140 DP with 50 μg total protein, mixed with aluminum phosphate adjuvant (0.425 mg aluminum) at the pharmacy, per 0.5 mL injection High-dose: gp140 DP with 250 μg total protein, mixed with aluminum phosphate adjuvant (0.425 mg aluminum) at the pharmacy, per 0.5 mL injection (iv) Placebo:

0.9% saline, 0.5 mL injection

Immunogenicity Evaluations

Assays are performed to evaluate humoral immune responses including, but not limited to: Env-specific serum binding antibody assay, nAb assays, and antibody-dependent cellular phagocytosis (ADCP) assay, as well as epitope mapping (see Table 2).

TABLE 2

Humoral Immune Response Assays

| Objective/ endpoint | System | Assay/Method | Readout | Timepoint |
|---|---|---|---|---|
| Primary | Serum | Env binding antibody (ELISA) | Titer or % responders (Clade C) and breadth (Clade A, B, C) | Baseline 1 mo post-vac. 1 0.5, 1 mo post-vac. 2-4 3, 6 mo post-vac. 4 |
| Secondary | Serum | HIV neutralizing antibody | Tier 1 and Tier $2^a$ nAbs: GMT for each isolate, % responders to each isolate Breadth: # isolates neutralized | As above |
| Secondary | Serum | gp120 binding antibody | Anti-gp120 titer (Clade A, B, C) | As above |
| Secondary | Serum | | | As above |
| Secondary | Serum | ADCP Isotyping Env binding antibody (ELISA) | % phagocytosis Isotyping (Clade C) (IgA, IgG1, IgG2, IgG3) | As above |
| Exploratory | Serum | Epitope mapping | Targeted epitopes and diversity (including V2) | 1 mo post-vac. 1-4 At vac. 2-4 |
| Exploratory | Serum | Ad26 neutralization antibodies | Titers of Ad26 neutralization antibodies | 1 mo post-vac. 1-4 3, 7.5, 12 mo post-vac. 4 At vac. 1-4 |

ADCP = antibody-dependent cellular phagocytosis;
ELISA = enzyme-linked immunosorbent assay;
GMT = geometric mean titer;
Ig = immunoglobulin;
mo = month;
nAb = neutralizing antibody;
vac = vaccination
$^a$Classification of HIV-1 viruses according to sensitivity to antibody-mediated neutralization: very high (tier 1A), above-average (tier 1B), moderate (tier 2), or low (tier 3) [1]. Tier 2 will only be assessed if Tier 1 shows positive results Assays are performed to evaluate cellular immune responses including, but not limited to: ELISPOT, intracellular cytokine staining, and multi-parameter flow cytometry (see Table 3).

TABLE 3

T-Cell Immune Response Assays

| Objective/ endpoint | System | Assay/Method | Readout | Timepoint |
|---|---|---|---|---|
| Secondary | PBMC | ELISPOT | Breadth and depth: # peptides, % responders, median response | Baseline 0.5, 1 mo post-vac. 3 & 4 |
| Exploratory | PBMC | Intracellular cytokine staining | % of CD4 and CD8+ T cells producing IFNγ, IL-2, TNFα | Baseline 1 mo post-vac. 1 0.5, 1 mo post-vac. 2-4 3, 7.5 mo post-vac. 4 |

TABLE 3-continued

T-Cell Immune Response Assays

| Objective/endpoint | System | Assay/Method | Readout | Timepoint |
|---|---|---|---|---|
| Exploratory | PBMC | Multi-parameter flow cytometry | Characterization of memory T-cell development with emphasis on follicular helper T cells | Baseline<br>1 mo post-vac. 1<br>0.5, 1 mo post-vac. 2-4<br>3, 7.5 mo post-vac. 4 |
| Exploratory | PBMC | Gene expression analysis | Regulation of genes (clusters) that predict specific immune responses and HLA typing | Baseline<br>1 mo post-vac. 1<br>0.5, 1 mo post-vac. 2-4<br>3, 7.5 mo post-vac. 4 |

ELISPOT = enzyme-linked immunospot assay;
HLA = human leukocyte antigen;
IFNγ = interferon gamma;
IL-2 = interleukin 2;
mo = month;
PBMC = peripheral blood mononuclear cell;
TNFα = tumor necrosis factor alpha;
vac = vaccination
Note:
HLA only tested once (using the baseline blood sample)

Example 3. Further Studies of HIV Vaccine Regimens in Humans

Further clinical studies in humans are conducted to assess safety/tolerability and immunogenicity of different vaccine schedules with rAd26 vectors expressing mosaic HIV antigens and isolated Clade C gp140 trimeric protein in healthy HIV-uninfected subjects. In particular, shorter regimens and fewer dosing regimens are tested as compared to the study described in Example 2. Optimizing the vaccine schedule can increase compliance with the complete schedule and/or be simpler in use and easier to administer.

Vaccination and Experimental Design

A single-center, randomized, parallel-group, placebo-controlled, double-blind Phase 1 clinical study in healthy HIV-uninfected adult men and women aged 18 to 50 years is performed. A target of 36 human subjects are participating in this study. The subjects are divided into three groups (Groups 1 to 3) with 12 subjects randomized to each group. Subjects in each group are further randomized into two subgroups: Subgroup A (10 subjects) and Subgroup B (2 subjects).

The subjects in Subgroup A receive the study vaccine, and the subjects in Subgroup B receive placebo. Subjects are enrolled in the study regardless of their baseline Ad26 seropositivity.

The study comprises a maximum vaccination period of 48 weeks, and a post-vaccination follow-up period until Week 72. Subjects receive the study vaccines or placebo according to the schedules in Table 4 below. See Example 2 for a description of the vaccine compositions used in the study.

TABLE 4

Schedule for administration of study vaccines in the study

| Group | N | Week 0 | Week 8 | Week 12 | Week 24 | Week 48 |
|---|---|---|---|---|---|---|
| 1A | 10 | Ad26$_{mos}$ | | Ad26$_{mos}$ | Ad26$_{mos}$ + gp140 DP (250 µg protein/adj) | Ad26$_{mos}$ + gp140 DP (250 µg protein/adj) |
| 1B | 2 | Placebo | | Placebo | Placebo + Placebo | Placebo + Placebo |
| 2A | 10 | Ad26$_{mos}$ + gp140 DP (250 µg protein/adj) | | | Ad26$_{mos}$ + gp140 DP (250 µg protein/adj) | Ad26$_{mos}$ + gp140 DP (250 µg protein/adj) |
| 2B | 2 | Placebo + Placebo | | | Placebo + Placebo | Placebo + Placebo |
| 3A | 10 | Ad26$_{mos}$ | Ad26$_{mos}$ + gp140 DP (250 µg protein/adj) | | | Ad26$_{mos}$ + gp140 DP (250 µg protein/adj) |
| 3B | 2 | Placebo | Placebo + Placebo | | | Placebo + Placebo |

Group 1 represents the "base-case" regimen, which allows bridging of data from this study to the study in Example 2. Subjects in Group 1 are administered four vaccinations at Weeks 0, 12, 24, and 48, which is the same dosing schedule as the subjects in Group 1 of the study in Example 2 (see Table 1B in Example 2). Groups 2 and 3 receive three vaccinations over 24 weeks (Group 2: Weeks 0, 12, and 24; Group 3: Weeks 0, 8, and 24). Blood samples are taken at specific clinic visits to assess immune responses.

More specifically, Group 2 explores a shorter, more convenient regimen by removing the need for the subject to return to the clinic for a late boost at Week 48, unlike the "base-case".

Group 3 examines the ability of rAd26 vectors to prime for a qualitatively similar response as the full regimen, while attaining immunogenicity levels that are superior to that of the "base-case" regimen post-Week 24 due to an extra dose of gp140 DP at the second vaccination.

An interim analysis (blinded) is performed once all subjects complete the Week 28 visit or discontinued earlier. The primary analysis (unblinded) is performed once all subjects complete the Week 52 visit or discontinued earlier. The final analysis is performed once all subjects complete their final study visit at Week 72.

Example 4. Additional Studies of HIV Vaccine Regimens in Humans

Further clinical studies in humans are also conducted to assess safety/tolerability and immunogenicity of different vaccine schedules with MVA vectors and Clade C gp140 trimeric protein in healthy HIV-uninfected subjects, wherein shorter dosing regimens and regimens having fewer doses are tested as compared to the study in Example 2. Subjects receive the study vaccines or placebo according to the schedules in Table 5 below. The vaccine compositions used in the study are as described in Example 2. The study participants are randomized as described above for the study in Example 3.

TABLE 5

Schedule for administration of study vaccines in the study

| Group | Week 0 | Week 8 | Week 12 | Week 24 | Week 48 |
|---|---|---|---|---|---|
| 1A | $Ad26_{mos}$ | | $Ad26_{mos}$ | $MVA_{mos}$ + gp140 DP (250 µg protein/adj) | $MVA_{mos}$ + gp140 DP (250 µg protein/adj) |
| 1B | Placebo | | Placebo | Placebo + Placebo | Placebo + Placebo |
| 2A | $Ad26_{mos}$ + gp140 DP (250 µg/adj) | | | $MVA_{mos}$ + gp140 DP (250 µg protein/adj) | $MVA_{mos}$ + gp140 DP (250 µg protein/adj) |
| 2B | Placebo + Placebo | | | Placebo + Placebo | Placebo + Placebo |
| 3A | $Ad26_{mos}$ | $MVA_{mos}$ + gp140 DP (250 µg protein/adj) | | | $MVA_{mos}$ + gp140 DP (250 µg protein/adj) |
| 3B | Placebo | Placebo + Placebo | | | Placebo + Placebo |

The first group (Group 1) again represents the "base-case" regimen, which allows bridging of data from this study to the study in Example 2. Subjects are administered four vaccinations at Weeks 0, 12, 24, and 48, which is the same dosing schedule as the subjects in Group 4 of the study in Example 2 (see Table 1B in Example 2). The other groups (Groups 2 and 3) receive shorter regimens, and are vaccinated at weeks 0, 8 or 12, and 24. Priming in this study is with Ad26 vectors, and boosting is with MVA vectors. Possible advantages of these regimens include greater convenience with the shorter duration (24 weeks total) as compared to the regimen in Group 1 (48 weeks total). Blood samples are taken at specific clinic visits to assess immune responses.

It is understood that the examples and embodiments described herein are for illustrative purposes only, and that changes could be made to the embodiments described above without departing from the broad inventive concept thereof. It is understood, therefore, that this invention is not limited to the particular embodiments disclosed, but it is intended to cover modifications within the spirit and scope of the invention as defined by the appended claims.

REFERENCES

1. Gurwith, M., et al., Safety and immunogenicity of an oral, replicating adenovirus serotype 4 vector vaccine for H5N1 influenza: a randomised, double-blind, placebo-controlled, phase 1 study. Lancet Infect Dis, 2013. 13(3): p. 238-50.
2. Centers for Disease, Control, and Prevention, Vital signs: HIV prevention through care and treatment—United States. MMWR Morb Mortal Wkly Rep, 2011. 60(47): p. 1618-23.
3. Centlivre, M., et al., In HIV-1 pathogenesis the die is cast during primary infection. AIDS, 2007. 21(1): p. 1-11.
4. Wawer, M. J., et al., Rates of HIV-1 transmission per coital act, by stage of HIV-1 infection, in Rakai, Uganda. J Infect Dis, 2005. 191(9): p. 1403-9.
5. Flynn, N. M., et al., Placebo-controlled phase 3 trial of a recombinant glycoprotein 120 vaccine to prevent HIV-1 infection. J Infect Dis, 2005. 191(5): p. 654-65.
6. Pitisuttithum, P., et al., Randomized, double-blind, placebo-controlled efficacy trial of a bivalent recombinant glycoprotein 120 HIV-1 vaccine among injection drug users in Bangkok, Thailand. J Infect Dis, 2006. 194(12): p. 1661-71.
7. Gray, G. E., et al., Safety and efficacy of the HVTN 503/Phambili study of a clade-B-based HIV-1 vaccine in South Africa: a double-blind, randomised, placebo-controlled test-of-concept phase 2b study. Lancet Infect Dis, 2011. 11(7): p. 507-15.
8. Buchbinder, S. P., et al., Efficacy assessment of a cell-mediated immunity HIV-1 vaccine (the Step Study): a double-blind, randomised, placebo-controlled, test-of-concept trial. Lancet, 2008. 372(9653): p. 1881-93.

9. Rerks-Ngarm, S., et al., Vaccination with ALVAC and AIDSVAX to prevent HIV-1 infection in Thailand. N Engl J Med, 2009. 361(23): p. 2209-20.

10. McElrath, M. J., et al., HIV-1 vaccine-induced immunity in the test-of-concept Step Study: a case-cohort analysis. Lancet, 2008. 372(9653): p. 1894-905.

11. Abbink, P., et al., Comparative seroprevalence and immunogenicity of six rare serotype recombinant adenovirus vaccine vectors from subgroups B and D. J Virol, 2007. 81(9): p. 4654-63.

12. Vogels, R., et al., Replication-deficient human adenovirus type 35 vectors for gene transfer and vaccination: efficient human cell infection and bypass of preexisting adenovirus immunity. J Virol, 2003. 77(15): p. 8263-71.

13. Farina, S. F., et al., Replication-defective vector based on a chimpanzee adenovirus. J Virol, 2001. 75(23): p. 11603-13.

14. Barouch, D. H., et al., International seroepidemiology of adenovirus serotypes 5, 26, 35, and 48 in pediatric and adult populations. Vaccine, 2011. 29: p. 5203-5209.

15. Mast, T. C., et al., International epidemiology of human pre-existing adenovirus (Ad) type-5, type-6, type-26 and type-36 neutralizing antibodies: correlates of high Ad5 titers and implications for potential HIV vaccine trials. Vaccine, 2010. 28(4): p. 950-7.

16. Chen, H., et al., Adenovirus-based vaccines: comparison of vectors from three species of adenoviridae. J Virol, 2010. 84(20): p. 10522-32.

17. Thorner, A. R., et al., Age dependence of adenovirus-specific neutralizing antibody titers in individuals from sub-Saharan Africa. J Clin Microbiol, 2006. 44(10): p. 3781-3.

18. Sprangers, M. C., et al., Quantifying adenovirus-neutralizing antibodies by luciferase transgene detection: addressing preexisting immunity to vaccine and gene therapy vectors. J Clin Microbiol, 2003. 41(11): p. 5046-52.

19. Waddington, S. N., et al., Adenovirus serotype 5 hexon mediates liver gene transfer. Cell, 2008. 132(3): p. 397-409.

20. Liu, J., et al., Magnitude and phenotype of cellular immune responses elicited by recombinant adenovirus vectors and heterologous prime-boost regimens in rhesus monkeys. J Virol, 2008. 82(10): p. 4844-52.

21. Liu, J., et al., Immune control of an SIV challenge by a T-cell-based vaccine in rhesus monkeys. Nature, 2009. 457(7225): p. 87-91.

22. Lore, K., et al., Myeloid and plasmacytoid dendritic cells are susceptible to recombinant adenovirus vectors and stimulate polyfunctional memory T cell responses. J Immunol, 2007. 179(3): p. 1721-9.

23. unpublished, Barouch.et al.

24. Barouch et al.,.. in AIDS Vaccine. 2009. Paris, France.

25. Kuschner, R. A., et al., A phase 3, randomized, double-blind, placebo-controlled study of the safety and efficacy of the live, oral adenovirus type 4 and type 7 vaccine, in U.S. military recruits. Vaccine, 2013. 31(28): p. 2963-71.

26. Masopust, D. and L. J. Picker, Hidden memories: frontline memory T cells and early pathogen interception. J Immunol, 2012. 188(12): p. 5811-7.

27. Bell, J. A., et al., Illness and microbial experiences of nursery children at junior village. American Journal of Hygiene, 1961. 74: p. 267-292.

28. Rhee, E. G. and D. H. Barouch, Adenoviruses, in Principles and Practice of Infectious Diseases, G. L. Mandell, J. E. Bennett, and R. Dolin, Editors. 2010, Elsevier: Philadelphia, Pa.

29. Brandt, C. D., et al., Infections in 18,000 infants and children in a controlled study of respiratory tract disease. I. Adenovirus pathogenicity in relation to serologic type and illness syndrome. Am J Epidemiol, 1969. 90(6): p. 484-500.

30. Fox, J. P., et al., The virus watch program: a continuing surveillance of viral infections in metropolitan New York families. VI. Observations of adenovirus infections: virus excretion patterns, antibody response, efficiency of surveillance, patterns of infections, and relation to illness. Am J Epidemiol, 1969. 89(1): p. 25-50.

31. Fox, J. P., C. E. Hall, and M. K. Cooney, The Seattle Virus Watch. VII. Observations of adenovirus infections. Am J Epidemiol, 1977. 105(4): p. 362-86.

32. Noel, J., et al., Identification of adenoviruses in faeces from patients with diarrhoea at the Hospitals for Sick Children, London, 1989-1992. J Med Virol, 1994. 43(1): p. 84-90.

33. Faden, H., et al., Pediatric adenovirus infection: relationship of clinical spectrum, seasonal distribution, and serotype. Clin Pediatr (Phila), 2011. 50(6): p. 483-7.

34. Abbas, K. Z., et al., Temporal changes in respiratory adenovirus serotypes circulating in the greater Toronto area, Ontario, during December 2008 to April 2010. Virol J, 2013. 10: p. 15.

35. Diarrhea: Why children are still dying and what can be done, 2009, The United Nations Chidlren's Fund (UNICEF)/World Health Organization (WHO): New York, N.Y.

36. Ramani, S. and G. Kang, Viruses causing childhood diarrhoea in the developing world. Curr Opin Infect Dis, 2009. 22(5): p. 477-82.

37. Kotloff, K. L., et al., Burden and aetiology of diarrhoeal disease in infants and young children in developing countries (the Global Enteric Multicenter Study, GEMS): a prospective, case-control study. Lancet, 2013. 382(9888): p. 209-22.

38. Magwalivha, M., et al., High prevalence of species D human adenoviruses in fecal specimens from Urban Kenyan children with diarrhea. J Med Virol, 2010. 82(1): p. 77-84.

39. Liu, L. Y., et al., [Investigation of adenovirus infection in hospitalized children with diarrhea during 2010 in Beijing, China]. Zhonghua Er Ke Za Zhi, 2012. 50(6): p. 450-4.

40. Ouyang, Y., et al., Etiology and epidemiology of viral diarrhea in children under the age of five hospitalized in Tianjin, China. Arch Virol, 2012. 157(5): p. 881-7.

41. Lee, J. I., et al., Detection and molecular characterization of adenoviruses in Korean children hospitalized with acute gastroenteritis. Microbiol Immunol, 2012. 56(8): p. 523-8.

42. Espinola, E. E., et al., Genetic diversity of human adenovirus in hospitalized children with severe acute lower respiratory infections in Paraguay. J Clin Virol, 2012. 53(4): p. 367-9.

43. Mast, T. C., et al., International epidemiology of human pre-existing adenovirus (Ad) type-5, type-6, type-26 and type-36 neutralizing antibodies: correlates of high Ad5 titers and implications for potential HIV vaccine trials. Vaccine, 2010. 28: p. 950-957.

44. Kasel, J. A., et al., Conjunctivitis and enteric infection with adenovirus types 26 and 27: responses to primary, secondary and reciprocal cross-challenges. Am J Hyg, 1963. 77: p. 265-82.

45. Hierholzer, J. C., et al., Adenoviruses from patients with AIDS: a plethora of serotypes and a description of five new serotypes of subgenus D (types 43-47). J Infect Dis, 1988. 158(4): p. 804-13.

46. Khoo, S. H., et al., Adenovirus infections in human immunodeficiency virus-positive patients: clinical features and molecular epidemiology. J Infect Dis, 1995. 172(3): p. 629-37.

47. Curlin, M. E., et al., Frequent detection of human adenovirus from the lower gastrointestinal tract in men who have sex with men. PLoS One, 2010. 5(6): p. e11321.

48. Dubberke, E. R., et al., Acute meningoencephalitis caused by adenovirus serotype 26. J Neurovirol, 2006. 12(3): p. 235-40.

49. Koneru, B., et al., Adenoviral infections in pediatric liver transplant recipients. JAMA, 1987. 258(4): p. 489-92.

50. Venard, V., et al., Genotyping of adenoviruses isolated in an outbreak in a bone marrow transplant unit shows that diverse strains are involved. J Hosp Infect, 2000. 44(1): p. 71-4.

51. Al Qurashi, Y. M., M. Guiver, and R. J. Cooper, Sequence typing of adenovirus from samples from hematological stem cell transplant recipients. J Med Virol, 2011. 83(11): p. 1951-8.

52. Janes, H., et al., MRKAd5 HIV-1 Gag/Pol/Nef vaccine-induced T-cell responses inadequately predict distance of breakthrough HIV-1 sequences to the vaccine or viral load. PLoS One, 2012. 7(8): p. e43396.

53. Fischer, W., et al., Polyvalent vaccines for optimal coverage of potential T-cell epitopes in global HIV-1 variants. Nat Med, 2007. 13(1): p. 100-6.

54. Barouch, D. H., et al., Mosaic HIV-1 vaccines expand the breadth and depth of cellular immune responses in rhesus monkeys. Nat Med, 2010. 16(3): p. 319-23.

55. Santra, S., et al., Mosaic vaccines elicit CD8+T lymphocyte responses that confer enhanced immune coverage of diverse HIV strains in monkeys. Nat Med, 2010. 16(3): p. 324-8.

56. Li, Q., et al., Visualizing antigen-specific and infected cells in situ predicts outcomes in early viral infection. Science, 2009. 323(5922): p. 1726-9.

57. Baden, L. R., et al., First-in-human evaluation of the safety and immunogenicity of a recombinant adenovirus serotype 26 HIV-1 Env vaccine (IPCAVD 001). J Infect Dis, 2013. 207(2): p. 240-7.

58. Barouch, D. H., et al., Characterization of humoral and cellular immune responses elicited by a recombinant adenovirus serotype 26 HIV-1 Env vaccine in healthy adults (IPCAVD 001). J Infect Dis, 2013. 207(2): p. 248-56.

59. WO 2010/042942 entitled "Biochemically stabilized HIV-1 ENV Trimer Vaccine"

60. Kovacs et al, "HIV-1 envelope trimer elicits more potent neutralizing antibody responses than monomeric gp120," PNAS 2012, 109(30):12111-6.

61. Havenga, et al., (2006) *J Gen Virol* 87(Pt 8): 2135-43.

62. Jin, et al., *Vaccine* 28(27): 4369-75.

63. de Gruijl, et al., (2006) *J Immunol* 177(4): 2208-15.

64. Haslett et al. *Journal of Infectious Diseases* 181 : 1264-72 (2000), page 1268.

65. Barouch et al., *Cell* 155:1-9, 2013.

66. Yang et al. (2002) *J. Virol.* 76:4634.

67. Chen et al. (2004) *J. Virol.* 78:4508.

68. Nkolola et al., 2010. Breadth of Neutralizing Antibodies Elicited by Stable, Homogeneous Clade A and Clade C HIV-1 gp140 Envelope Trimers in Guinea Pigs. *J. Virology* 84 (7): 3270-3279.

69. Cohen et al, 2002, *J Gen Virol* 83: 151-55.

70. Kobinger et al, 2006, *Virology* 346: 394-401.

71. Tatsis et al., 2007, *Molecular Therapy* 15: 608-17.

72. Bangari and Mittal, 2006, *Vaccine* 24: 849-62.

73. Lasaro and Ertl, 2009, *Mol Ther* 17: 1333-39.

74. Mayr et al. (1975), *Infection* 3, 6-14.

75. Mayr, A. & Danner, K. (1978), *Dev. Biol. Stand.* 41: 225-234.

76. Mayr et al. (1978), *Zentralbl. Bacteriol.* (B) 167:375-390.

77. Stickl (1974), *Prev. Med.* 3: 97-101.

78. Stickl and Hochstein-Mintzel (1971), *Munch. Med. Wochenschr.* 113: 1149-1153.

79. Blanchard et al. (1998), *J. Gen. Virol.* 79:1159-1167.

80. Carroll & Moss (1997), *Virology* 238:198-211.

81. Ambrosini et al. (1999), *J. Neurosci. Res.* 55: 569.

82. Boukamp et al (1988), *J. Cell Biol.* 106: 761-771.

We claim:

1. A vaccine combination for inducing an immune response against a human immunodeficiency virus (HIV) in a subject, comprising:

(i) a primer composition comprising an immunogenically effective amount of one or more adenovirus 26 (rAd26) vectors encoding one or more HIV antigenic polypeptides comprising amino acid sequences selected from the group consisting of SEQ ID NOs: 1-4, and a pharmaceutically acceptable carrier;

(ii) a first booster composition comprising an immunogenically effective amount of an isolated HIV envelope polypeptide comprising at least one of a stabilized trimer of HIV gp140 comprising the amino acid sequence of SEQ ID NO: 5 and a stabilized trimer of HIV gp140 comprising the amino acid sequence of SEQ ID NO: 6, and a pharmaceutically acceptable carrier; and (iii) a second booster composition comprising an immunogenically effective amount of one or more MVA vectors encoding one or more HIV antigenic polypeptides comprising amino acid sequences selected from the group consisting of SEQ ID NOs: 1-4, respectively, wherein the first booster composition is for administration together with the second booster composition to the subject after administration of the primer composition.

2. The vaccine combination of claim 1, wherein the first and second booster compositions are present in separate compositions.

3. The vaccine combination of claim 1, wherein the primer composition comprises an immunogenically effective amount of one or more rAd26 vectors encoding HIV antigenic polypeptides having the amino acid sequences of SEQ ID NO: 1, SEQ ID NO: 3, and SEQ ID NO: 4, and a pharmaceutically acceptable carrier; and the second booster composition comprises an immunogenically effective amount of one or more MVA vectors encoding HIV antigenic polypeptides having the amino acid sequences of SEQ ID NO: 1, SEQ ID NO: 3, and SEQ ID NO: 4.

4. The vaccine combination of claim 3, wherein the one or more MVA vectors further encode an HIV antigenic polypeptide having the amino acid sequence of SEQ ID NO: 2.

5. The vaccine combination of claim 1, wherein the isolated HIV envelope polypeptide comprises a stabilized trimer of HIV gp140 comprising the amino acid sequence of SEQ ID NO: 5.

6. The vaccine combination of claim 1, wherein the isolated HIV envelope polypeptide comprises a stabilized trimer of HIV gp140 comprising the amino acid sequence of SEQ ID NO: 6.

7. The vaccine combination of claim 3, wherein the isolated HIV envelope polypeptide comprises a stabilized trimer of HIV gp140 comprising the amino acid sequence of SEQ ID NO: 5.

8. The vaccine combination of claim 1, wherein the first booster composition further comprises an adjuvant.

9. The vaccine combination of claim 8, wherein the adjuvant is aluminum phosphate or a saponin-based adjuvant.

10. A method of inducing an immune response against a human immunodeficiency virus (HIV) in a subject, the method comprising:
(i) administering to the subject a primer composition comprising an immunogenically effective amount of one or more adenovirus 26 (rAd26) vectors encoding one or more HIV antigenic polypeptides comprising amino acid sequences selected from the group consisting of SEQ ID NOs: 1-4, respectively, and a pharmaceutically acceptable carrier; and (ii) administering to the subject a first booster composition comprising an immunogenically effective amount of an isolated HIV envelope polypeptide comprising at least one of a stabilized trimer of HIV gp140 comprising the amino acid sequence of SEQ ID NO: 5 and a stabilized trimer of HIV gp140 comprising the amino acid sequence of SEQ ID NO: 6, and a pharmaceutically acceptable carrier; and (iii) administering to the subject a second booster composition together with the first booster composition, the second booster composition comprising an immunogenically effective amount of one or more MVA vectors encoding one or more HIV antigenic polypeptides comprising amino acid sequences selected from the group consisting of SEQ ID NOs: 1-4, respectively, and a pharmaceutically acceptable carrier;

wherein the first and second booster compositions are administered after the primer composition is administered.

11. The method of claim 10, wherein the first and second booster compositions are present in separate compositions.

12. The method of claim 10, wherein the first primer composition comprises an immunogenically effective amount of one or more rAd26 vectors encoding HIV antigenic polypeptides having the amino acid sequences of SEQ ID NO: 1, SEQ ID NO: 3, and SEQ ID NO: 4, and a pharmaceutically acceptable carrier; and the second booster composition comprises an immunogenically effective amount of one or more MVA vectors encoding HIV antigenic polypeptides having the amino acid sequences of SEQ ID NO: 1, SEQ ID NO: 3, and SEQ ID NO: 4.

13. The method of claim 12, wherein the one or more MVA vectors further encode an HIV antigenic polypeptide having the amino acid sequence of SEQ ID NO: 2.

14. The method of claim 10, wherein the isolated HIV envelope polypeptide comprises a stabilized trimer of HIV gp140 having the amino acid sequence of SEQ ID NO: 5.

15. The method of claim 10, wherein the isolated HIV envelope polypeptide comprises a stabilized trimer of HIV gp140 having the amino acid sequence of SEQ ID NO: 6.

16. The method of claim 12, wherein the isolated HIV envelope polypeptide comprises a stabilized trimer of HIV gp140 having the amino acid sequence of SEQ ID NO: 5.

17. The method of claim 10, wherein the second composition further comprises an adjuvant.

18. The method of claim 17, wherein the adjuvant is aluminum phosphate or a saponin-based adjuvant.

19. The method of claim 10, wherein the immune response generated is a protective immune response.

20. The method of claim 10, wherein the subject is a human.

* * * * *

SEQUENCE LISTING

```
<160> NUMBER OF SEQ ID NOS: 7

<210> SEQ ID NO 1
<211> LENGTH: 685
<212> TYPE: PRT
<213> ORGANISM: Artificial Sequence
<220> FEATURE:
<223> OTHER INFORMATION: Mos1.Env mosaic antigen sequence

<400> SEQUENCE: 1

Met Arg Val Thr Gly Ile Arg Lys Asn Tyr Gln His Leu Trp Arg Trp
1               5                   10                  15

Gly Thr Met Leu Leu Gly Ile Leu Met Ile Cys Ser Ala Ala Gly Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80
```

-continued

```
Gln Glu Val Val Leu Glu Asn Val Thr Glu Asn Phe Asn Met Trp Lys
             85                  90                  95
Asn Asn Met Val Glu Gln Met His Glu Asp Ile Ile Ser Leu Trp Asp
        100                 105                 110
Gln Ser Leu Lys Pro Cys Val Lys Leu Thr Pro Leu Cys Val Thr Leu
    115                 120                 125
Asn Cys Thr Asp Asp Val Arg Asn Val Thr Asn Asn Ala Thr Asn Thr
130                 135                 140
Asn Ser Ser Trp Gly Glu Pro Met Glu Lys Gly Glu Ile Lys Asn Cys
145                 150                 155                 160
Ser Phe Asn Ile Thr Thr Ser Ile Arg Asn Lys Val Gln Lys Gln Tyr
                165                 170                 175
Ala Leu Phe Tyr Lys Leu Asp Val Val Pro Ile Asp Asn Asp Ser Asn
            180                 185                 190
Asn Thr Asn Tyr Arg Leu Ile Ser Cys Asn Thr Ser Val Ile Thr Gln
        195                 200                 205
Ala Cys Pro Lys Val Ser Phe Glu Pro Ile Pro Ile His Tyr Cys Ala
210                 215                 220
Pro Ala Gly Phe Ala Ile Leu Lys Cys Asn Asp Lys Lys Phe Asn Gly
225                 230                 235                 240
Thr Gly Pro Cys Thr Asn Val Ser Thr Val Gln Cys Thr His Gly Ile
                245                 250                 255
Arg Pro Val Val Ser Thr Gln Leu Leu Leu Asn Gly Ser Leu Ala Glu
            260                 265                 270
Glu Glu Val Val Ile Arg Ser Glu Asn Phe Thr Asn Asn Ala Lys Thr
        275                 280                 285
Ile Met Val Gln Leu Asn Val Ser Val Glu Ile Asn Cys Thr Arg Pro
290                 295                 300
Asn Asn Asn Thr Arg Lys Ser Ile His Ile Gly Pro Gly Arg Ala Phe
305                 310                 315                 320
Tyr Thr Ala Gly Asp Ile Ile Gly Asp Ile Arg Gln Ala His Cys Asn
                325                 330                 335
Ile Ser Arg Ala Asn Trp Asn Asn Thr Leu Arg Gln Ile Val Glu Lys
            340                 345                 350
Leu Gly Lys Gln Phe Gly Asn Asn Lys Thr Ile Val Phe Asn His Ser
        355                 360                 365
Ser Gly Gly Asp Pro Glu Ile Val Met His Ser Phe Asn Cys Gly Gly
370                 375                 380
Glu Phe Phe Tyr Cys Asn Ser Thr Lys Leu Phe Asn Ser Thr Trp Thr
385                 390                 395                 400
Trp Asn Asn Ser Thr Trp Asn Asn Thr Lys Arg Ser Asn Asp Thr Glu
                405                 410                 415
Glu His Ile Thr Leu Pro Cys Arg Ile Lys Gln Ile Ile Asn Met Trp
            420                 425                 430
Gln Glu Val Gly Lys Ala Met Tyr Ala Pro Pro Ile Arg Gly Gln Ile
        435                 440                 445
Arg Cys Ser Ser Asn Ile Thr Gly Leu Leu Thr Arg Asp Gly Gly
450                 455                 460
Asn Asp Thr Ser Gly Thr Glu Ile Phe Arg Pro Gly Gly Gly Asp Met
465                 470                 475                 480
Arg Asp Asn Trp Arg Ser Glu Leu Tyr Lys Tyr Lys Val Val Lys Ile
                485                 490                 495
```

```
Glu Pro Leu Gly Val Ala Pro Thr Lys Ala Lys Arg Arg Val Val Gln
                500                 505                 510
Ser Glu Lys Ser Ala Val Gly Ile Gly Ala Val Phe Leu Gly Phe Leu
            515                 520                 525
Gly Ala Ala Gly Ser Thr Met Gly Ala Ala Ser Met Thr Leu Thr Val
        530                 535                 540
Gln Ala Arg Leu Leu Leu Ser Gly Ile Val Gln Gln Gln Asn Asn Leu
545                 550                 555                 560
Leu Arg Ala Ile Glu Ala Gln Gln His Leu Leu Gln Leu Thr Val Trp
                565                 570                 575
Gly Ile Lys Gln Leu Gln Ala Arg Val Leu Ala Val Glu Arg Tyr Leu
            580                 585                 590
Lys Asp Gln Gln Leu Leu Gly Ile Trp Gly Cys Ser Gly Lys Leu Ile
        595                 600                 605
Cys Thr Thr Thr Val Pro Trp Asn Ala Ser Trp Ser Asn Lys Ser Leu
610                 615                 620
Asp Lys Ile Trp Asn Asn Met Thr Trp Met Glu Trp Glu Arg Glu Ile
625                 630                 635                 640
Asn Asn Tyr Thr Ser Leu Ile Tyr Thr Leu Ile Glu Glu Ser Gln Asn
                645                 650                 655
Gln Gln Glu Lys Asn Glu Gln Glu Leu Leu Glu Leu Asp Lys Trp Ala
            660                 665                 670
Ser Leu Trp Asn Trp Phe Asp Ile Ser Asn Trp Leu Trp
        675                 680                 685

<210> SEQ ID NO 2
<211> LENGTH: 684
<212> TYPE: PRT
<213> ORGANISM: Artificial Sequence
<220> FEATURE:
<223> OTHER INFORMATION: Mos2.Env mosaic antigen sequence

<400> SEQUENCE: 2

Met Arg Val Arg Gly Ile Gln Arg Asn Trp Pro Gln Trp Trp Ile Trp
1               5                   10                  15
Gly Ile Leu Gly Phe Trp Met Ile Ile Cys Arg Val

```
Arg Leu Asp Ile Val Pro Leu Asp Glu Asn Ser Ser Glu Lys Ser
            180                 185                 190

Ser Glu Asn Ser Ser Glu Tyr Tyr Arg Leu Ile Asn Cys Asn Thr Ser
        195                 200                 205

Ala Ile Thr Gln Ala Cys Pro Lys Val Ser Phe Asp Pro Ile Pro Ile
    210                 215                 220

His Tyr Cys Ala Pro Ala Gly Tyr Ala Ile Leu Lys Cys Asn Asn Lys
225                 230                 235                 240

Thr Phe Asn Gly Thr Gly Pro Cys Asn Asn Val Ser Thr Val Gln Cys
            245                 250                 255

Thr His Gly Ile Lys Pro Val Val Ser Thr Gln Leu Leu Asn Gly
        260                 265                 270

Ser Leu Ala Glu Glu Ile Ile Ile Arg Ser Glu Asn Leu Thr Asn
        275                 280                 285

Asn Ala Lys Thr Ile Ile Val His Leu Asn Glu Thr Val Asn Ile Thr
    290                 295                 300

Cys Thr Arg Pro Asn Asn Asn Thr Arg Lys Ser Ile Arg Ile Gly Pro
305                 310                 315                 320

Gly Gln Thr Phe Tyr Ala Thr Gly Asp Ile Ile Gly Asp Ile Arg Gln
                325                 330                 335

Ala His Cys Asn Leu Ser Arg Asp Gly Trp Asn Lys Thr Leu Gln Gly
            340                 345                 350

Val Lys Lys Lys Leu Ala Glu His Phe Pro Asn Lys Thr Ile Asn Phe
        355                 360                 365

Thr Ser Ser Ser Gly Gly Asp Leu Glu Ile Thr Thr His Ser Phe Asn
    370                 375                 380

Cys Arg Gly Glu Phe Phe Tyr Cys Asn Thr Ser Gly Leu Phe Asn Gly
385                 390                 395                 400

Thr Tyr Met Pro Asn Gly Thr Asn Ser Asn Ser Ser Asn Ile Thr
                405                 410                 415

Leu Pro Cys Arg Ile Lys Gln Ile Ile Asn Met Trp Gln Glu Val Gly
            420                 425                 430

Arg Ala Met Tyr Ala Pro Pro Ile Ala Gly Asn Ile Thr Cys Arg Ser
        435                 440                 445

Asn Ile Thr Gly Leu Leu Leu Thr Arg Asp Gly Gly Ser Asn Asn Gly
    450                 455                 460

Val Pro Asn Asp Thr Glu Thr Phe Arg Pro Gly Gly Gly Asp Met Arg
465                 470                 475                 480

Asn Asn Trp Arg Ser Glu Leu Tyr Lys Tyr Lys Val Val Glu Val Lys
                485                 490                 495

Pro Leu Gly Val Ala Pro Thr Glu Ala Lys Arg Arg Val Val Glu Ser
            500                 505                 510

Glu Lys Ser Ala Val Gly Ile Gly Ala Val Phe Leu Gly Ile Leu Gly
        515                 520                 525

Ala Ala Gly Ser Thr Met Gly Ala Ala Ser Ile Thr Leu Thr Val Gln
    530                 535                 540

Ala Arg Gln Leu Leu Ser Gly Ile Val Gln Gln Ser Asn Leu Leu
545                 550                 555                 560

Arg Ala Ile Glu Ala Gln Gln His Met Leu Gln Leu Thr Val Trp Gly
                565                 570                 575

Ile Lys Gln Leu Gln Thr Arg Val Leu Ala Ile Glu Arg Tyr Leu Gln
            580                 585                 590
```

```
Asp Gln Gln Leu Leu Gly Leu Trp Gly Cys Ser Gly Lys Leu Ile Cys
            595                 600                 605

Thr Thr Ala Val Pro Trp Asn Thr Ser Trp Ser Asn Lys Ser Gln Thr
610                 615                 620

Asp Ile Trp Asp Asn Met Thr Trp Met Gln Trp Asp Lys Glu Ile Gly
625                 630                 635                 640

Asn Tyr Thr Gly Glu Ile Tyr Arg Leu Leu Glu Ser Gln Asn Gln
            645                 650                 655

Gln Glu Lys Asn Glu Lys Asp Leu Leu Ala Leu Asp Ser Trp Lys Asn
            660                 665                 670

Leu Trp Asn Trp Phe Asp Ile Thr Asn Trp Leu Trp
            675                 680

<210> SEQ ID NO 3
<211> LENGTH: 1350
<212> TYPE: PRT
<213> ORGANISM: Artificial Sequence
<220> FEATURE:
<223> OTHER INFORMATION: Mos1.Gag-Pol mosaic antigen sequence

<400> SEQUENCE: 3

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Arg Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Glu Lys Ile Glu Glu Glu Gln Asn Lys Ser Lys
            100                 105                 110

Lys Lys Ala Gln Gln Ala Ala Ala Asp Thr Gly Asn Ser Ser Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270
```

-continued

```
Ile Val Arg Met Tyr Ser Pro Val Ser Ile Leu Asp Ile Arg Gln Gly
            275                 280                 285

Pro Lys Glu Pro Phe Arg Asp Tyr Val Asp Arg Phe Tyr Lys Thr Leu
    290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
    355                 360                 365

Gln Val Thr Asn Ser Ala Thr Ile Met Met Gln Arg Gly Asn Phe Arg
370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Asn Lys Gly Arg Pro Gly Asn Phe
    435                 440                 445

Leu Gln Asn Arg Pro Glu Pro Thr Ala Pro Pro Glu Glu Ser Phe Arg
450                 455                 460

Phe Gly Glu Glu Thr Thr Thr Pro Ser Gln Lys Gln Glu Pro Ile Asp
465                 470                 475                 480

Lys Glu Met Tyr Pro Leu Ala Ser Leu Lys Ser Leu Phe Gly Asn Asp
                485                 490                 495

Pro Ser Ser Gln Met Ala Pro Ile Ser Pro Ile Glu Thr Val Pro Val
            500                 505                 510

Lys Leu Lys Pro Gly Met Asp Gly Pro Arg Val Lys Gln Trp Pro Leu
    515                 520                 525

Thr Glu Glu Lys Ile Lys Ala Leu Thr Ala Ile Cys Glu Glu Met Glu
530                 535                 540

Lys Glu Gly Lys Ile Thr Lys Ile Gly Pro Glu Asn Pro Tyr Asn Thr
545                 550                 555                 560

Pro Val Phe Ala Ile Lys Lys Lys Asp Ser Thr Lys Trp Arg Lys Leu
                565                 570                 575

Val Asp Phe Arg Glu Leu Asn Lys Arg Thr Gln Asp Phe Trp Glu Val
            580                 585                 590

Gln Leu Gly Ile Pro His Pro Ala Gly Leu Lys Lys Lys Lys Ser Val
    595                 600                 605

Thr Val Leu Ala Val Gly Asp Ala Tyr Phe Ser Val Pro Leu Asp Glu
610                 615                 620

Gly Phe Arg Lys Tyr Thr Ala Phe Thr Ile Pro Ser Thr Asn Asn Glu
625                 630                 635                 640

Thr Pro Gly Ile Arg Tyr Gln Tyr Asn Val Leu Pro Gln Gly Trp Lys
                645                 650                 655

Gly Ser Pro Ala Ile Phe Gln Cys Ser Met Thr Arg Ile Leu Glu Pro
            660                 665                 670

Phe Arg Ala Lys Asn Pro Glu Ile Val Ile Tyr Gln Tyr Met Ala Ala
    675                 680                 685
```

```
Leu Tyr Val Gly Ser Asp Leu Glu Ile Gly Gln His Arg Ala Lys Ile
    690                 695                 700

Glu Glu Leu Arg Glu His Leu Leu Lys Trp Gly Phe Thr Thr Pro Asp
705                 710                 715                 720

Lys Lys His Gln Lys Glu Pro Pro Phe Leu Trp Met Gly Tyr Glu Leu
                725                 730                 735

His Pro Asp Lys Trp Thr Val Gln Pro Ile Gln Leu Pro Glu Lys Asp
            740                 745                 750

Ser Trp Thr Val Asn Asp Ile Gln Lys Leu Val Gly Lys Leu Asn Trp
        755                 760                 765

Ala Ser Gln Ile Tyr Pro Gly Ile Lys Val Arg Gln Leu Cys Lys Leu
770                 775                 780

Leu Arg Gly Ala Lys Ala Leu Thr Asp Ile Val Pro Leu Thr Glu Glu
785                 790                 795                 800

Ala Glu Leu Glu Leu Ala Glu Asn Arg Glu Ile Leu Lys Glu Pro Val
                805                 810                 815

His Gly Val Tyr Tyr Asp Pro Ser Lys Asp Leu Ile Ala Glu Ile Gln
            820                 825                 830

Lys Gln Gly His Asp Gln Trp Thr Tyr Gln Ile Tyr Gln Glu Pro Phe
        835                 840                 845

Lys Asn Leu Lys Thr Gly Lys Tyr Ala Lys Met Arg Thr Ala His Thr
850                 855                 860

Asn Asp Val Lys Gln Leu Thr Glu Ala Val Gln Lys Ile Ala Met Glu
865                 870                 875                 880

Ser Ile Val Ile Trp Gly Lys Thr Pro Lys Phe Arg Leu Pro Ile Gln
                885                 890                 895

Lys Glu Thr Trp Glu Thr Trp Trp Thr Asp Tyr Trp Gln Ala Thr Trp
            900                 905                 910

Ile Pro Glu Trp Glu Phe Val Asn Thr Pro Pro Leu Val Lys Leu Trp
        915                 920                 925

Tyr Gln Leu Glu Lys Asp Pro Ile Ala Gly Val Glu Thr Phe Tyr Val
930                 935                 940

Ala Gly Ala Ala Asn Arg Glu Thr Lys Leu Gly Lys Ala Gly Tyr Val
945                 950                 955                 960

Thr Asp Arg Gly Arg Gln Lys Ile Val Ser Leu Thr Glu Thr Thr Asn
                965                 970                 975

Gln Lys Thr Ala Leu Gln Ala Ile Tyr Leu Ala Leu Gln Asp Ser Gly
            980                 985                 990

Ser Glu Val Asn Ile Val Thr Ala Ser Gln Tyr Ala Leu Gly Ile Ile
        995                 1000                1005

Gln Ala Gln Pro Asp Lys Ser Glu Ser Glu Leu Val Asn Gln Ile
    1010                1015                1020

Ile Glu Gln Leu Ile Lys Lys Glu Arg Val Tyr Leu Ser Trp Val
    1025                1030                1035

Pro Ala His Lys Gly Ile Gly Gly Asn Glu Gln Val Asp Lys Leu
    1040                1045                1050

Val Ser Ser Gly Ile Arg Lys Val Leu Phe Leu Asp Gly Ile Asp
    1055                1060                1065

Lys Ala Gln Glu Glu His Glu Lys Tyr His Ser Asn Trp Arg Ala
    1070                1075                1080

Met Ala Ser Asp Phe Asn Leu Pro Pro Val Val Ala Lys Glu Ile
    1085                1090                1095
```

-continued

```
Val Ala Ser Cys Asp Gln Cys Gln Leu Lys Gly Glu Ala Met His
    1100                1105                1110

Gly Gln Val Asp Cys Ser Pro Gly Ile Trp Gln Leu Ala Cys Thr
    1115                1120                1125

His Leu Glu Gly Lys Ile Ile Leu Val Ala Val His Val Ala Ser
    1130                1135                1140

Gly Tyr Ile Glu Ala Glu Val Ile Pro Ala Glu Thr Gly Gln Glu
    1145                1150                1155

Thr Ala Tyr Phe Ile Leu Lys Leu Ala Gly Arg Trp Pro Val Lys
    1160                1165                1170

Val Ile His Thr Ala Asn Gly Ser Asn Phe Thr Ser Ala Ala Val
    1175                1180                1185

Lys Ala Ala Cys Trp Trp Ala Gly Ile Gln Gln Glu Phe Gly Ile
    1190                1195                1200

Pro Tyr Asn Pro Gln Ser Gln Gly Val Val Ala Ser Met Asn Lys
    1205                1210                1215

Glu Leu Lys Lys Ile Ile Gly Gln Val Arg Asp Gln Ala Glu His
    1220                1225                1230

Leu Lys Thr Ala Val Gln Met Ala Val Phe Ile His Asn Phe Lys
    1235                1240                1245

Arg Lys Gly Gly Ile Gly Gly Tyr Ser Ala Gly Glu Arg Ile Ile
    1250                1255                1260

Asp Ile Ile Ala Thr Asp Ile Gln Thr Lys Glu Leu Gln Lys Gln
    1265                1270                1275

Ile Ile Lys Ile Gln Asn Phe Arg Val Tyr Tyr Arg Asp Ser Arg
    1280                1285                1290

Asp Pro Ile Trp Lys Gly Pro Ala Lys Leu Leu Trp Lys Gly Glu
    1295                1300                1305

Gly Ala Val Val Ile Gln Asp Asn Ser Asp Ile Lys Val Val Pro
    1310                1315                1320

Arg Arg Lys Val Lys Ile Ile Lys Asp Tyr Gly Lys Gln Met Ala
    1325                1330                1335

Gly Ala Asp Cys Val Ala Gly Arg Gln Asp Glu Asp
    1340                1345                1350

<210> SEQ ID NO 4
<211> LENGTH: 1341
<212> TYPE: PRT
<213> ORGANISM: Artificial Sequence
<220> FEATURE:
<223> OTHER INFORMATION: Mos2.Gag-Pol mosaic antigen sequence

<400> SEQUENCE: 4

Met Gly Ala Arg Ala Ser Ile Leu Arg Gly Gly Lys Leu Asp Lys Trp
  1               5                  10                  15

Glu Lys Ile Arg Leu Arg Pro Gly Gly Lys Lys His Tyr Met Leu Lys
                 20                  25                  30

His Leu Val Trp Ala Ser Arg Glu Leu Glu Arg Phe Ala Leu Asn Pro
             35                  40                  45

Gly Leu Leu Glu Thr Ser Glu Gly Cys Lys Gln Ile Ile Lys Gln Leu
         50                  55                  60

Gln Pro Ala Leu Gln Thr Gly Thr Glu Glu Leu Arg Ser Leu Phe Asn
 65                  70                  75                  80

Thr Val Ala Thr Leu Tyr Cys Val His Ala Glu Ile Glu Val Arg Asp
                 85                  90                  95
```

-continued

Thr Lys Glu Ala Leu Asp Lys Ile Glu Glu Gln Asn Lys Ser Gln
             100                 105                 110

Gln Lys Thr Gln Gln Ala Lys Glu Ala Asp Gly Lys Val Ser Gln Asn
        115                 120                 125

Tyr Pro Ile Val Gln Asn Leu Gln Gly Gln Met Val His Gln Pro Ile
        130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
        180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Val Ala Pro Gly Gln
210                 215                 220

Met Arg Glu Pro Arg Gly Ser Asp Ile Ala Gly Thr Thr Ser Asn Leu
225                 230                 235                 240

Gln Glu Gln Ile Ala Trp Met Thr Ser Asn Pro Pro Ile Pro Val Gly
                245                 250                 255

Asp Ile Tyr Lys Arg Trp Ile Ile Leu Gly Leu Asn Lys Ile Val Arg
                260                 265                 270

Met Tyr Ser Pro Thr Ser Ile Leu Asp Ile Lys Gln Gly Pro Lys Glu
            275                 280                 285

Pro Phe Arg Asp Tyr Val Asp Arg Phe Phe Lys Thr Leu Arg Ala Glu
        290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
            340                 345                 350

Pro Ser His Lys Ala Arg Val Leu Ala Glu Ala Met Ser Gln Thr Asn
        355                 360                 365

Ser Thr Ile Leu Met Gln Arg Ser Asn Phe Lys Gly Ser Lys Arg Ile
        370                 375                 380

Val Lys Cys Phe Asn Cys Gly Lys Glu Gly His Ile Ala Arg Asn Cys
385                 390                 395                 400

Arg Ala Pro Arg Lys Lys Gly Cys Trp Lys Cys Gly Lys Glu Gly His
                405                 410                 415

Gln Met Lys Asp Cys Thr Glu Arg Gln Ala Asn Phe Leu Gly Lys Ile
            420                 425                 430

Trp Pro Ser His Lys Gly Arg Pro Gly Asn Phe Leu Gln Ser Arg Pro
        435                 440                 445

Glu Pro Thr Ala Pro Pro Ala Glu Ser Phe Arg Phe Glu Glu Thr Thr
        450                 455                 460

Pro Ala Pro Lys Gln Glu Pro Lys Asp Arg Glu Pro Leu Thr Ser Leu
465                 470                 475                 480

Arg Ser Leu Phe Gly Ser Asp Pro Leu Ser Gln Met Ala Pro Ile Ser
                485                 490                 495

Pro Ile Glu Thr Val Pro Val Lys Leu Lys Pro Gly Met Asp Gly Pro
            500                 505                 510

-continued

```
Lys Val Lys Gln Trp Pro Leu Thr Glu Glu Lys Ile Lys Ala Leu Val
            515                 520                 525
Glu Ile Cys Thr Glu Met Glu Lys Gly Lys Ile Ser Lys Ile Gly
            530                 535                 540
Pro Glu Asn Pro Tyr Asn Thr Pro Ile Phe Ala Ile Lys Lys Lys Asp
545                 550                 555                 560
Ser Thr Lys Trp Arg Lys Leu Val Asp Phe Arg Glu Leu Asn Lys Arg
            565                 570                 575
Thr Gln Asp Phe Trp Glu Val Gln Leu Gly Ile Pro His Pro Ala Gly
            580                 585                 590
Leu Lys Lys Lys Lys Ser Val Thr Val Leu Ala Val Gly Asp Ala Tyr
            595                 600                 605
Phe Ser Val Pro Leu Asp Glu Asp Phe Arg Lys Tyr Thr Ala Phe Thr
            610                 615                 620
Ile Pro Ser Ile Asn Asn Glu Thr Pro Gly Ile Arg Tyr Gln Tyr Asn
625                 630                 635                 640
Val Leu Pro Gln Gly Trp Lys Gly Ser Pro Ala Ile Phe Gln Ser Ser
            645                 650                 655
Met Thr Lys Ile Leu Glu Pro Phe Arg Lys Gln Asn Pro Asp Ile Val
            660                 665                 670
Ile Tyr Gln Tyr Met Ala Ala Leu Tyr Val Gly Ser Asp Leu Glu Ile
            675                 680                 685
Gly Gln His Arg Thr Lys Ile Glu Glu Leu Arg Gln His Leu Leu Arg
            690                 695                 700
Trp Gly Phe Thr Thr Pro Asp Lys Lys His Gln Lys Glu Pro Pro Phe
705                 710                 715                 720
Leu Trp Met Gly Tyr Glu Leu His Pro Asp Lys Trp Thr Val Gln Pro
            725                 730                 735
Ile Val Leu Pro Glu Lys Asp Ser Trp Thr Val Asn Asp Ile Gln Lys
            740                 745                 750
Leu Val Gly Lys Leu Asn Trp Ala Ser Gln Ile Tyr Ala Gly Ile Lys
            755                 760                 765
Val Lys Gln Leu Cys Lys Leu Leu Arg Gly Thr Lys Ala Leu Thr Glu
            770                 775                 780
Val Val Pro Leu Thr Glu Glu Ala Glu Leu Glu Leu Ala Glu Asn Arg
785                 790                 795                 800
Glu Ile Leu Lys Glu Pro Val His Gly Val Tyr Tyr Asp Pro Ser Lys
            805                 810                 815
Asp Leu Ile Ala Glu Ile Gln Lys Gln Gly Gln Gly Gln Trp Thr Tyr
            820                 825                 830
Gln Ile Tyr Gln Glu Pro Phe Lys Asn Leu Lys Thr Gly Lys Tyr Ala
            835                 840                 845
Arg Met Arg Gly Ala His Thr Asn Asp Val Lys Gln Leu Thr Glu Ala
            850                 855                 860
Val Gln Lys Ile Ala Thr Glu Ser Ile Val Ile Trp Gly Lys Thr Pro
865                 870                 875                 880
Lys Phe Lys Leu Pro Ile Gln Lys Glu Thr Trp Glu Ala Trp Trp Thr
            885                 890                 895
Glu Tyr Trp Gln Ala Thr Trp Ile Pro Glu Trp Glu Phe Val Asn Thr
            900                 905                 910
Pro Pro Leu Val Lys Leu Trp Tyr Gln Leu Glu Lys Glu Pro Ile Val
            915                 920                 925
```

```
Gly Ala Glu Thr Phe Tyr Val Ala Gly Ala Ala Asn Arg Glu Thr Lys
930                 935                 940

Leu Gly Lys Ala Gly Tyr Val Thr Asp Arg Gly Arg Gln Lys Val Val
945                 950                 955                 960

Ser Leu Thr Asp Thr Thr Asn Gln Lys Thr Ala Leu Gln Ala Ile His
            965                 970                 975

Leu Ala Leu Gln Asp Ser Gly Leu Glu Val Asn Ile Val Thr Ala Ser
            980                 985                 990

Gln Tyr Ala Leu Gly Ile Ile Gln Ala Gln Pro Asp Lys Ser Glu Ser
            995                 1000                1005

Glu Leu Val Ser Gln Ile Ile Glu Gln Leu Ile Lys Lys Glu Lys
    1010                1015                1020

Val Tyr Leu Ala Trp Val Pro Ala His Lys Gly Ile Gly Gly Asn
    1025                1030                1035

Glu Gln Val Asp Lys Leu Val Ser Arg Gly Ile Arg Lys Val Leu
    1040                1045                1050

Phe Leu Asp Gly Ile Asp Lys Ala Gln Glu Glu His Glu Lys Tyr
    1055                1060                1065

His Ser Asn Trp Arg Ala Met Ala Ser Glu Phe Asn Leu Pro Pro
    1070                1075                1080

Ile Val Ala Lys Glu Ile Val Ala Ser Cys Asp Lys Cys Gln Leu
    1085                1090                1095

Lys Gly Glu Ala Ile His Gly Gln Val Asp Cys Ser Pro Gly Ile
    1100                1105                1110

Trp Gln Leu Ala Cys Thr His Leu Glu Gly Lys Val Ile Leu Val
    1115                1120                1125

Ala Val His Val Ala Ser Gly Tyr Ile Glu Ala Glu Val Ile Pro
    1130                1135                1140

Ala Glu Thr Gly Gln Glu Thr Ala Tyr Phe Leu Leu Lys Leu Ala
    1145                1150                1155

Gly Arg Trp Pro Val Lys Thr Ile His Thr Ala Asn Gly Ser Asn
    1160                1165                1170

Phe Thr Ser Ala Thr Val Lys Ala Ala Cys Trp Trp Ala Gly Ile
    1175                1180                1185

Lys Gln Glu Phe Gly Ile Pro Tyr Asn Pro Gln Ser Gln Gly Val
    1190                1195                1200

Val Ala Ser Ile Asn Lys Glu Leu Lys Lys Ile Ile Gly Gln Val
    1205                1210                1215

Arg Asp Gln Ala Glu His Leu Lys Thr Ala Val Gln Met Ala Val
    1220                1225                1230

Phe Ile His Asn Phe Lys Arg Lys Gly Gly Ile Gly Glu Tyr Ser
    1235                1240                1245

Ala Gly Glu Arg Ile Val Asp Ile Ile Ala Ser Asp Ile Gln Thr
    1250                1255                1260

Lys Glu Leu Gln Lys Gln Ile Thr Lys Ile Gln Asn Phe Arg Val
    1265                1270                1275

Tyr Tyr Arg Asp Ser Arg Asp Pro Leu Trp Lys Gly Pro Ala Lys
    1280                1285                1290

Leu Leu Trp Lys Gly Glu Gly Ala Val Val Ile Gln Asp Asn Ser
    1295                1300                1305

Asp Ile Lys Val Val Pro Arg Arg Lys Ala Lys Ile Ile Arg Asp
    1310                1315                1320
```

Tyr Gly Lys Gln Met Ala Gly Asp Asp Cys Val Ala Ser Arg Gln
1325            1330                1335

Asp Glu Asp
    1340

<210> SEQ ID NO 5
<211> LENGTH: 679
<212> TYPE: PRT
<213> ORGANISM: Artificial Sequence
<220> FEATURE:
<223> OTHER INFORMATION: clade C gp140 trimeric protein

<400> SEQUENCE: 5

Ala Glu Asn Leu Trp Val Gly Asn Met Trp Val Thr Val Tyr Tyr Gly
1               5                   10                  15

Val Pro Val Trp Thr Asp Ala Lys Thr Thr Leu Phe Cys Ala Ser Asp
            20                  25                  30

Thr Lys Ala Tyr Asp Arg Glu Val His Asn Val Trp Ala Thr His Ala
        35                  40                  45

Cys Val Pro Thr Asp Pro Asn Pro Gln Glu Ile Val Leu Glu Asn Val
    50                  55                  60

Thr Glu Asn Phe Asn Met Trp Lys Asn Asp Met Val Asp Gln Met His
65                  70                  75                  80

Glu Asp Ile Ile Ser Leu Trp Asp Gln Ser Leu Lys Pro Cys Val Lys
                85                  90                  95

Leu Thr Pro Leu Cys Val Thr Leu His Cys Thr Asn Ala Thr Phe Lys
            100                 105                 110

Asn Asn Val Thr Asn Asp Met Asn Lys Glu Ile Arg Asn Cys Ser Phe
        115                 120                 125

Asn Thr Thr Thr Glu Ile Arg Asp Lys Lys Gln Gln Gly Tyr Ala Leu
    130                 135                 140

Phe Tyr Arg Pro Asp Ile Val Leu Leu Lys Glu Asn Arg Asn Asn Ser
145                 150                 155                 160

Asn Asn Ser Glu Tyr Ile Leu Ile Asn Cys Asn Ala Ser Thr Ile Thr
                165                 170                 175

Gln Ala Cys Pro Lys Val Asn Phe Asp Pro Ile Pro Ile His Tyr Cys
            180                 185                 190

Ala Pro Ala Gly Tyr Ala Ile Leu Lys Cys Asn Asn Lys Thr Phe Ser
        195                 200                 205

Gly Lys Gly Pro Cys Asn Asn Val Ser Thr Val Gln Cys Thr His Gly
    210                 215                 220

Ile Lys Pro Val Val Ser Thr Gln Leu Leu Leu Asn Gly Ser Leu Ala
225                 230                 235                 240

Glu Lys Glu Ile Ile Ile Arg Ser Glu Asn Leu Thr Asp Asn Val Lys
                245                 250                 255

Thr Ile Ile Val His Leu Asn Lys Ser Val Glu Ile Val Cys Thr Arg
            260                 265                 270

Pro Asn Asn Asn Thr Arg Lys Ser Met Arg Ile Gly Pro Gly Gln Thr
        275                 280                 285

Phe Tyr Ala Thr Gly Asp Ile Ile Gly Asp Ile Arg Gln Ala Tyr Cys
    290                 295                 300

Asn Ile Ser Gly Ser Lys Trp Asn Glu Thr Leu Lys Arg Val Lys Glu
305                 310                 315                 320

Lys Leu Gln Glu Asn Tyr Asn Asn Asn Lys Thr Ile Lys Phe Ala Pro
                325                 330                 335

```
Ser Ser Gly Gly Asp Leu Glu Ile Thr Thr His Ser Phe Asn Cys Arg
            340                 345                 350

Gly Glu Phe Phe Tyr Cys Asn Thr Thr Arg Leu Phe Asn Asn Asn Ala
            355                 360                 365

Thr Glu Asp Glu Thr Ile Thr Leu Pro Cys Arg Ile Lys Gln Ile Ile
        370                 375                 380

Asn Met Trp Gln Gly Val Gly Arg Ala Met Tyr Ala Pro Pro Ile Ala
385                 390                 395                 400

Gly Asn Ile Thr Cys Lys Ser Asn Ile Thr Gly Leu Leu Leu Val Arg
                405                 410                 415

Asp Gly Gly Glu Asp Asn Lys Thr Glu Glu Ile Phe Arg Pro Gly Gly
            420                 425                 430

Gly Asn Met Lys Asp Asn Trp Arg Ser Glu Leu Tyr Lys Tyr Lys Val
            435                 440                 445

Ile Glu Leu Lys Pro Leu Gly Ile Ala Pro Thr Gly Ala Lys Glu Arg
            450                 455                 460

Val Val Glu Arg Glu Glu Arg Ala Val Gly Ile Gly Ala Val Phe Leu
465                 470                 475                 480

Gly Phe Leu Gly Ala Ala Gly Ser Thr Met Gly Ala Ala Ser Leu Thr
                485                 490                 495

Leu Thr Val Gln Ala Arg Gln Leu Leu Ser Ser Ile Val Gln Gln Gln
            500                 505                 510

Ser Asn Leu Leu Arg Ala Ile Glu Ala Gln Gln His Met Leu Gln Leu
            515                 520                 525

Thr Val Trp Gly Ile Lys Gln Leu Gln Thr Arg Val Leu Ala Ile Glu
            530                 535                 540

Arg Tyr Leu Lys Asp Gln Gln Leu Leu Gly Ile Trp Gly Cys Ser Gly
545                 550                 555                 560

Lys Leu Ile Cys Thr Thr Asn Val Pro Trp Asn Ser Ser Trp Ser Asn
                565                 570                 575

Lys Ser Gln Thr Asp Ile Trp Asn Asn Met Thr Trp Met Glu Trp Asp
            580                 585                 590

Arg Glu Ile Ser Asn Tyr Thr Asp Thr Ile Tyr Arg Leu Leu Glu Asp
            595                 600                 605

Ser Gln Thr Gln Gln Glu Lys Asn Glu Lys Asp Leu Leu Ala Leu Asp
            610                 615                 620

Ser Trp Lys Asn Leu Trp Ser Trp Phe Asp Ile Ser Asn Trp Leu Trp
625                 630                 635                 640

Tyr Ile Lys Ser Arg Ile Glu Gly Arg Gly Ser Gly Gly Tyr Ile Pro
                645                 650                 655

Glu Ala Pro Arg Asp Gly Gln Ala Tyr Val Arg Lys Asp Gly Glu Trp
            660                 665                 670

Val Leu Leu Ser Thr Phe Leu
            675

<210> SEQ ID NO 6
<211> LENGTH: 695
<212> TYPE: PRT
<213> ORGANISM: Artificial Sequence
<220> FEATURE:
<223> OTHER INFORMATION: mosaic gp140 chimeric protein
```

<400> SEQUENCE: 6

```
Ala Gly Lys Leu Trp Val Thr Val Tyr Tyr Gly Val Pro Val Trp Lys
1               5                   10                  15
Glu Ala Thr Thr Thr Leu Phe Cys Ala Ser Asp Ala Lys Ala Tyr Asp
            20                  25                  30
Thr Glu Val His Asn Val Trp Ala Thr His Ala Cys Val Pro Thr Asp
        35                  40                  45
Pro Asn Pro Gln Glu Val Val Leu Glu Asn Val Thr Glu Asn Phe Asn
    50                  55                  60
Met Trp Lys Asn Asn Met Val Glu Gln Met His Glu Asp Ile Ile Ser
65                  70                  75                  80
Leu Trp Asp Gln Ser Leu Lys Pro Cys Val Lys Leu Thr Pro Leu Cys
                85                  90                  95
Val Thr Leu Asn Cys Thr Asp Asp Val Arg Asn Val Thr Asn Asn Ala
            100                 105                 110
Thr Asn Thr Asn Ser Ser Trp Gly Glu Pro Met Glu Lys Gly Glu Ile
        115                 120                 125
Lys Asn Cys Ser Phe Asn Ile Thr Thr Ser Ile Arg Asn Lys Val Gln
    130                 135                 140
Lys Gln Tyr Ala Leu Phe Tyr Lys Leu Asp Val Val Pro Ile Asp Asn
145                 150                 155                 160
Asp Ser Asn Asn Thr Asn Tyr Arg Leu Ile Ser Cys Asn Thr Ser Val
                165                 170                 175
Ile Thr Gln Ala Cys Pro Lys Val Ser Phe Glu Pro Ile Pro Ile His
            180                 185                 190
Tyr Cys Ala Pro Ala Gly Phe Ala Ile Leu Lys Cys Asn Asp Lys Lys
        195                 200                 205
Phe Asn Gly Thr Gly Pro Cys Thr Asn Val Ser Thr Val Gln Cys Thr
    210                 215                 220
His Gly Ile Arg Pro Val Val Ser Thr Gln Leu Leu Leu Asn Gly Ser
225                 230                 235                 240
Leu Ala Glu Glu Glu Val Val Ile Arg Ser Glu Asn Phe Thr Asn Asn
                245                 250                 255
Ala Lys Thr Ile Met Val Gln Leu Asn Val Ser Val Glu Ile Asn Cys
            260                 265                 270
Thr Arg Pro Asn Asn Asn Thr Arg Lys Ser Ile His Ile Gly Pro Gly
        275                 280                 285
Arg Ala Phe Tyr Thr Ala Gly Asp Ile Ile Gly Asp Ile Arg Gln Ala
    290                 295                 300
His Cys Asn Ile Ser Arg Ala Asn Trp Asn Asn Thr Leu Arg Gln Ile
305                 310                 315                 320
Val Glu Lys Leu Gly Lys Gln Phe Gly Asn Asn Lys Thr Ile Val Phe
                325                 330                 335
Asn His Ser Ser Gly Gly Asp Pro Glu Ile Val Met His Ser Phe Asn
            340                 345                 350
Cys Gly Gly Glu Phe Phe Tyr Cys Asn Ser Thr Lys Leu Phe Asn Ser
        355                 360                 365
Thr Trp Thr Trp Asn Asn Ser Thr Trp Asn Asn Thr Lys Arg Ser Asn
    370                 375                 380
Asp Thr Glu Glu His Ile Thr Leu Pro Cys Arg Ile Lys Gln Ile Ile
385                 390                 395                 400
Asn Met Trp Gln Glu Val Gly Lys Ala Met Tyr Ala Pro Pro Ile Arg
                405                 410                 415
```

-continued

```
Gly Gln Ile Arg Cys Ser Ser Asn Ile Thr Gly Leu Leu Leu Thr Arg
                420                 425                 430

Asp Gly Gly Asn Asp Thr Ser Gly Thr Glu Ile Phe Arg Pro Gly Gly
            435                 440                 445

Gly Asp Met Arg Asp Asn Trp Arg Ser Glu Leu Tyr Lys Tyr Lys Val
        450                 455                 460

Val Lys Ile Glu Pro Leu Gly Val Ala Pro Thr Lys Ala Lys Glu Arg
465                 470                 475                 480

Val Val Gln Arg Glu Glu Arg Ala Val Gly Ile Gly Ala Val Phe Leu
                485                 490                 495

Gly Phe Leu Gly Ala Ala Gly Ser Thr Met Gly Ala Ala Ser Met Thr
            500                 505                 510

Leu Thr Val Gln Ala Arg Leu Leu Leu Ser Gly Ile Val Gln Gln Gln
        515                 520                 525

Asn Asn Leu Leu Arg Ala Ile Glu Ala Gln Gln His Leu Leu Gln Leu
530                 535                 540

Thr Val Trp Gly Ile Lys Gln Leu Gln Ala Arg Val Leu Ala Val Glu
545                 550                 555                 560

Arg Tyr Leu Lys Asp Gln Gln Leu Leu Gly Ile Trp Gly Cys Ser Gly
                565                 570                 575

Lys Leu Ile Cys Thr Thr Thr Val Pro Trp Asn Ala Ser Trp Ser Asn
            580                 585                 590

Lys Ser Leu Asp Lys Ile Trp Asn Asn Met Thr Trp Met Glu Trp Glu
        595                 600                 605

Arg Glu Ile Asn Asn Tyr Thr Ser Leu Ile Tyr Thr Leu Ile Glu Glu
610                 615                 620

Ser Gln Asn Gln Gln Glu Lys Asn Glu Gln Glu Leu Leu Glu Leu Asp
625                 630                 635                 640

Lys Trp Ala Ser Leu Trp Asn Trp Phe Asp Ile Ser Asn Trp Leu Trp
                645                 650                 655

Tyr Ile Lys Ser Arg Ile Glu Gly Arg Gly Ser Gly Gly Tyr Ile Pro
            660                 665                 670

Glu Ala Pro Arg Asp Gly Gln Ala Tyr Val Arg Lys Asp Gly Glu Trp
        675                 680                 685

Val Leu Leu Ser Thr Phe Leu
    690                 695

<210> SEQ ID NO 7
<211> LENGTH: 29
<212> TYPE: PRT
<213> ORGANISM: Artificial Sequence
<220> FEATURE:
<223> OTHER INFORMATION: exemplary leader sequence for gp140 stabilized
      trimeric protein production

<400> SEQUENCE: 7

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala
            20                  25
```